US011424411B2

United States Patent
Mujica-Fernaud et al.

(10) Patent No.: US 11,424,411 B2
(45) Date of Patent: *Aug. 23, 2022

(54) PHENANTHRENE COMPOUNDS FOR ORGANIC ELECTRONIC DEVICES

(71) Applicant: Merck Patent GmbH, Darmstadt (DE)

(72) Inventors: Teresa Mujica-Fernaud, Darmstadt (DE); Arne Buesing, Frankfurt am Main (DE); Frank Voges, Bad Duerkheim (DE); Jonas Kroeber, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 363 days.

This patent is subject to a terminal disclaimer.

(21) Appl. No.: 16/561,188

(22) Filed: Sep. 5, 2019

(65) Prior Publication Data

US 2019/0393414 A1    Dec. 26, 2019

Related U.S. Application Data

(60) Continuation of application No. 15/783,333, filed on Oct. 13, 2017, which is a division of application No. (Continued)

(30) Foreign Application Priority Data

Jun. 6, 2012   (DE) .......................... 102012011335.8

(51) Int. Cl.
| | | |
|---|---|---|
| H01L 51/50 | (2006.01) | |
| H01L 51/00 | (2006.01) | |
| C09B 19/00 | (2006.01) | |
| C09B 21/00 | (2006.01) | |
| C09B 57/00 | (2006.01) | |
| C09B 69/00 | (2006.01) | |
| C07D 307/93 | (2006.01) | |
| C07D 311/80 | (2006.01) | |
| C07D 223/26 | (2006.01) | |

(Continued)

(52) U.S. Cl.
CPC .......... *H01L 51/006* (2013.01); *C07C 209/60* (2013.01); *C07C 211/61* (2013.01); *C07C 217/80* (2013.01); *C07D 209/86* (2013.01); *C07D 209/94* (2013.01); *C07D 213/06* (2013.01); *C07D 213/16* (2013.01); *C07D 219/02* (2013.01); *C07D 221/08* (2013.01); *C07D 223/26* (2013.01); *C07D 265/38* (2013.01); *C07D 279/22* (2013.01); *C07D 307/91* (2013.01); *C07D 307/93* (2013.01); *C07D 311/80* (2013.01); *C07D 333/76* (2013.01); *C07D 405/04* (2013.01); *C07D 405/12* (2013.01); *C07D 407/12* (2013.01); *C07D 471/06* (2013.01); *C07D 487/04* (2013.01); *C09B 19/00* (2013.01); *C09B 21/00* (2013.01); *C09B 57/008* (2013.01); *C09B 69/008* (2013.01); *C09K 11/06* (2013.01); *H01L 51/0061* (2013.01); *H01L 51/0072* (2013.01); *H01L 51/0073* (2013.01); *H01L 51/0074* (2013.01); *C07C 2601/14* (2017.05); *C07C 2603/18* (2017.05); *C07C 2603/26* (2017.05); *C07C 2603/52* (2017.05); *C07C 2603/54* (2017.05); *C07C 2603/94* (2017.05); *C07C 2603/97* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0052* (2013.01); *H01L 51/0058* (2013.01); *H01L 51/5012* (2013.01); *H01L 51/5056* (2013.01); *H01L 51/5088* (2013.01); *H01L 51/5096* (2013.01); *Y02E 10/549* (2013.01)

(58) Field of Classification Search
CPC .. C07D 307/91; C07D 209/86; C07D 311/80; C07D 471/06; C07D 487/04; C07D 265/38; C07D 209/94; C07D 333/76; C07D 221/08; C09K 2211/1007; C09K 2211/1011; C09K 2211/1014; C09K 2211/1029; C09K 2211/1088; C09K 2211/10

See application file for complete search history.

(56) References Cited

U.S. PATENT DOCUMENTS

| | | |
|---|---|---|
| 9,065,060 B2 | 6/2015 | Hong et al. |
| 2007/0205714 A1 | 9/2007 | Busing et al. |

(Continued)

FOREIGN PATENT DOCUMENTS

| | | |
|---|---|---|
| CN | 1947275 A | 4/2007 |
| CN | 103403125 A | 11/2013 |

(Continued)

OTHER PUBLICATIONS

Buchwald et al., Palladium-Catalyzed Aromatic Animations with in Situ Generated Aminostannanes, Journal American Chemical Soc., 116, pp. 7901-7902, 1994.
Chinese Office Action for Application No. 201380029898.9, dated Apr. 12, 2016.
Harris, M., et al., "One-Pot Synthesis of Unsymmetrical Triarylamines from Aniline Precursors", Journal of Organic Chemistry, 2000, vol. 65, No. 17, pp. 5327-5333.

(Continued)

*Primary Examiner* — Gregory D Clark
(74) *Attorney, Agent, or Firm* — Faegre Drinker Biddle & Reath LLP

(57) ABSTRACT

The invention relates to specific phenanthrenes, the use of the compound in an electronic device, and an electronic device containing at least one of said compounds. The invention further relates to a method for producing the compound and a formulation and composition containing one or more of the compounds.

18 Claims, No Drawings

Related U.S. Application Data

14/406,059, filed as application No. PCT/EP2013/001333 on May 6, 2013, now Pat. No. 9,799,833.

(51) Int. Cl.

| | |
|---|---|
| *C07D 405/04* | (2006.01) |
| *C07D 405/12* | (2006.01) |
| *C07C 217/80* | (2006.01) |
| *C07D 471/06* | (2006.01) |
| *C07D 487/04* | (2006.01) |
| *C07D 265/38* | (2006.01) |
| *C07D 279/22* | (2006.01) |
| *C07D 209/94* | (2006.01) |
| *C07D 213/06* | (2006.01) |
| *C07D 213/16* | (2006.01) |
| *C07D 219/02* | (2006.01) |
| *C07D 333/76* | (2006.01) |
| *C07C 211/61* | (2006.01) |
| *C07D 307/91* | (2006.01) |
| *C09K 11/06* | (2006.01) |
| *C07D 407/12* | (2006.01) |
| *C07D 209/86* | (2006.01) |
| *C07C 209/60* | (2006.01) |
| *C07D 221/08* | (2006.01) |

(56) References Cited

U.S. PATENT DOCUMENTS

| | | | |
|---|---|---|---|
| 2010/0109555 | A1 | 5/2010 | Ichimura et al. |
| 2010/0288974 | A1 | 11/2010 | Buesing et al. |
| 2012/0163860 | A1 | 6/2012 | Shimoyama et al. |
| 2012/0199820 | A1 | 8/2012 | Ito et al. |
| 2013/0193382 | A1 | 8/2013 | Buesing et al. |
| 2013/0256649 | A1 | 10/2013 | Huh et al. |
| 2013/0334517 | A1 | 12/2013 | Hong et al. |

FOREIGN PATENT DOCUMENTS

| | | |
|---|---|---|
| EP | 2602243 A1 | 6/2013 |
| JP | H04321649 A | 11/1992 |
| JP | 2005170866 A | 6/2005 |
| JP | 2006151844 A | 6/2006 |
| JP | 2011173972 A | 9/2011 |
| JP | 2012027072 A | 2/2012 |
| JP | 2012507590 A | 3/2012 |
| JP | 2012137599 A | 7/2012 |
| JP | 2014511352 A | 5/2014 |
| JP | 2014167946 A | 9/2014 |
| JP | 2015155378 A | 8/2015 |
| KR | 20080033523 A | 4/2008 |
| WO | WO-2005/104264 A1 | 11/2005 |
| WO | WO-2008149968 A1 | 12/2008 |
| WO | WO-2010050779 A1 | 5/2010 |
| WO | WO-2011019360 A1 | 2/2011 |
| WO | WO-2011136482 A1 | 11/2011 |
| WO | WO-2011136484 A1 | 11/2011 |
| WO | WO-2012018120 A1 | 2/2012 |
| WO | WO-2012048780 A1 | 4/2012 |
| WO | WO-2012091428 A2 | 7/2012 |
| WO | WO-2012099376 A2 | 7/2012 |

OTHER PUBLICATIONS

Hartwig et al., Palladium-Catalyzed Formation of Carbon-Nitrogen Bonds. Reaction Intermediates and Catalyst Improments in Hetero Cross-Coupling of Aryl Halides and Tin Amides, Journal American Chemical Soc., 116, pp. 5969-5970, 1994.

International Search Report for PCT/EP2013/001333 dated Aug. 8, 2013.

Jamieson et al., "Photochemical Reactions of AZO Compounds. IX. Further studies related to the photochemical reactions of bisazo compounds", Australian Journal of Chemistry, vol. 20, Issue 2, pp. 321-328 (1967).

Klapars, A., et al., "A General and Efficient Copper Catalyst for the Amidation of Aryl Halides and the N-Arylation of Nitrogen Heterocycles", Journal of American Chemical Society, vol. 123, (2001), pp. 7727-7729.

Korean Notice of Grounds of Rejection for application No. 2015-700027 7, dated Nov. 4, 2016.

Liu, X., et al., "New rhenium(I) complexes with substituted diimine ligands for highly efficient phosphorescent devices fabricated by a solution process", Journal of Materials Chemistry, vol. 22, No. 8, (2012), pp. 3485-3492.

Office action for corresponding Japanese patent application 2018-076015 dated Jan. 8, 2019 (English translation).

PHENANTHRENE COMPOUNDS FOR ORGANIC ELECTRONIC DEVICES

CROSS-REFERENCE TO RELATED APPLICATIONS

This application is a continuation application of application Ser. No. 15/783,333 filed Oct. 13, 2017, which is incorporated by reference in its entirety. Application Ser. No. 15/783,333 is a divisional application of application Ser. No. 14/406,059 filed Dec. 5, 2014, which is incorporated by reference in its entirety. Application Ser. No. 14/406,059 is a national stage application (under 35 U.S.C. § 371) of PCT/EP2013/001333, filed May 6, 2013, which claims benefit of German Application No. 10 2012 011 335.8, filed Jun. 6, 2012, both of which are incorporated herein by reference in their entirety.

The present invention relates to novel organic compounds, to the use of the compound in an electronic device, and to an electronic device comprising at least one of the compounds. The present invention furthermore relates to a process for the preparation of the compounds and to compositions and formulations and comprising at least one of the compounds.

The development of functional compounds for use in electronic devices is currently the subject of intensive research. The aim here is, in particular, the development of compounds with which improved properties of the electronic devices can be achieved in one or more relevant points, such as, for example, performance efficiency, lifetime or colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices referred to as OLEDs. The general structure and functional principle of OLEDs is known to the person skilled in the art and is described, inter alia, in U.S. Pat. Nos. 4,539,507, 5,151,629, EP 0676461 and WO 1998/27136.

Regarding the performance data of OLEDs, further improvements are still necessary, in particular in view of broad commercial use, for example in display devices or as light sources. Of particular importance in this connection are the lifetime, the efficiency and the operating voltage of the OLEDs and the colour values achieved. In addition, it is desirable for the compounds for use as functional materials in electronic devices to have high thermal stability and a high glass-transition temperature and to be sublimable without decomposition.

In this connection, there is, in particular, a need for alternative hole-transport materials. In the case of hole-transport materials in accordance with the prior art, the voltage generally increases with the layer thickness of the hole-transport layer. In practice, a greater layer thickness of the hole-transport layer would frequently be desirable, but this frequently has the consequence of a higher operating voltage and worse performance data. In this connection, there is a need for novel hole-transport materials which have high charge-carrier mobility, so that thicker hole-transport layers having only a slight increase in the operating voltage can be achieved.

The prior art discloses the use, in particular, of arylamine compounds and carbazole compounds as hole-transport materials for OLEDs.

The application WO 2010/083871 discloses the use of dihydroacridine derivatives which are substituted by one or more arylamino groups as functional materials in OLEDs, preferably as hole-transport and hole-injection materials.

KR 2011047803 discloses phenanthrenes, which may be diamines or monoamines, where the amine group in the case of the monoamine is not bonded via position 3 of the phenanthrene.

JP 1992321649 discloses aromatic tertiary amines which contain two alkene groups. Also disclosed is a single compound which exhibits a phenanthrene which contains an amine group in position 3, where the amine is furthermore substituted by two aromatic groups which themselves each contain an aklene group.

US 2008/0182129 discloses anthracenes which are substituted by amoratic amines, where the aromatic group may also be a phenanthrene.

WO 2011/136482 describes substituted phenanthrenes as charge-transport compounds. The phenanthrenes disclosed herein are at least disubstituted where both substituents contain an amine group.

However, there remains a need for novel hole-transport and hole-injection materials for use in OLEDs. In particular, there is a need for materials with which the above-mentioned, highly desired improvements in the performance data and properties of the OLEDs can be achieved.

There is likewise a need for novel matrix materials for use in OLEDs and in other electronic devices. In particular, there is a need for matrix materials for phosphorescent dopants and for matrix materials for mixed-matrix systems which preferably result in good efficiency, a long lifetime and a low operating voltage of the electronic devices.

The present invention is thus based on the object of providing compounds which are suitable for use in electronic devices, such as, for example, OLEDs, and which can be employed, in particular, as hole-transport materials and/or as hole-injection materials and/or as light-emitting materials and/or as matrix materials.

In the context of the present invention, it has surprisingly been found that compounds of the formula (1) indicated below are highly suitable for the above-mentioned uses.

The invention thus relates to a compound of a formula (1)

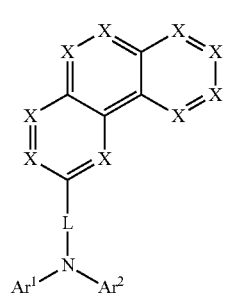

formula (1)

where the following applies to the symbols and indices used:
X is on each occurrence, identically or differently, N and $CR^1$, where a maximum of 2 of the X may be equal to N;

L is a single bond or a divalent aryl or heteroaryl group having 12 to 40 ring atoms, which may be substituted by one or more radicals $R^2$, where, if L is a single bond, the nitrogen is bonded directly to position 3 of the phenanthrene, where L is preferably a single bond;

$Ar^1$, $Ar^2$
is on each occurrence, identically or differently, an aromatic or heteroaromatic ring or an aromatic or heteroaromatic ring system having 5 to 40 aromatic ring atoms, which may be substituted by one or more radicals $R^4$, where, if both $Ar^1$ and also $Ar^2$ are phenyl radicals, at least one $R^4$ on the phenyl radicals is not equal to H and this at least one radical $R^4$ preferably itself contains one or more aromatic or heteroaromatic rings, where it is preferred for both groups $Ar^1$ and $Ar^2$ each to contain at least two aromatic or heteroaromatic rings and where the rings may be bridged within $Ar^1$ and/or the rings may be bridged within $Ar^2$ in such a way that non-aromatic or non-heteroaromatic rings form, where it is very preferred for the rings not to be bridged;

$R^1$ is on each occurrence, identically or differently, H, D, F, Cl, Br, I, C(=O)$R^2$, CN, Si($R^2$)$_3$, NO$_2$, P(=O)($R^2$)$_2$, S(=O)$R^2$, S(=O)$_2R^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more CH$_2$ groups in the above-mentioned groups may be replaced by
—$R^2$C=C$R^2$—, —C≡C—, Si($R^2$)$_2$, C=O, C=S, C=N$R^2$, —C(=O)O—, —C(=O)N$R^2$—, P(=O)($R^2$), —O—, —S—, SO or SO$_2$ and where one or more H atoms in the above-mentioned groups may be replaced by D, F, Cl, Br, I, CN or NO$_2$, or an aromatic ring system having 6 to 30 aromatic ring atoms, which may in each case be substituted by one or more radicals $R^2$, where two or more radicals $R^1$ may be linked to one another and may form a ring;

$R^4$ is on each occurrence, identically or differently, H, D, F, Cl, Br, I, C(=O)$R^2$, CN, Si($R^2$)$_3$, N$R^2$, NO$_2$, P(=O)($R^2$)$_2$, S(=O)$R^2$, S(=O)$_2R^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more CH$_2$ groups in the above-mentioned groups may be replaced by
—$R^2$C=C$R^2$—, —C≡C—, Si($R^2$)$_2$, C=O, C=S, C=N$R^2$, —C(=O)O—, —C(=O)N$R^2$—, P(=O)($R^2$), —O—, —S—, SO or SO$_2$ and where one or more H atoms in the above-mentioned groups may be replaced by D, F, Cl, Br, I, CN or NO$_2$, or an aromatic ring system having 6 to 30 aromatic ring atoms, which may in each case be substituted by one or more radicals $R^2$, where two or more radicals $R^4$ may be linked to one another and may form a ring;

$R^2$ is on each occurrence, identically or differently, H, D, F, Cl, Br, I, C(=O)$R^3$, CN, Si($R^3$)$_3$, NO$_2$, P(=O)($R^3$)$_2$, S(=O)$R^3$, S(=O)$_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=S, C=N$R^3$, —C(=O)O—, —C(=O)N$R^3$—, P(=O)($R^3$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^2$ may be linked to one another and may form a ring;

$R^3$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^3$ here may be linked to one another and may form a ring;

with the proviso that the compound of the formula (1), besides the phenanthrene, contains no further condensed aromatic or heteroaromatic ring having more than 10 ring atoms and with the proviso that the radicals $R^1$ on the phenanthrene in formula (1) contain no further amine groups.

The numbering on the phenanthrene here is defined as follows.

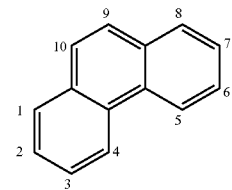

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyl-triazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present description, intended to be taken to mean, inter alia, that the two radicals are linked to one another by a chemical bond. This is illustrated by the following scheme:

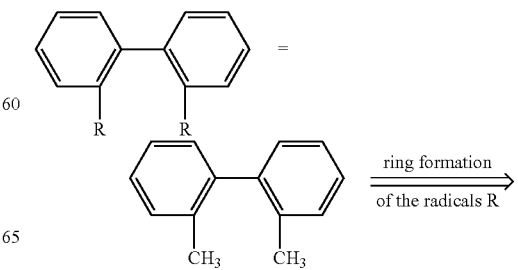

-continued

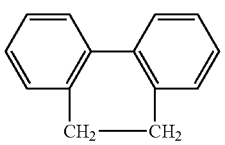
5

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

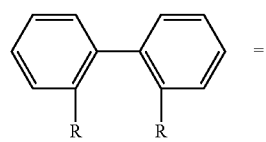

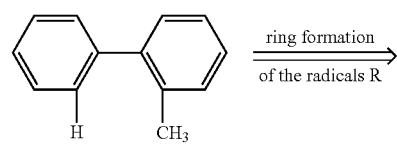

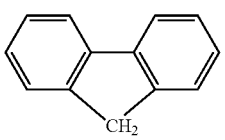

For the purposes of the present invention, preference is given to the compound of the general formula (2)

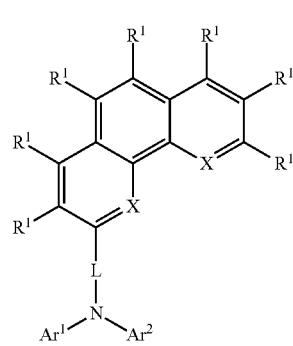

formula (2)

where the above definitions apply to the symbols.

For the purposes of the present invention, great preference is given to a compound of the general formula (3)

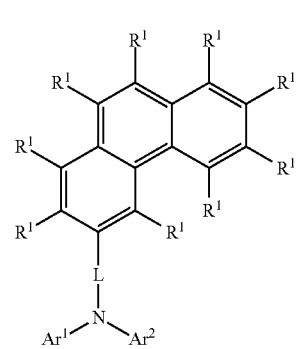

formula (3)

A furthermore preferred embodiment of the present invention is the compound of the general formula (4), where the symbols are defined as indicated above.

formula (4)

For the purposes of the present invention, preference is furthermore given to the compound of the general formula (4a), where the symbols are defined as indicated above and the preferred embodiments mentioned elsewhere also apply to the formula (4a). Thus, for example, in a particularly preferred embodiment of the present invention, L in the compound of the present formula is a single bond and the groups $Ar^1$ and $Ar^2$ very particularly preferably each contain at least two aryl or heteroaryl groups.

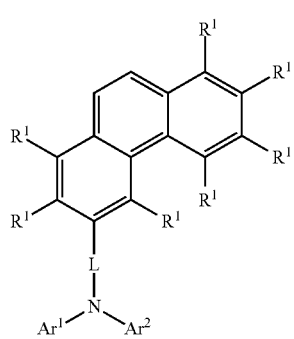

formula (4a)

For the purposes of the present invention, preference is furthermore given to a compound of the general formula (4b)

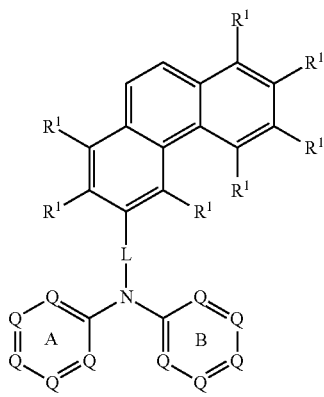

formula (4b)

where

Q is on each occurrence, identically or differently, CR⁴ or N;

and where the above definitions and the preferred embodiments thereof apply to the other symbols.

For the purposes of the present invention, preference is furthermore given to a compound of the general formula (5)

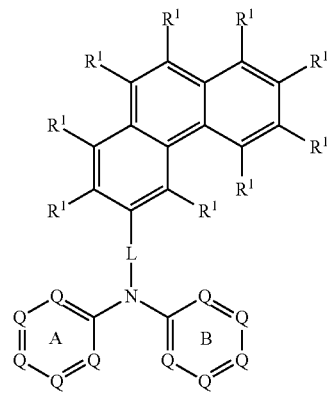

formula (5)

where

Q is on each occurrence, identically or differently, CR⁴ or N;

and where the above definitions and the preferred embodiments thereof apply to the other symbols.

In a very preferred embodiment, the present invention relates to a compound of the general formula (6)

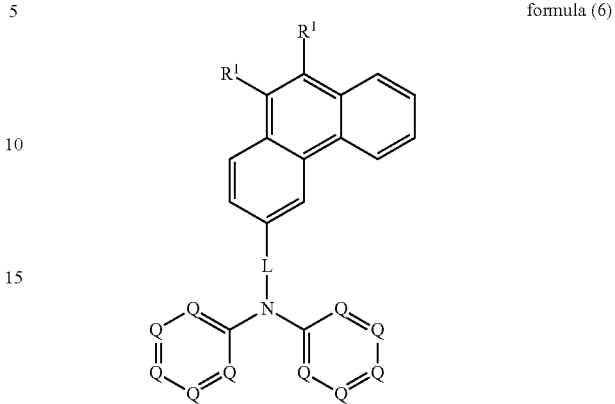

formula (6)

where the above definitions and the preferred embodiments thereof apply to the symbils and indices used.

Particular preference is given to a compound of the general formula (7)

formula (7)

In a further very particularly preferred embodiment of the present invention, at least 4 of the 5 Q in each of the two rings are equal to CR⁴, very particularly preferably all Q are equal to CR⁴.

As already described above, the compound of the formula (1), besides the phenanthrene, contains no further condensed aromatic or heteroaromatic ring having more than 10 ring atoms. Consequently, the substituents Ar¹ and Ar² and the rings A and B do not represent condensed aromatic or heteroaromatic ring systems having more than 10 ring atoms.

It is preferred for at least one of the radicals Ar¹ and Ar² or A and B in formula (1) to contain more than one ring. It is very preferred for both radicals Ar¹ and Ar² or A and B to contain at least 2 or more rings.

For the purposes of the present invention, preference is furthermore given to a compound of the general formula (1), characterised in that it contains in total at least 26, very preferably in total at least 32, very particularly preferably in total at least 38 and especially preferably in total at least 44 ring atoms.

In an especially preferred embodiment of the present invention, the compound of the formula (1) to (7) does not contain an aromatic or heteroaromatic group or an aromatic or heteroaromatic ring system in any of the radicals R¹ bonded directly to the phenanthrene, where it is even more preferred for the compound of the formulae (1) to (7) to contain only one amine group. This results in particularly highly suitable compounds for use in organic electronic and especially in organic electroluminescent devices.

Particularly preferred aromatic and heteroaromatic units as groups $Ar^1$ and $Ar^2$ are represented by the following formulae (8) to (100):

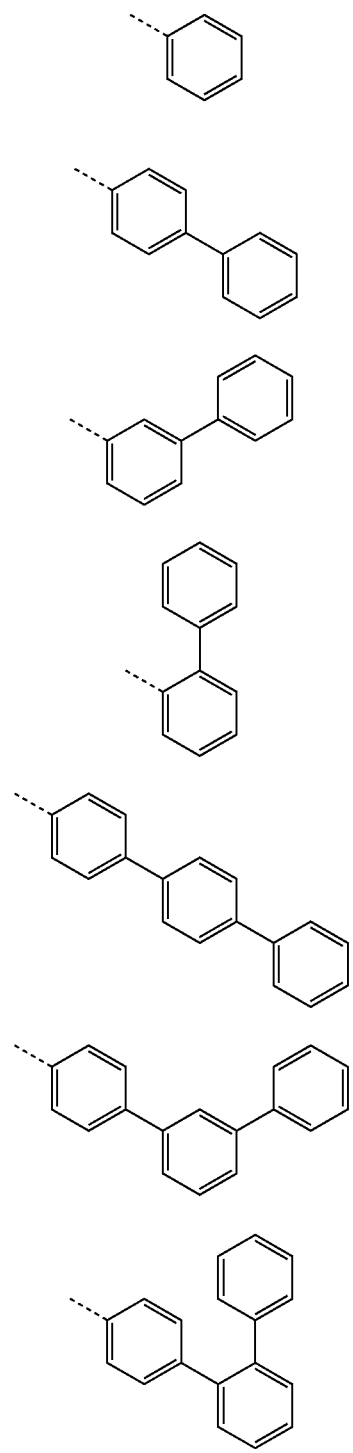

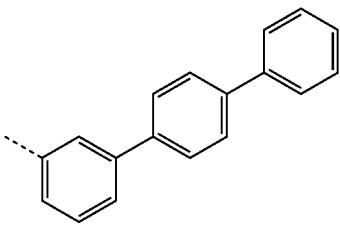

formula (15)

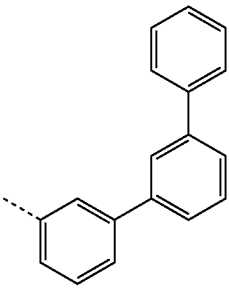

formula (16)

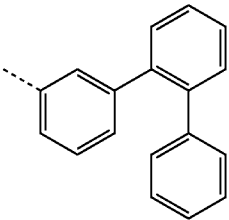

formula (17)

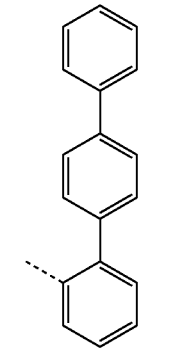

formula (18)

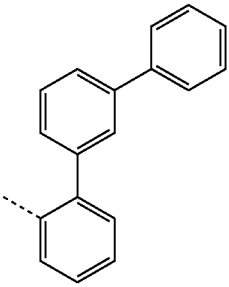

formula (19)

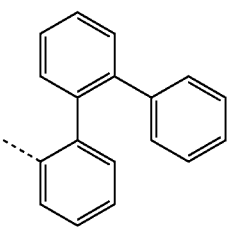

formula (20)

formula (21)
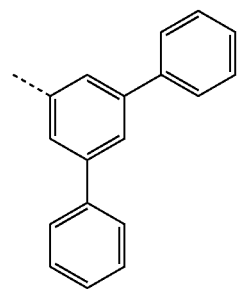
formula (22)
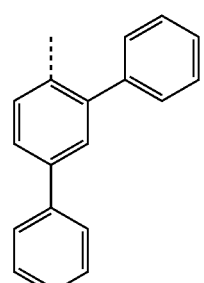
formula (23)
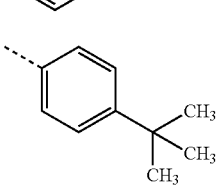
formula (24)
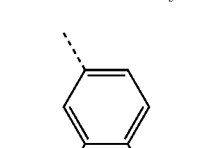
formula (25)
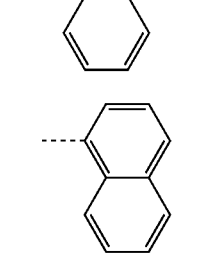
formula (26)
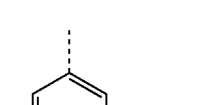
formula (27)
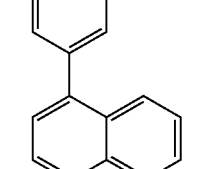
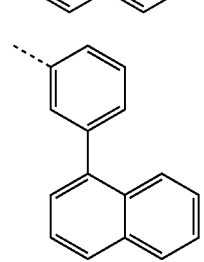
formula (28)
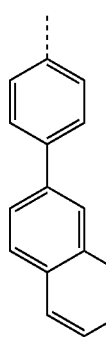
formula (20)
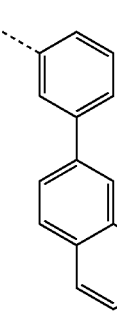
formula (20)
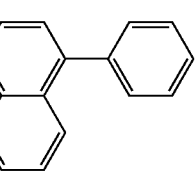
formula (20)
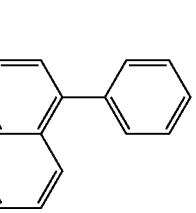
formula (29)
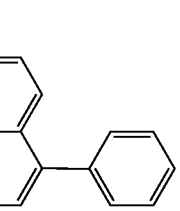
formula (30)
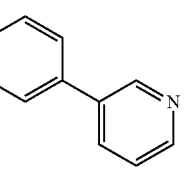
formula (31)
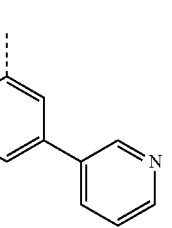

-continued
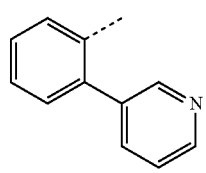
formula (32)
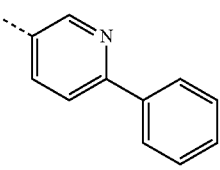
formula (33)
formula (34)
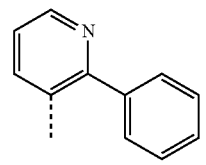
formula (35)
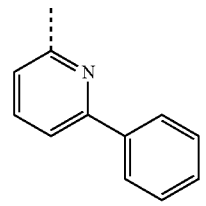
formula (36)
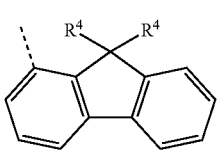
formula (37)
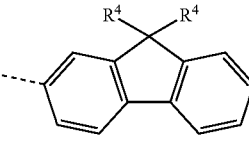
formula (32)
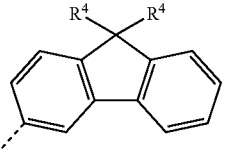
formula (33)
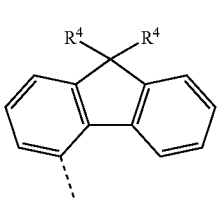
formula (34)
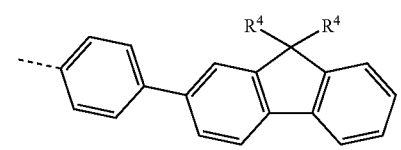
formula (38)
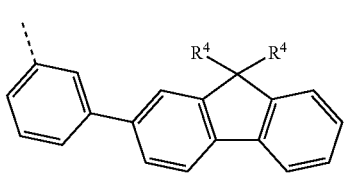
formula (39)
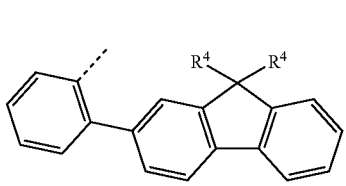
formula (40)
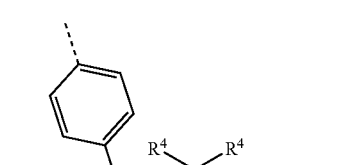
formula (41)
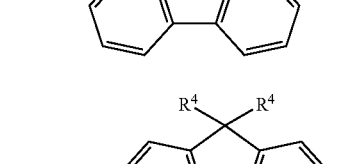
formula (42)
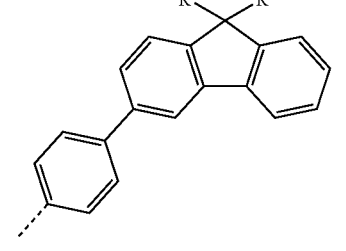
formula (43)
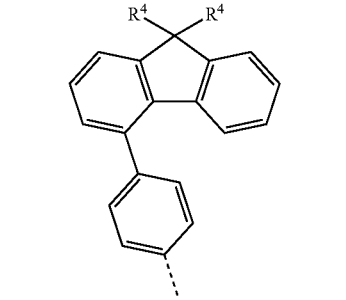
formula (44)
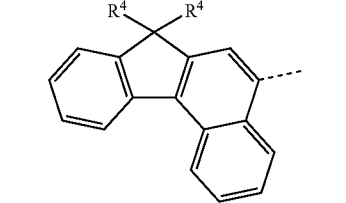

17
-continued
formula (45)
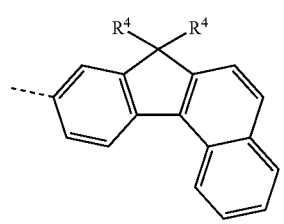
formula (46)
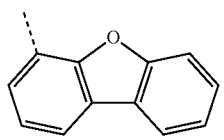
formula (47)
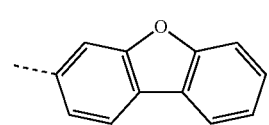
formula (48)
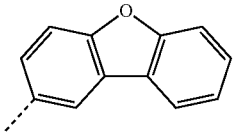
formula (49)
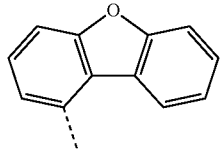
formula (50)
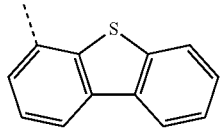
formula (51)
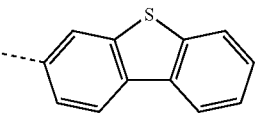
formula (52)
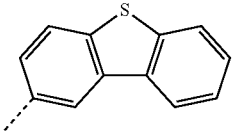
formula (53)
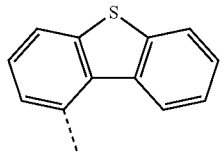
18
-continued
formula (54)
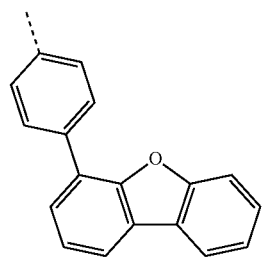
formula (55)
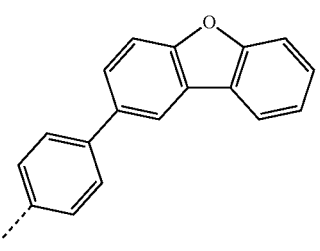
formula (56)
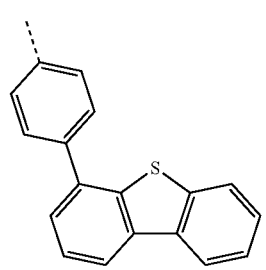
formula (57)
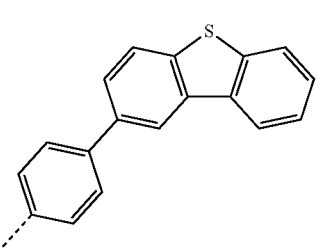
formula (58)
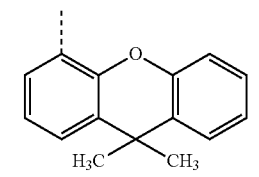
formula (59)
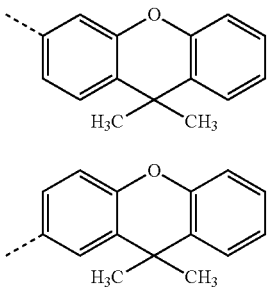
formula (60)

formula (61)
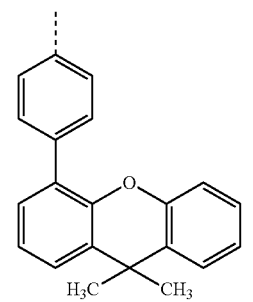
formula (62)
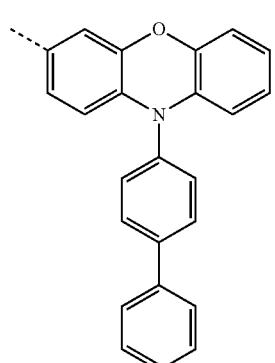
formula (63)
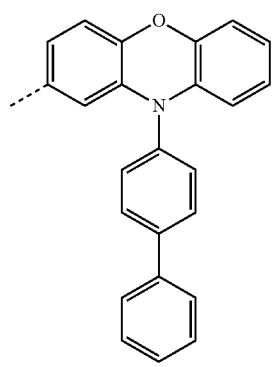
formula (64)
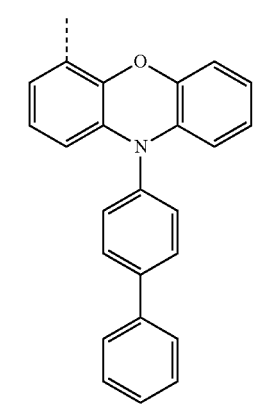
formula (65)
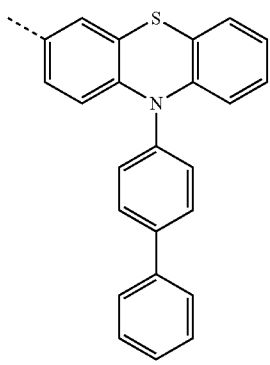
formula (66)
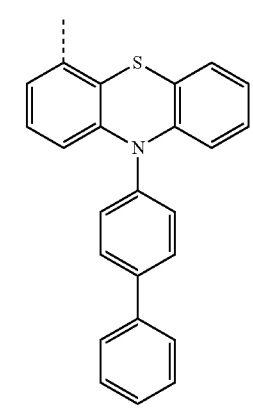
formula (67)
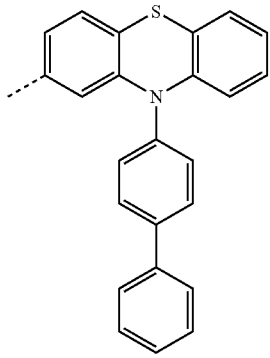
formula (68)
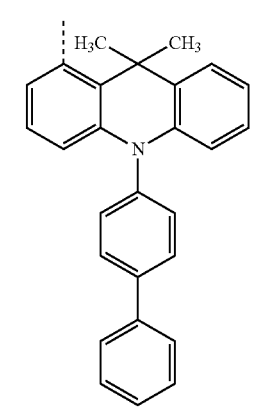

formula (69)
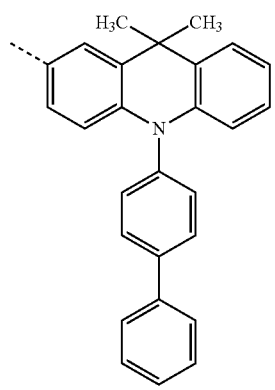
formula (70)
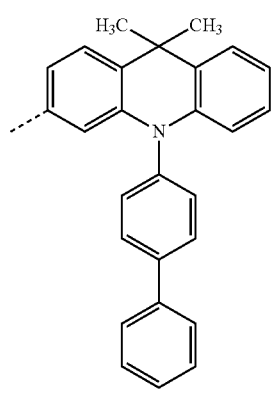
formula (71)
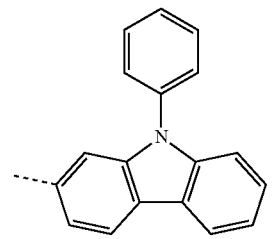
formula (72)
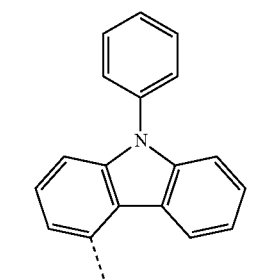
formula (73)
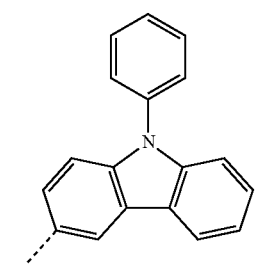
formula (74)
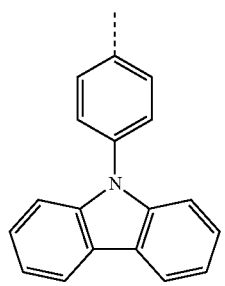
formula (75)
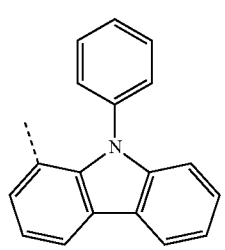
formula (76)
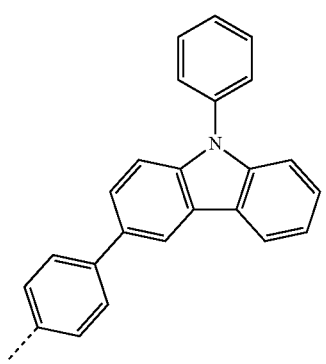
formula (77)
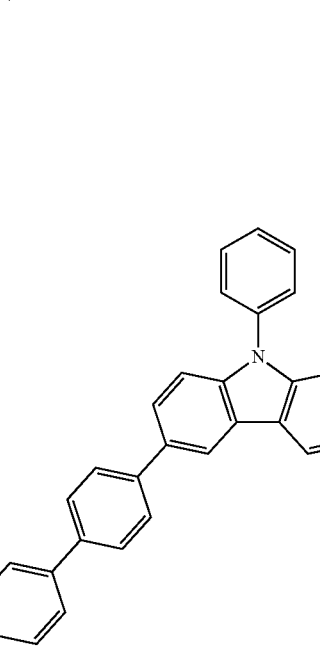

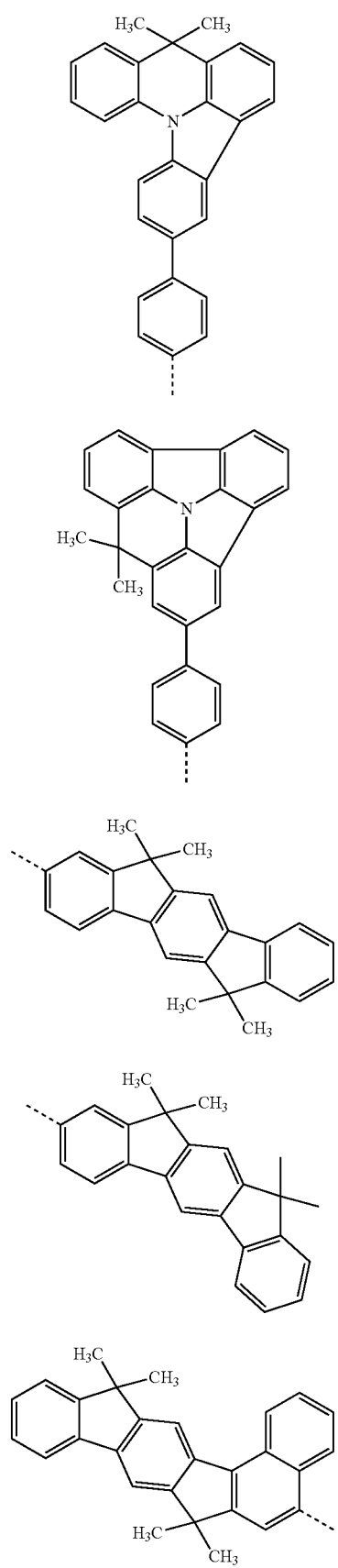
formula (78)
formula (79)
formula (80)
formula (81)
formula (82)
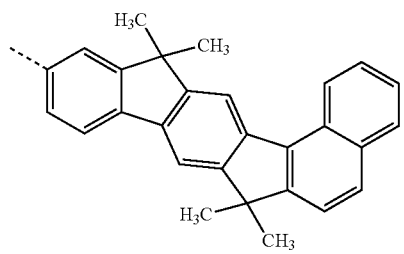
formula (83)
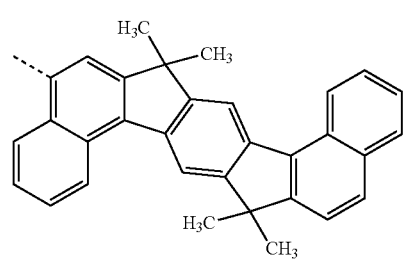
formula (84)
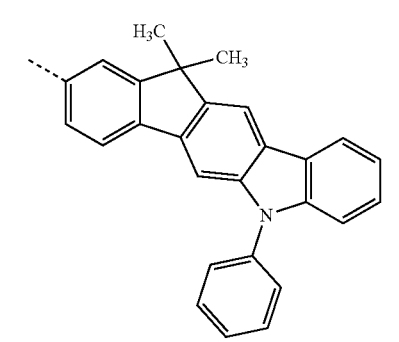
formula (85)
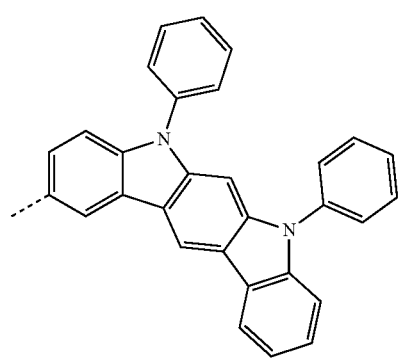
formula (86)
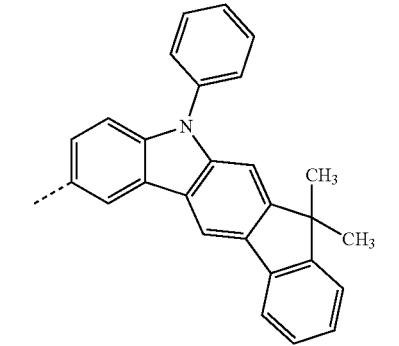
formula (87)

formula (88)
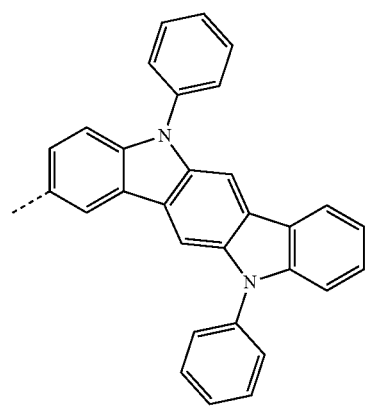
formula (89)
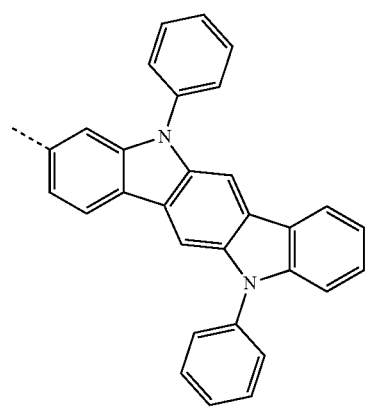
formula (90)
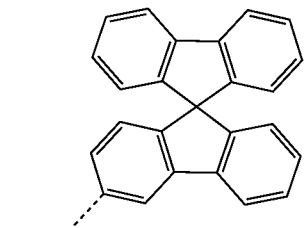
formula (91)
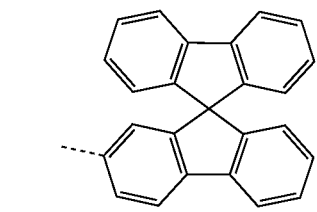
formula (92)
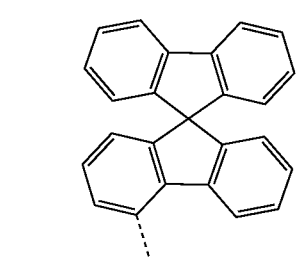
formula (93)
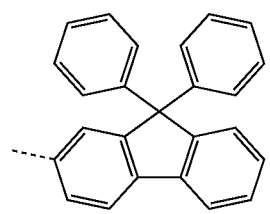
formula (94)
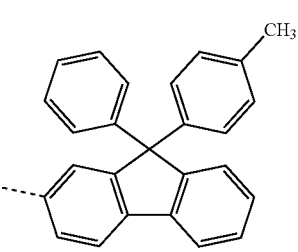
formula (95)
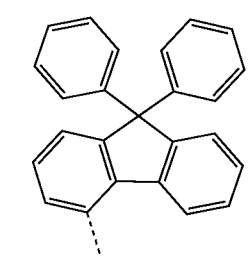
formula (96)
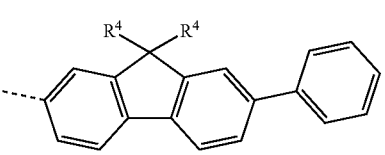
formula (97)
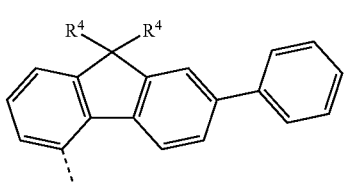
formula (98)
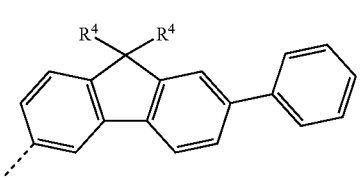
formula (99)
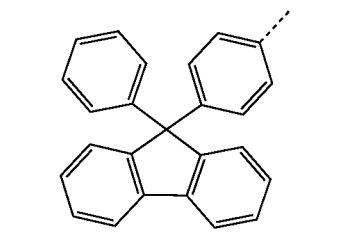

formula (100)

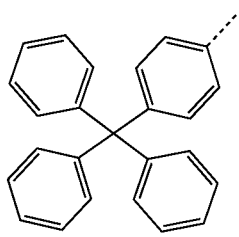

where the dashed line represents the bonding position and where the structures may be substituted by one or more radicals $R^4$, and $R^4$ is defined as indicated above.

In a preferred embodiment, L is an aromatic ring system selected from the group consisting of biphenylenes, terphenylenes and the compounds of the following formula (101a) and (101b)

formula (101a)

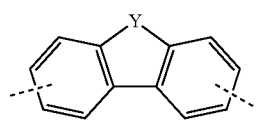

formula (101b)

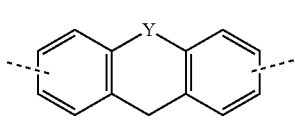

where Y is equal to $C(R^2)_2$, $NR^2$, O, $Si(R^2)_2$ and S, preferably $C(R^2)_2$, $NR^2$, O and S, very preferably $C(R^2)_2$, $NR^2$ and O and especially preferably $C(R^2)_2$ and $NR^2$, and where $R^2$ is defined as indicated above.

In a very preferred embodiment, L is a single bond, i.e. the nitrogen atom is bonded directly to the phenanthrene in position 3 via a single bond.

In an especially preferred embodiment, the present inventions relates to a compound of the formula (1), characterised in that it contains only one amine group, so that the compounds of the formula (1) are consequently monoamines.

Examples of compounds according to the invention are depicted in the following table.

formula (102)

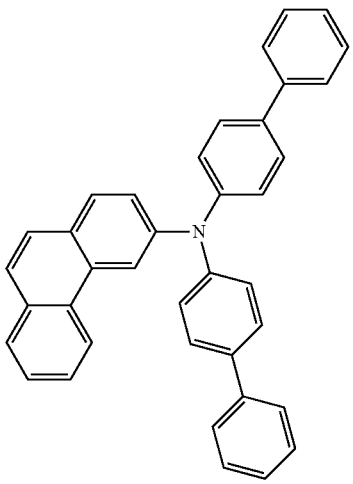 [SMILES: c1ccc(-c2ccc(N(c3ccc(-c4ccccc4)cc3)c3ccc4ccc5ccccc5c4c3)cc2)cc1]

formula (103)

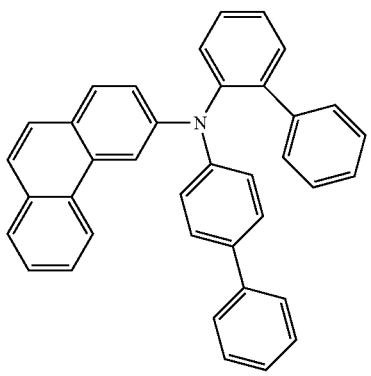 [SMILES: c1ccc(-c2ccc(N(c3ccc4ccc5ccccc5c4c3)c3ccccc3-c3ccccc3)cc2)cc1]

-continued
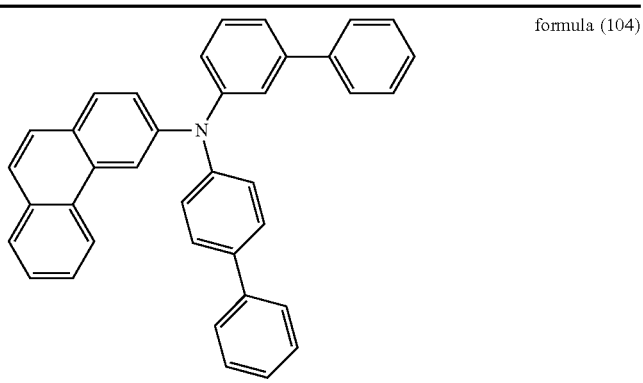
formula (104)
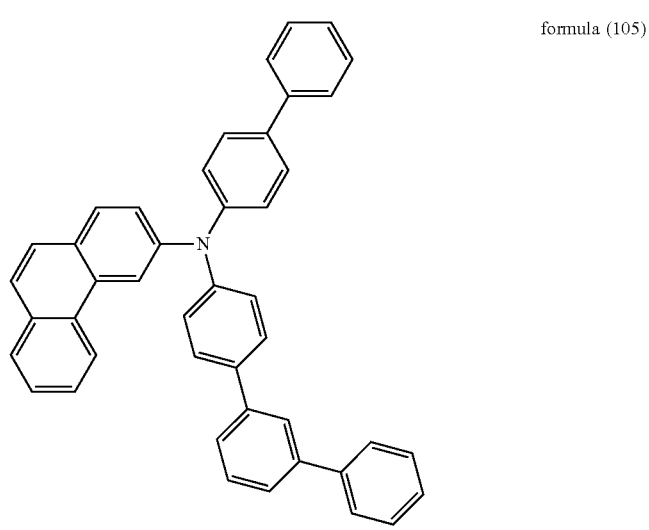
formula (105)
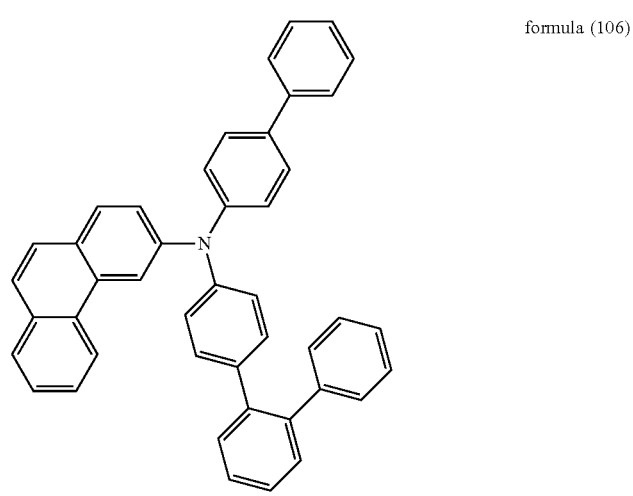
formula (106)

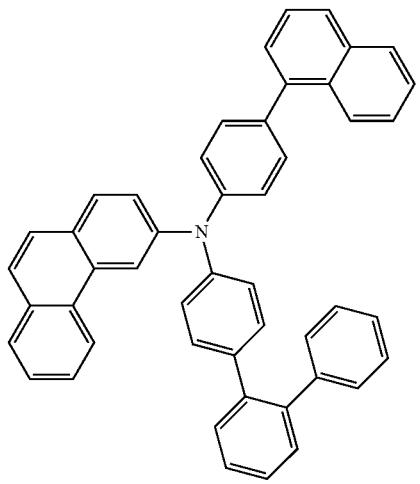 [SMILES: c1ccc(-c2ccccc2-c2ccc(N(c3ccc(-c4cccc5ccccc45)cc3)c3ccc4ccc5ccccc5c4c3)cc2)cc1]
formula (107)
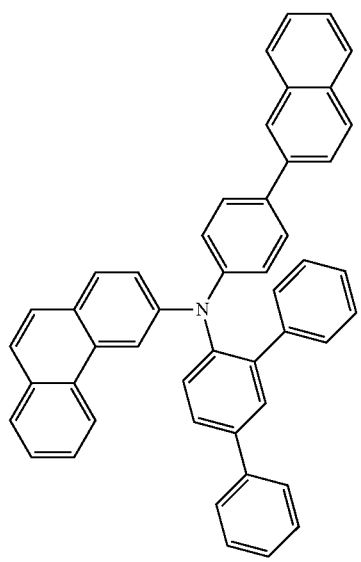 [SMILES: c1ccc(-c2ccc(N(c3ccc(-c4ccc5ccccc5c4)cc3)c3ccc4ccc5ccccc5c4c3)c(-c3ccccc3)c2)cc1]
formula (108)
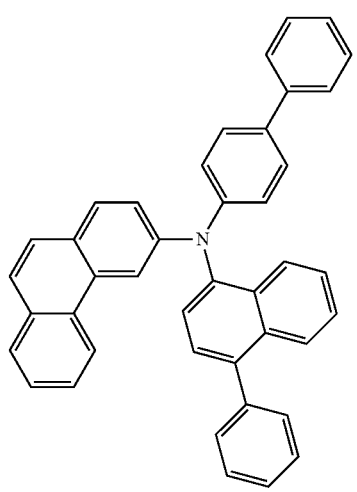 [SMILES: c1ccc(-c2ccc(N(c3ccc4ccc5ccccc5c4c3)c3ccc(-c4ccccc4)c4ccccc34)cc2)cc1]
formula (109)

-continued
formula (110)
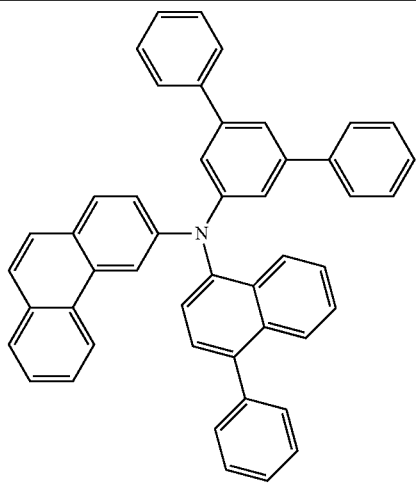
formula (111)
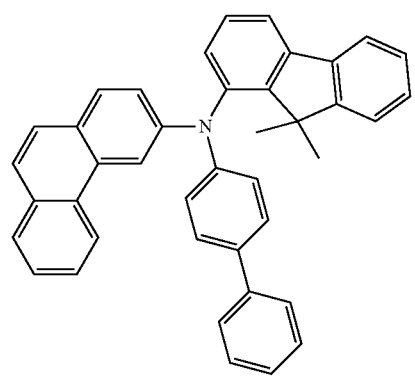 [SMILES: CC1(C)c2ccccc2-c2cccc(N(c3ccc(-c4ccccc4)cc3)c3ccc4ccc5ccccc5c4c3)c21]
formula (112)
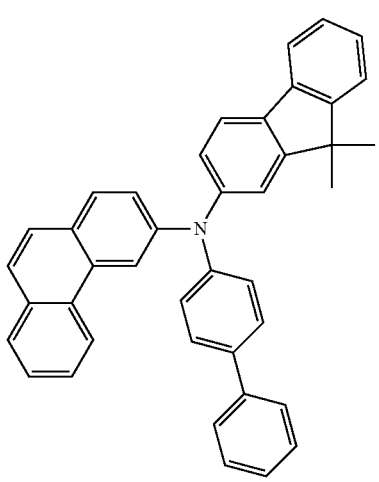 [SMILES: CC1(C)c2ccccc2-c2ccc(N(c3ccc(-c4ccccc4)cc3)c3ccc4ccc5ccccc5c4c3)cc21]

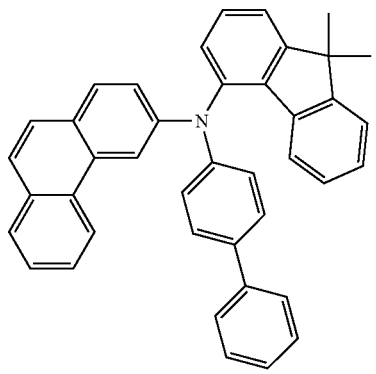 [SMILES: CC1(C)c2ccccc2-c2c(N(c3ccc(-c4ccccc4)cc3)c3ccc4ccc5ccccc5c4c3)cccc21]
formula (113)
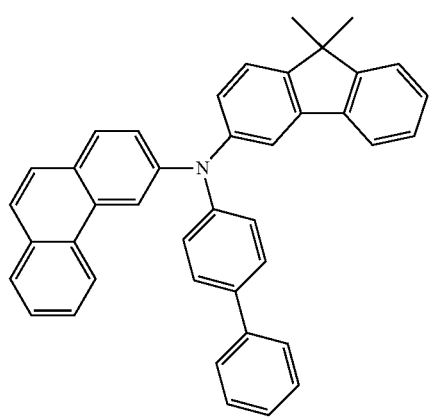 [SMILES: CC1(C)c2ccccc2-c2cc(N(c3ccc(-c4ccccc4)cc3)c3ccc4ccc5ccccc5c4c3)ccc21]
formula (114)
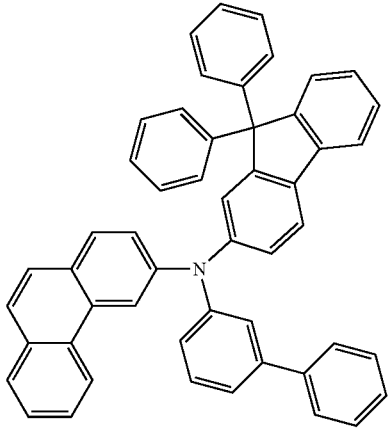 [SMILES: c1ccc(-c2cccc(N(c3ccc4c(c3)C(c3ccccc3)(c3ccccc3)c3ccccc3-4)c3ccc4ccc5ccccc5c4c3)c2)cc1]
formula (115)
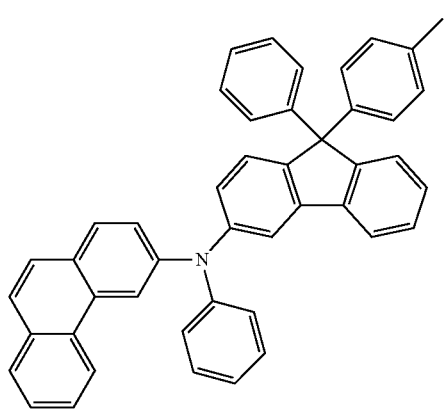 [SMILES: Cc1ccc(C2(c3ccccc3)c3ccccc3-c3cc(N(c4ccccc4)c4ccc5ccc6ccccc6c5c4)ccc32)cc1]
formula (116)

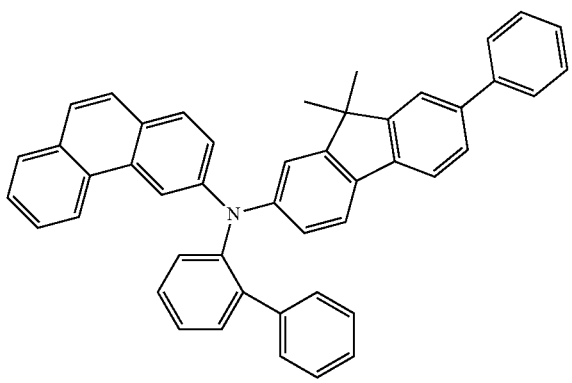 [SMILES: CC1(C)c2cc(-c3ccccc3)ccc2-c2ccc(N(c3ccc4ccc5ccccc5c4c3)c3ccccc3-c3ccccc3)cc21]
formula (117)
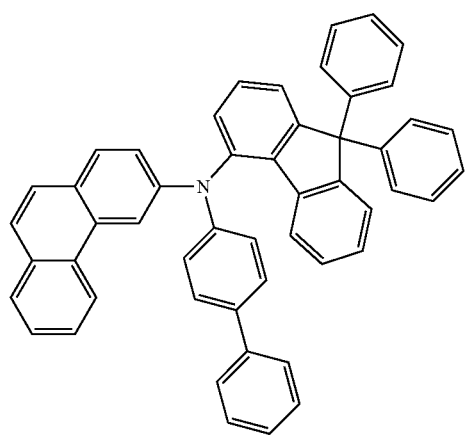 [SMILES: c1ccc(-c2ccc(N(c3ccc4ccc5ccccc5c4c3)c3cccc4c3-c3ccccc3C4(c3ccccc3)c3ccccc3)cc2)cc1]
formula (118)
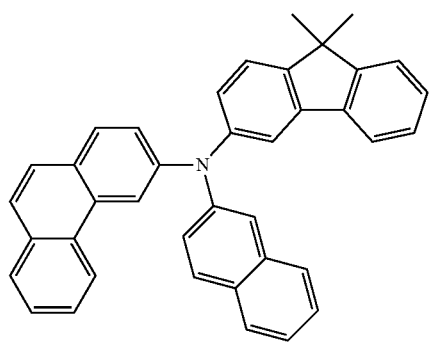 [SMILES: CC1(C)c2ccccc2-c2cc(N(c3ccc4ccccc4c3)c3ccc4ccc5ccccc5c4c3)ccc21]
formula (119)
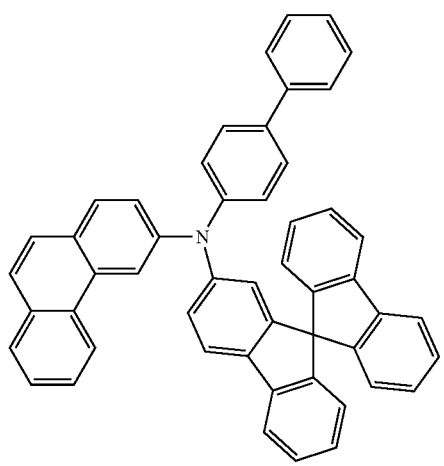 [SMILES: c1ccc(-c2ccc(N(c3ccc4c(c3)C3(c5ccccc5-c5ccccc53)c3ccccc3-4)c3ccc4ccc5ccccc5c4c3)cc2)cc1]
formula (120)

formula (121)
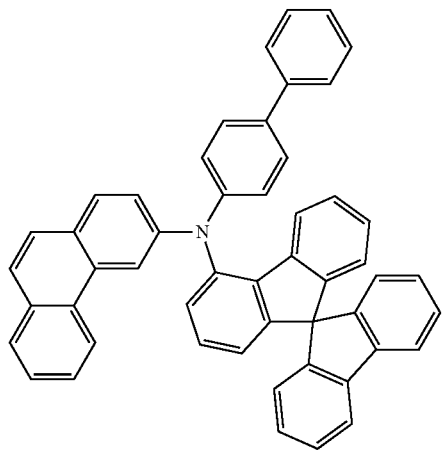 [SMILES: c1ccc(-c2ccc(N(c3ccc4ccc5ccccc5c4c3)c3cccc4c3-c3ccccc3C43c4ccccc4-c4ccccc43)cc2)cc1]
formula (122)
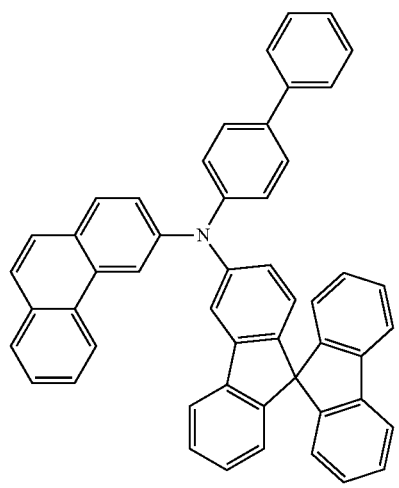 [SMILES: c1ccc(-c2ccc(N(c3ccc4c(c3)-c3ccccc3C43c4ccccc4-c4ccccc43)c3ccc4ccc5ccccc5c4c3)cc2)cc1]
formula (123)
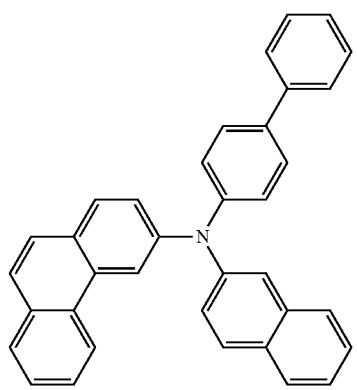 [SMILES: c1ccc(-c2ccc(N(c3ccc4ccccc4c3)c3ccc4ccc5ccccc5c4c3)cc2)cc1]

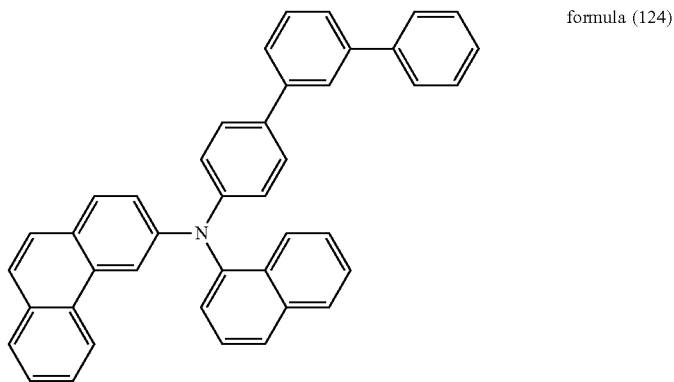
formula (124)
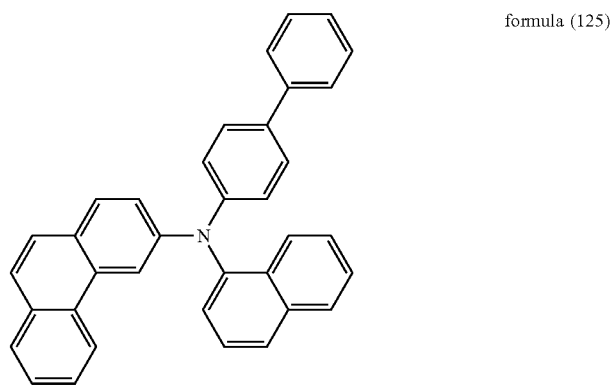
formula (125)
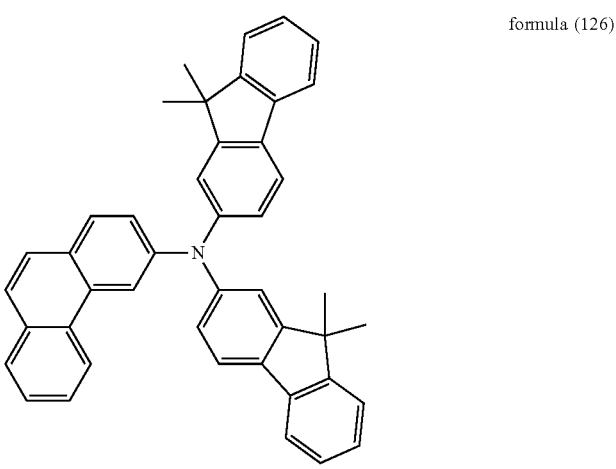
formula (126)
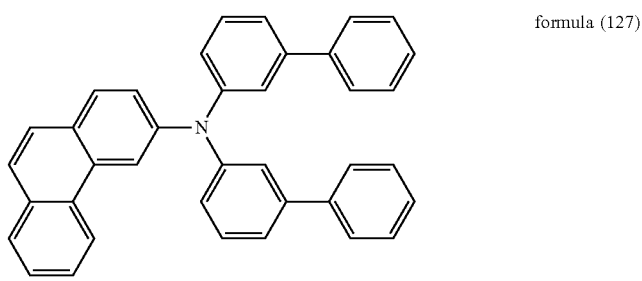
formula (127)

-continued
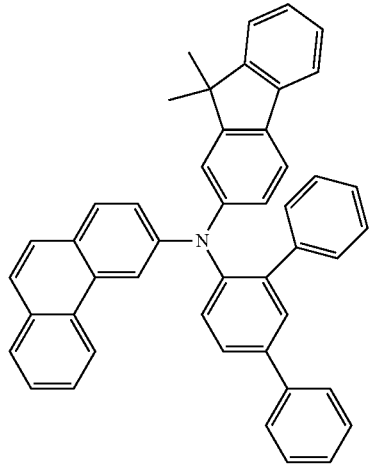 [SMILES: CC1(C)c2ccccc2-c2ccc(N(c3ccc4ccc5ccccc5c4c3)c3ccc(-c4ccccc4)cc3-c3ccccc3)cc21]
formula (128)
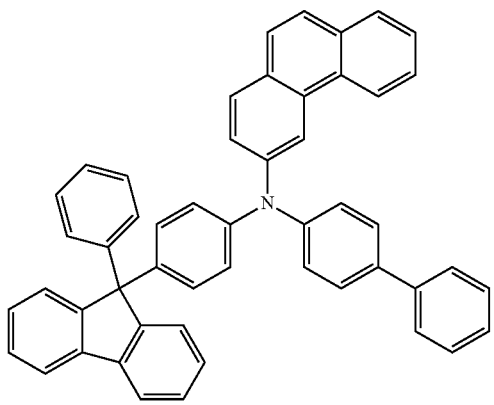 [SMILES: c1ccc(-c2ccc(N(c3ccc(C4(c5ccccc5)c5ccccc5-c5ccccc54)cc3)c3ccc4ccc5ccccc5c4c3)cc2)cc1]
formula (129)
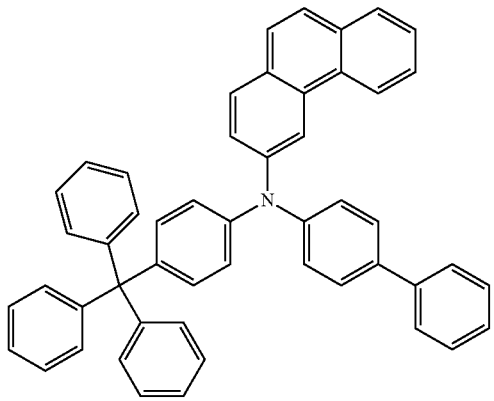 [SMILES: c1ccc(-c2ccc(N(c3ccc(C(c4ccccc4)(c4ccccc4)c4ccccc4)cc3)c3ccc4ccc5ccccc5c4c3)cc2)cc1]
formula (130)
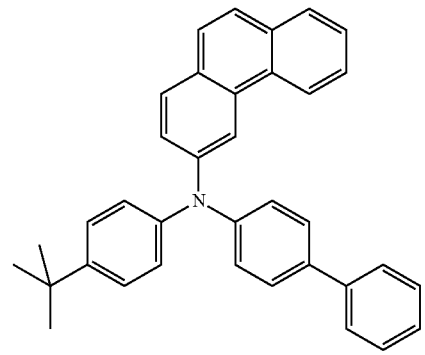 [SMILES: CC(C)(C)c1ccc(N(c2ccc(-c3ccccc3)cc2)c2ccc3ccc4ccccc4c3c2)cc1]
formula (131)

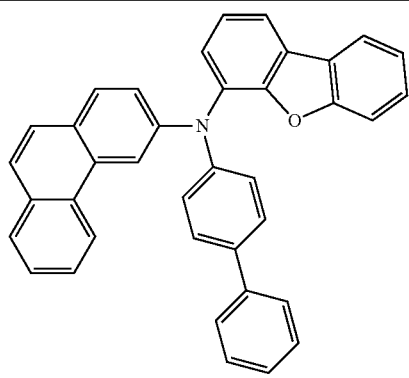
formula (132)
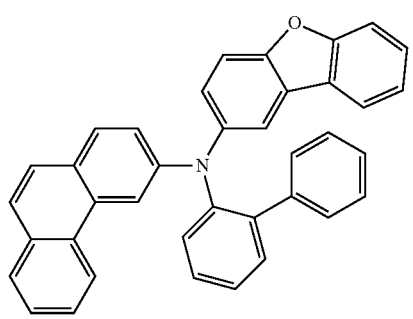
formula (133)
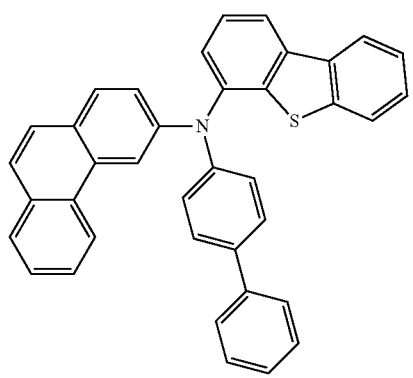 [SMILES: c1ccc(-c2ccc(N(c3ccc4ccc5ccccc5c4c3)c3cccc4c3oc3ccccc34)cc2)cc1]
formula (134)
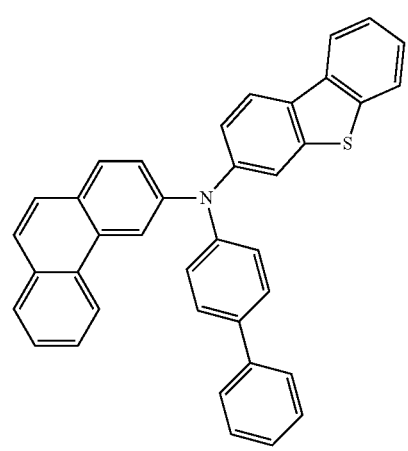 [SMILES: c1ccc(-c2ccc(N(c3ccc4c(c3)sc3ccccc34)c3ccc4ccc5ccccc5c4c3)cc2)cc1]
formula (135)

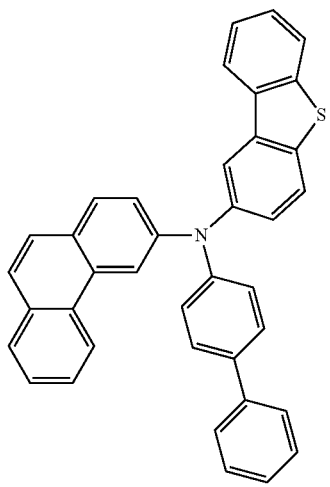 [SMILES: c1ccc(-c2ccc(N(c3ccc4ccc5ccccc5c4c3)c3ccc4sc5ccccc5c4c3)cc2)cc1]
formula (136)
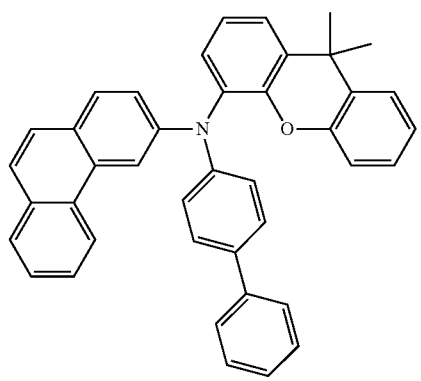 [SMILES: CC1(C)c2ccccc2Oc2c(N(c3ccc(-c4ccccc4)cc3)c3ccc4ccc5ccccc5c4c3)cccc21]
formula (137)
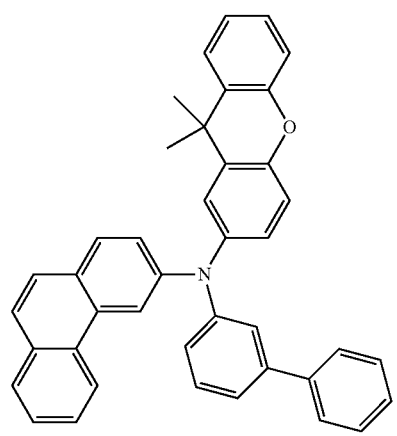 [SMILES: CC1(C)c2ccccc2Oc2ccc(N(c3cccc(-c4ccccc4)c3)c3ccc4ccc5ccccc5c4c3)cc21]
formula (138)

-continued
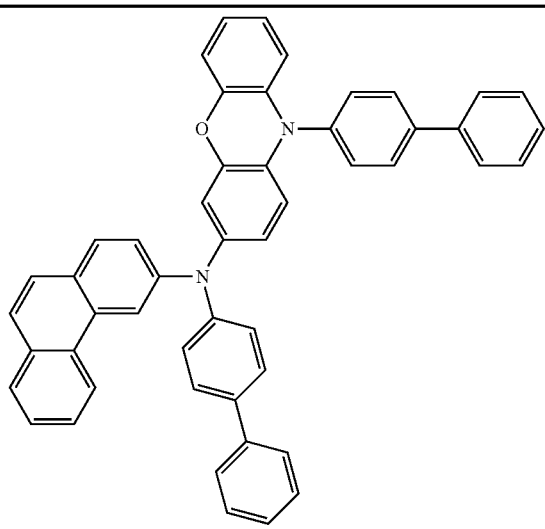
formula (139)
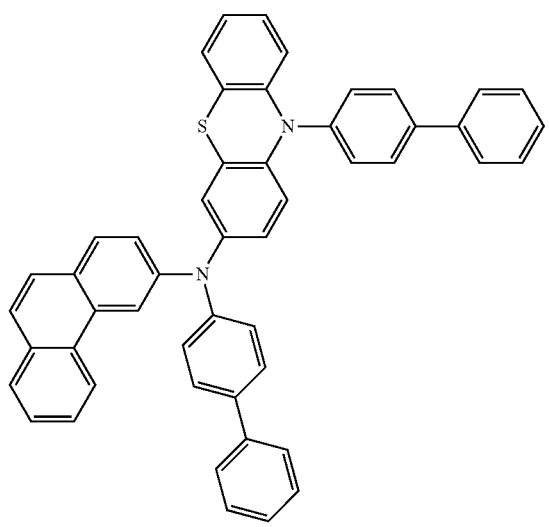 [SMILES: c1ccc(-c2ccc(N(c3ccc4c(c3)Sc3ccccc3N4c3ccc(-c4ccccc4)cc3)c3ccc4ccc5ccccc5c4c3)cc2)cc1]
formula (140)
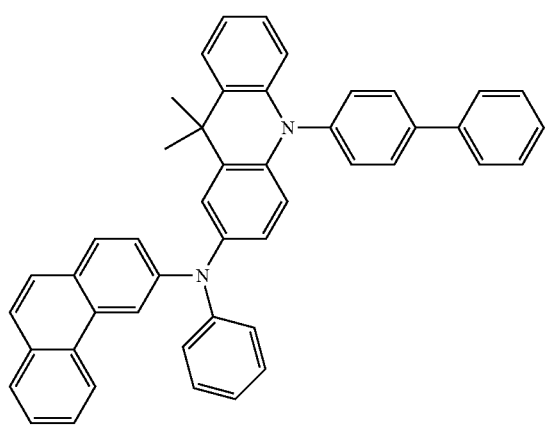 [SMILES: CC1(C)c2ccccc2N(c2ccc(-c3ccccc3)cc2)c2ccc(N(c3ccccc3)c3ccc4ccc5ccccc5c4c3)cc21]
formula (141)

formula (142)
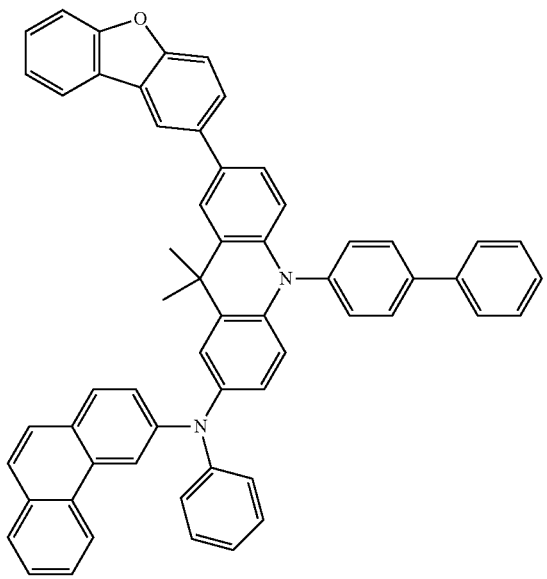 [SMILES: CC1(C)c2cc(-c3ccc4oc5ccccc5c4c3)ccc2N(c2ccc(-c3ccccc3)cc2)c2ccc(N(c3ccccc3)c3ccc4ccc5ccccc5c4c3)cc21]
formula (143)
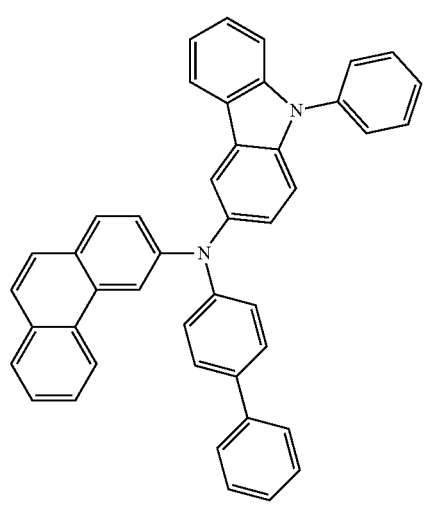 [SMILES: c1ccc(-c2ccc(N(c3ccc4ccc5ccccc5c4c3)c3ccc4c(c3)c3ccccc3n4-c3ccccc3)cc2)cc1]
formula (144)
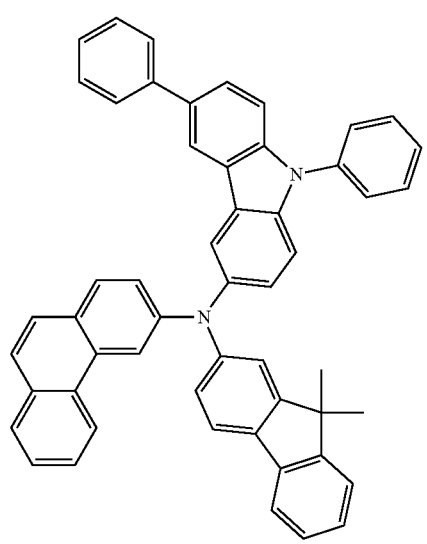 [SMILES: CC1(C)c2ccccc2-c2ccc(N(c3ccc4ccc5ccccc5c4c3)c3ccc4c(c3)c3cc(-c5ccccc5)ccc3n4-c3ccccc3)cc21]

formula (145)
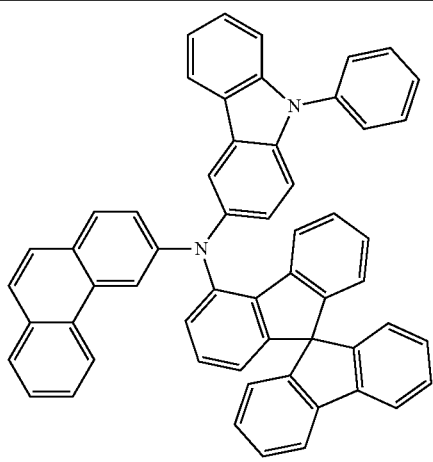
formula (146)
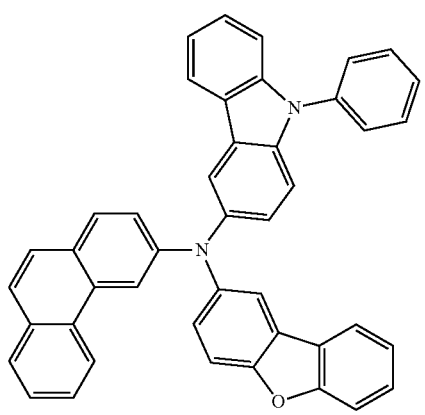 [SMILES: c1ccc(-n2c3ccccc3c3cc(N(c4ccc5ccc6ccccc6c5c4)c4ccc5oc6ccccc6c5c4)ccc32)cc1]
formula (147)
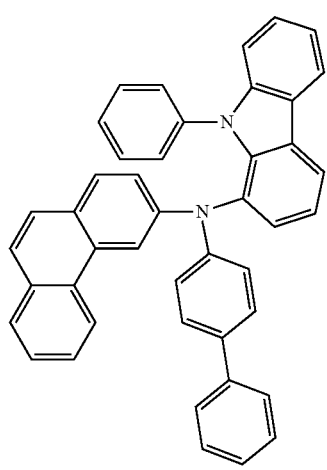 [SMILES: c1ccc(-c2ccc(N(c3ccc4ccc5ccccc5c4c3)c3cccc4c5ccccc5n(-c5ccccc5)c34)cc2)cc1]

-continued
formula (148)
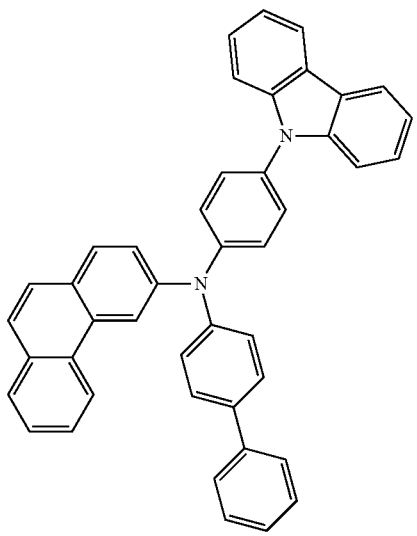 [SMILES: c1ccc(-c2ccc(N(c3ccc(-n4c5ccccc5c5ccccc54)cc3)c3ccc4ccc5ccccc5c4c3)cc2)cc1]
formula (149)
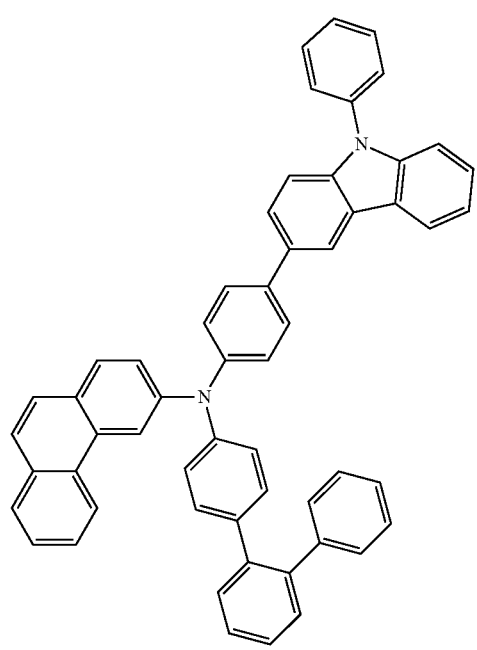 [SMILES: c1ccc(-c2ccccc2-c2ccc(N(c3ccc(-c4ccc5c(c4)c4ccccc4n5-c4ccccc4)cc3)c3ccc4ccc5ccccc5c4c3)cc2)cc1]

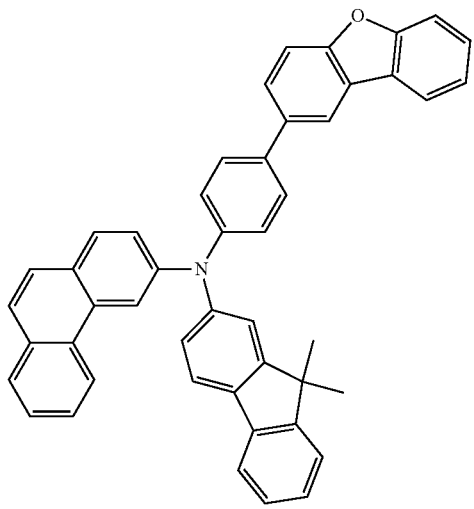 [SMILES: CC1(C)c2ccccc2-c2ccc(N(c3ccc(-c4ccc5oc6ccccc6c5c4)cc3)c3ccc4ccc5ccccc5c4c3)cc21]
formula (150)
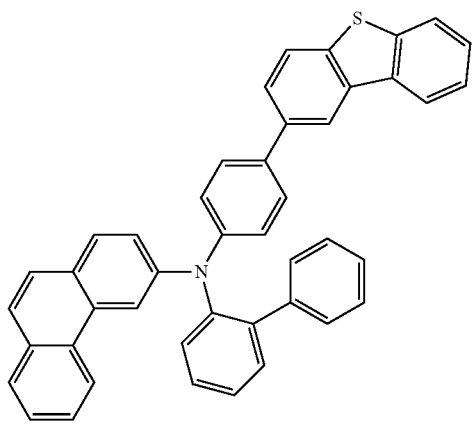 [SMILES: c1ccc(-c2ccccc2N(c2ccc(-c3ccc4sc5ccccc5c4c3)cc2)c2ccc3ccc4ccccc4c3c2)cc1]
formula (151)
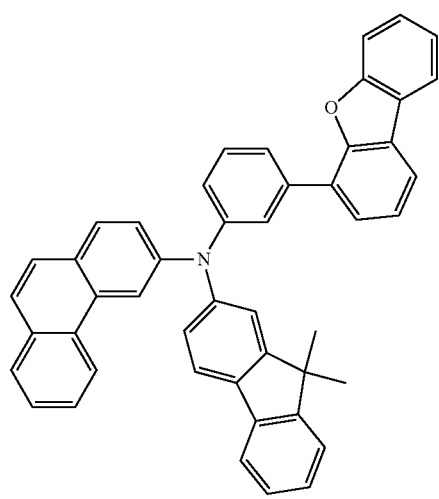 [SMILES: CC1(C)c2ccccc2-c2ccc(N(c3cccc(-c4cccc5c4oc4ccccc45)c3)c3ccc4ccc5ccccc5c4c3)cc21]
formula (152)

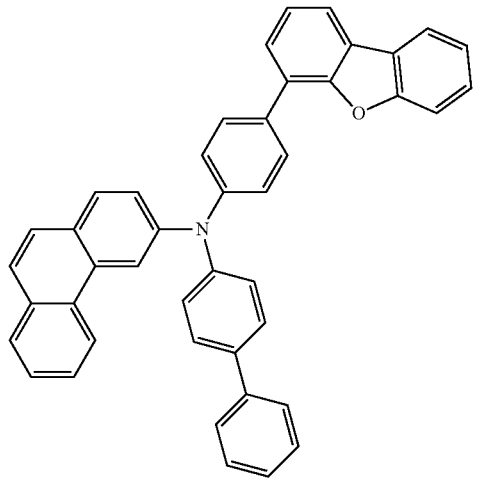 [SMILES: c1ccc(-c2ccc(N(c3ccc(-c4cccc5c4oc4ccccc45)cc3)c3ccc4ccc5ccccc5c4c3)cc2)cc1]
formula (153)
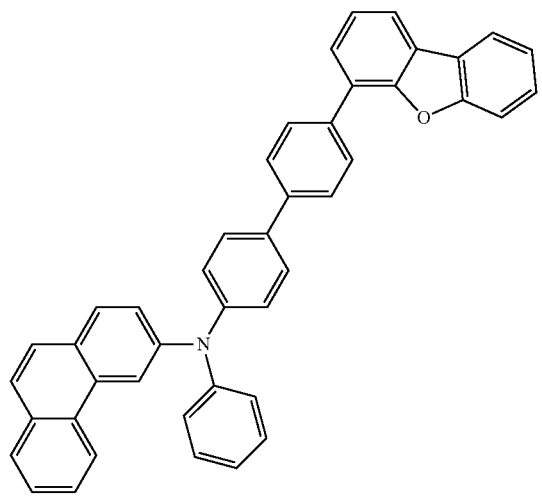 [SMILES: c1ccc(N(c2ccc(-c3ccc(-c4cccc5c4oc4ccccc45)cc3)cc2)c2ccc3ccc4ccccc4c3c2)cc1]
formula (154)
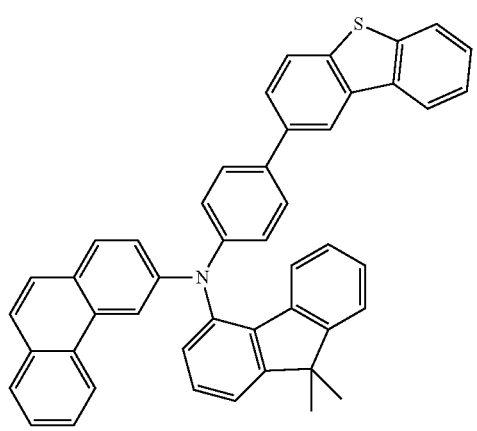 [SMILES: CC1(C)c2ccccc2-c2c(N(c3ccc(-c4ccc5sc6ccccc6c5c4)cc3)c3ccc4ccc5ccccc5c4c3)cccc21]
formula (155)

-continued
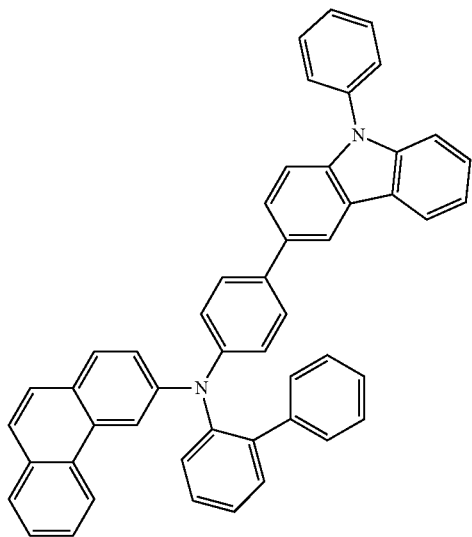 [SMILES: c1ccc(-c2ccccc2N(c2ccc(-c3ccc4c(c3)c3ccccc3n4-c3ccccc3)cc2)c2ccc3ccc4ccccc4c3c2)cc1]
formula (156)
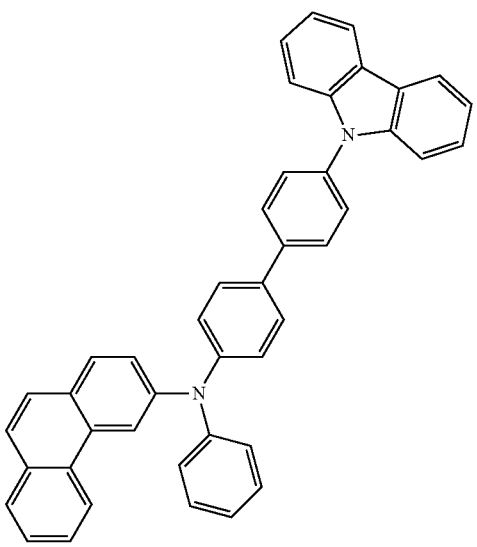 [SMILES: c1ccc(N(c2ccc(-c3ccc(-n4c5ccccc5c5ccccc54)cc3)cc2)c2ccc3ccc4ccccc4c3c2)cc1]
formula (157)
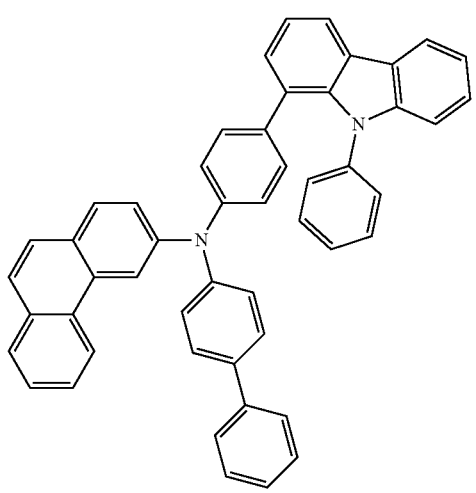 [SMILES: c1ccc(-c2ccc(N(c3ccc(-c4cccc5c6ccccc6n(-c6ccccc6)c45)cc3)c3ccc4ccc5ccccc5c4c3)cc2)cc1]
formula (158)

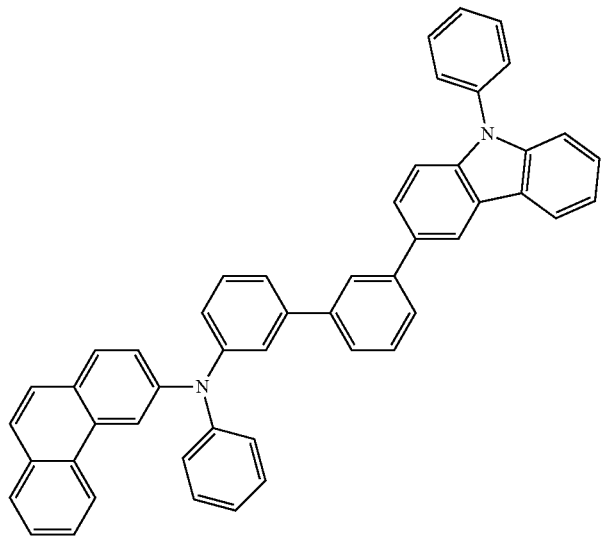 [SMILES: c1ccc(N(c2cccc(-c3cccc(-c4ccc5c(c4)c4ccccc4n5-c4ccccc4)c3)c2)c2ccc3ccc4ccccc4c3c2)cc1]
formula (159)
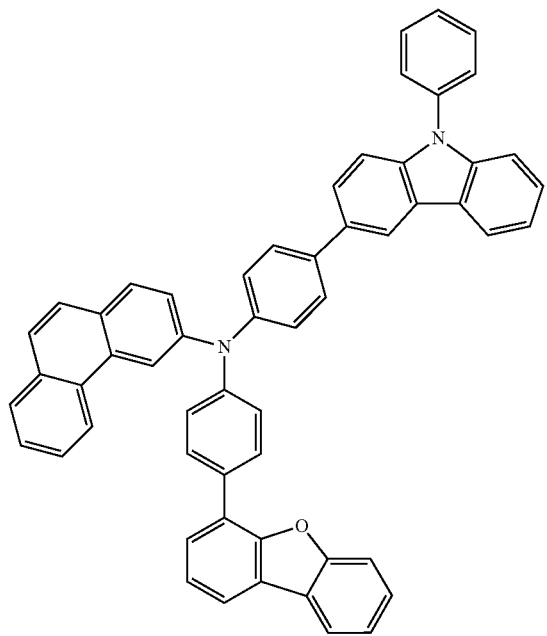 [SMILES: c1ccc(-n2c3ccccc3c3cc(-c4ccc(N(c5ccc(-c6cccc7c6oc6ccccc67)cc5)c5ccc6ccc7ccccc7c6c5)cc4)ccc32)cc1]
formula (160)

-continued
formula (161)
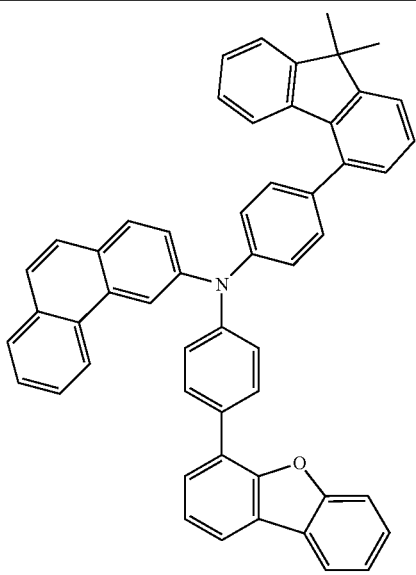
formula (162)
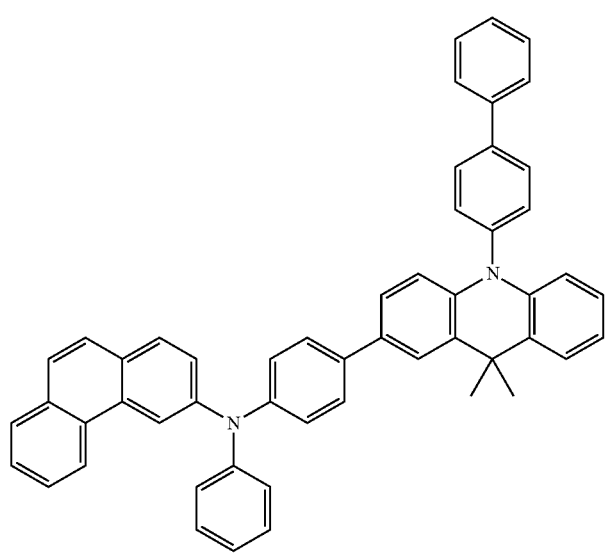 [SMILES: CC1(C)c2ccccc2N(c2ccc(-c3ccccc3)cc2)c2ccc(-c3ccc(N(c4ccccc4)c4ccc5ccc6ccccc6c5c4)cc3)cc21]
formula (163)
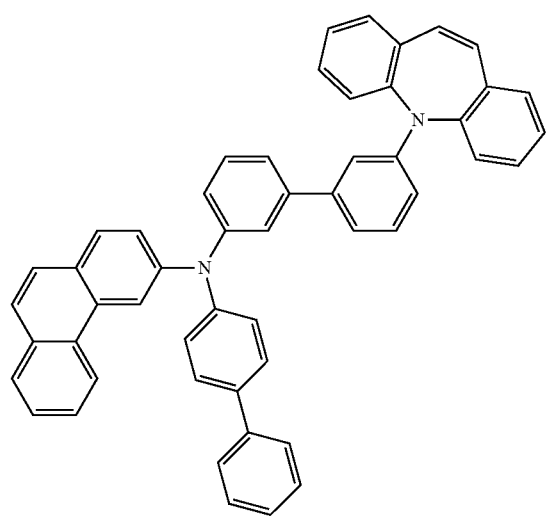 [SMILES: C1=Cc2ccccc2N(c2cccc(-c3cccc(N(c4ccc(-c5ccccc5)cc4)c4ccc5ccc6ccccc6c5c4)c3)c2)c2ccccc21]

formula (164)
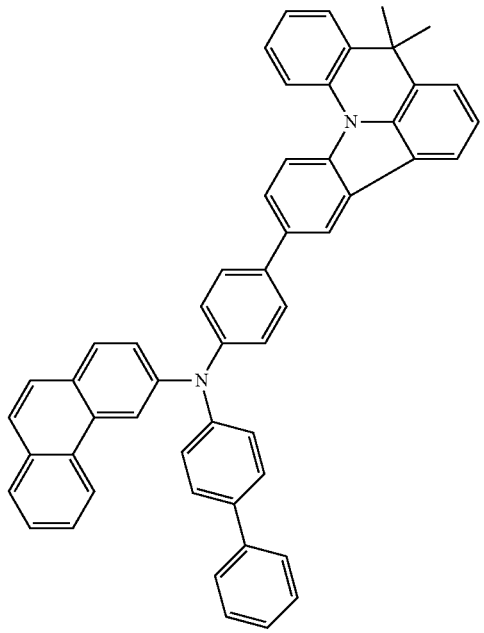 [SMILES: CC1(C)c2ccccc2-n2c3ccc(-c4ccc(N(c5ccc(-c6ccccc6)cc5)c5ccc6ccc7ccccc7c6c5)cc4)cc3c3cccc1c32]
formula (165)
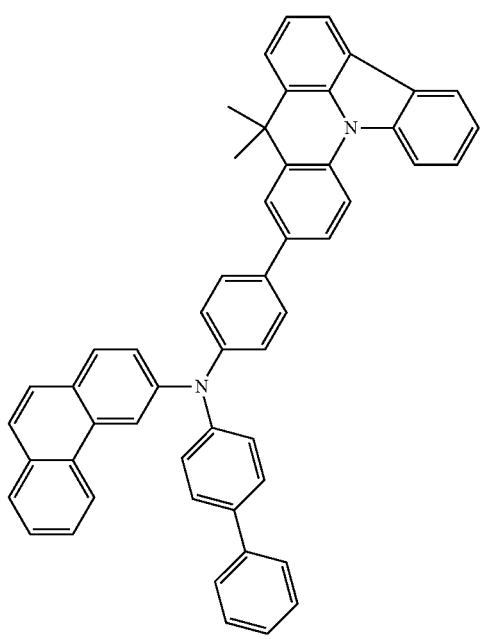 [SMILES: CC1(C)c2cc(-c3ccc(N(c4ccc(-c5ccccc5)cc4)c4ccc5ccc6ccccc6c5c4)cc3)ccc2-n2c3ccccc3c3cccc1c32]

-continued
formula (166)
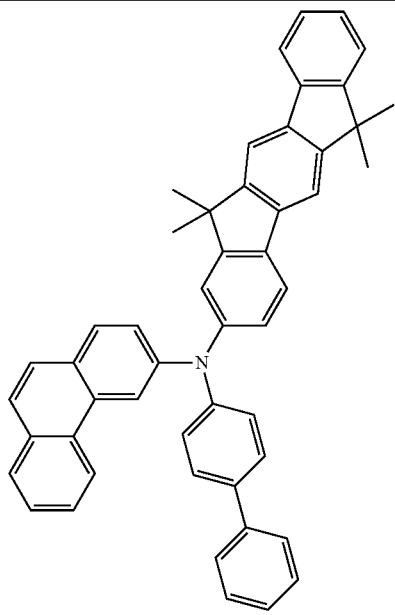
formula (167)
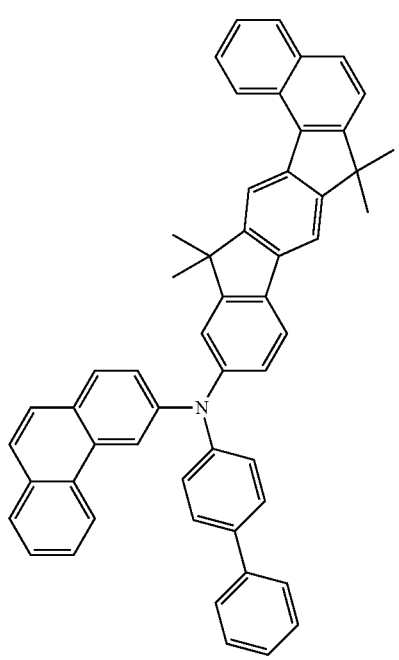 [SMILES: CC1(C)c2cc(N(c3ccc(-c4ccccc4)cc3)c3ccc4ccc5ccccc5c4c3)ccc2-c2cc3c(cc21)-c1c(ccc2ccccc12)C3(C)C]

formula (168)
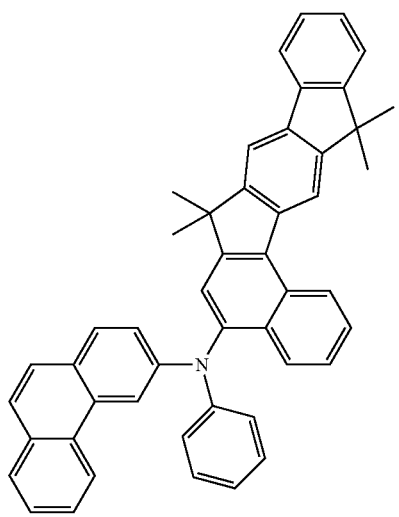 [SMILES: CC1(C)c2ccccc2-c2cc3c(cc21)-c1c(cc(N(c2ccccc2)c2ccc4ccc5ccccc5c4c2)c2ccccc12)C3(C)C]
formula (169)
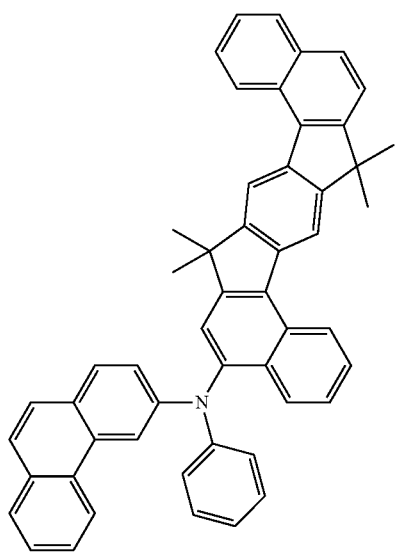 [SMILES: CC1(C)c2cc3c(cc2-c2c1ccc1ccccc21)C(C)(C)c1cc(N(c2ccccc2)c2ccc4ccc5ccccc5c4c2)c2ccccc2c1-3]
formula (170)
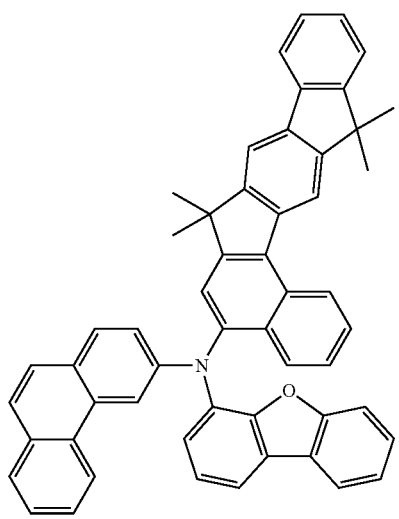 [SMILES: CC1(C)c2ccccc2-c2cc3c(cc21)-c1c(cc(N(c2ccc4ccc5ccccc5c4c2)c2cccc4c2oc2ccccc24)c2ccccc12)C3(C)C]

formula (171)
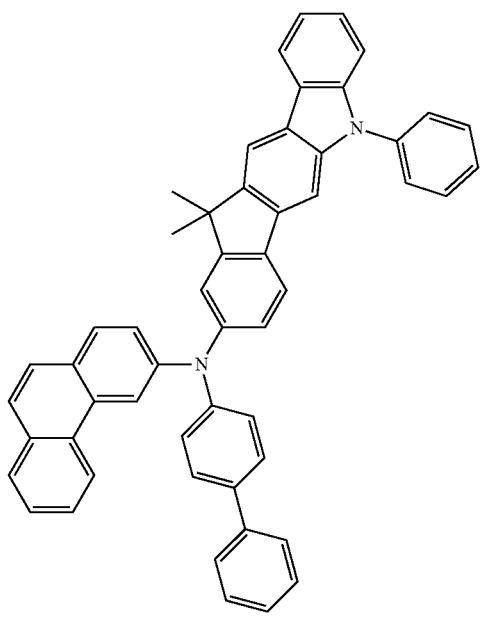 [SMILES: CC1(C)c2cc(N(c3ccc(-c4ccccc4)cc3)c3ccc4ccc5ccccc5c4c3)ccc2-c2cc3c(cc21)c1ccccc1n3-c1ccccc1]
formula (172)
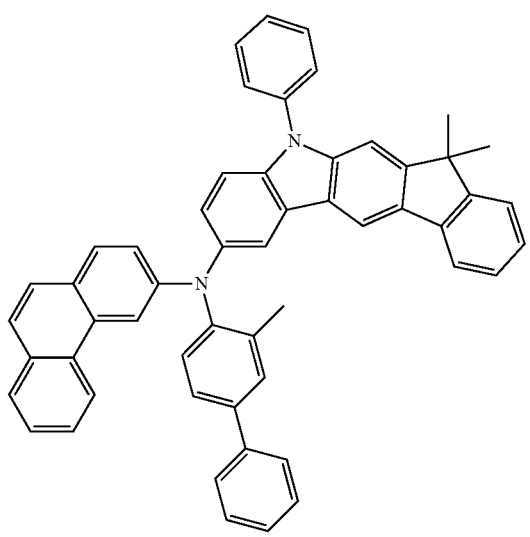 [SMILES: Cc1cc(-c2ccccc2)ccc1N(c1ccc2ccc3ccccc3c2c1)c1ccc2c(c1)c1cc3c(cc1n2-c1ccccc1)C(C)(C)c1ccccc1-3]
formula (173)
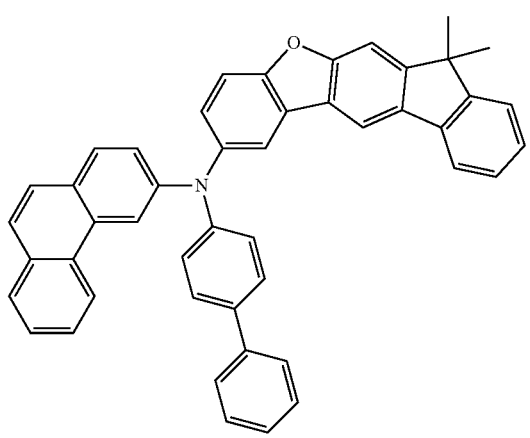 [SMILES: CC1(C)c2ccccc2-c2cc3c(cc21)oc1ccc(N(c2ccc(-c4ccccc4)cc2)c2ccc4ccc5ccccc5c4c2)cc13]

formula (174)
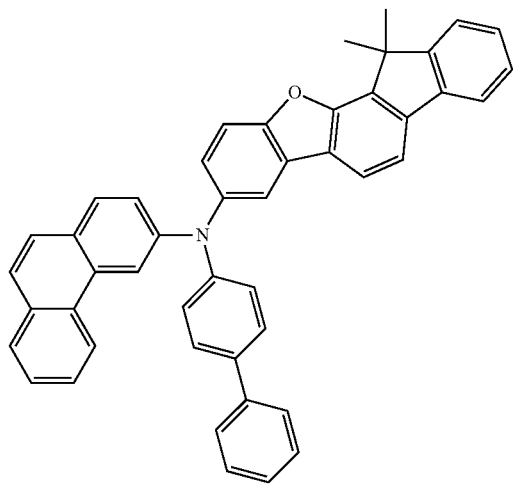 [SMILES: CC1(C)c2ccccc2-c2ccc3c(oc4ccc(N(c5ccc(-c6ccccc6)cc5)c5ccc6ccc7ccccc7c6c5)cc43)c21]
formula (175)
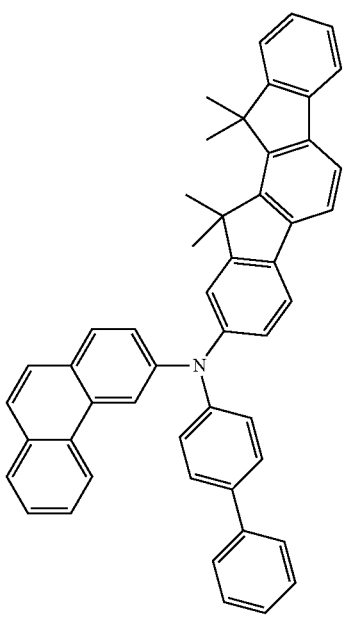 [SMILES: CC1(C)c2ccccc2-c2ccc3c(c21)C(C)(C)c1cc(N(c2ccc(-c4ccccc4)cc2)c2ccc4ccc5ccccc5c4c2)ccc1-3]
formula (176)
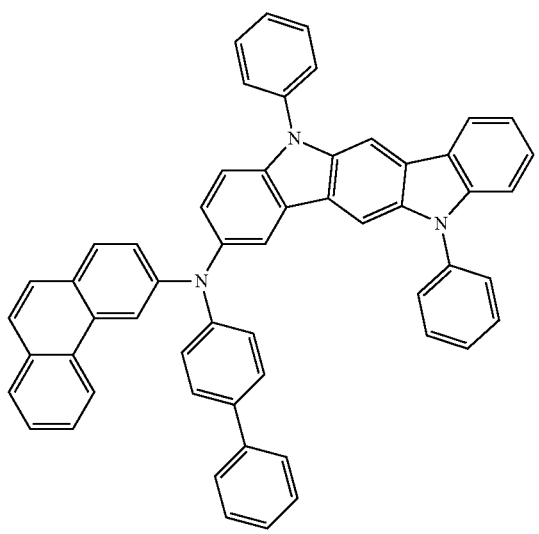 [SMILES: c1ccc(-c2ccc(N(c3ccc4ccc5ccccc5c4c3)c3ccc4c(c3)c3cc5c(cc3n4-c3ccccc3)c3ccccc3n5-c3ccccc3)cc2)cc1]

-continued
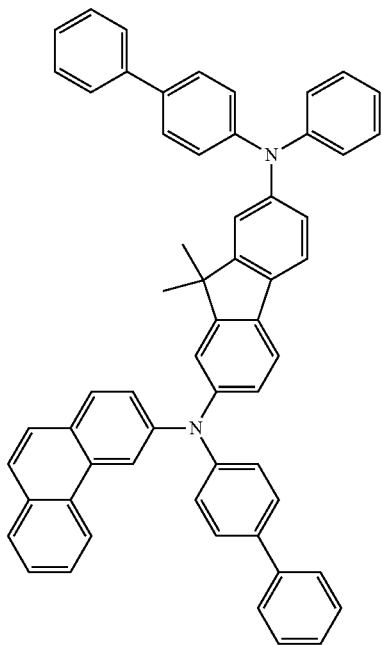 [SMILES: CC1(C)c2cc(N(c3ccccc3)c3ccc(-c4ccccc4)cc3)ccc2-c2ccc(N(c3ccc(-c4ccccc4)cc3)c3ccc4ccc5ccccc5c4c3)cc21]
formula (177)
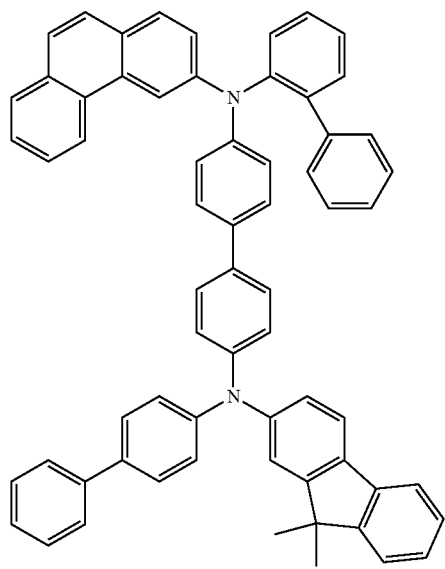 [SMILES: CC1(C)c2ccccc2-c2ccc(N(c3ccc(-c4ccccc4)cc3)c3ccc(-c4ccc(N(c5ccc6ccc7ccccc7c6c5)c5ccccc5-c5ccccc5)cc4)cc3)cc21]
formula (178)

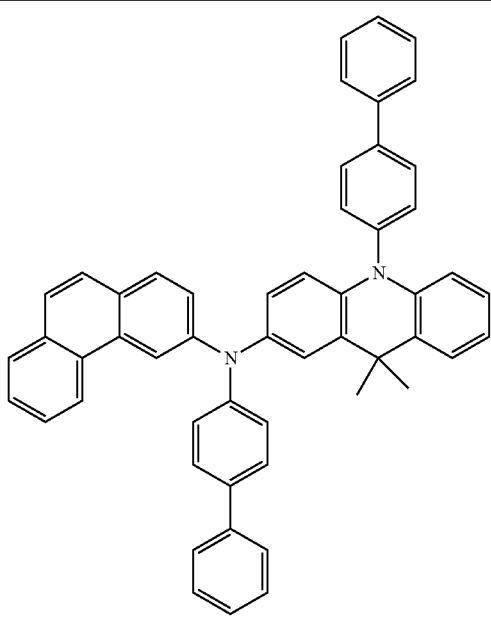
formula (179)
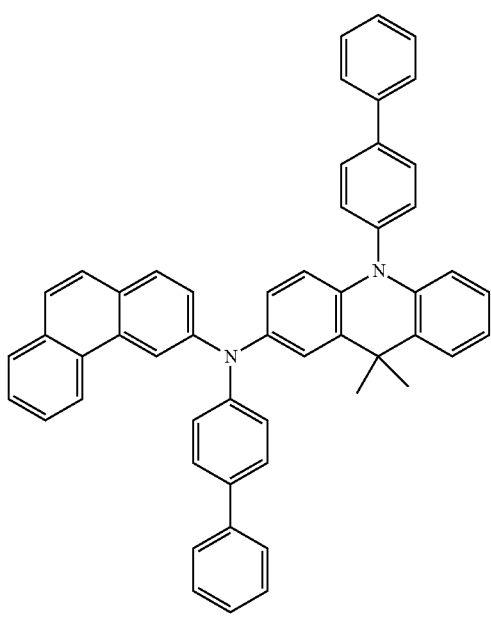 [SMILES: CC1(C)c2ccccc2N(c2ccc(-c3ccccc3)cc2)c2ccc(N(c3ccc(-c4ccccc4)cc3)c3ccc4ccc5ccccc5c4c3)cc21]
formula (180)

formula (181)
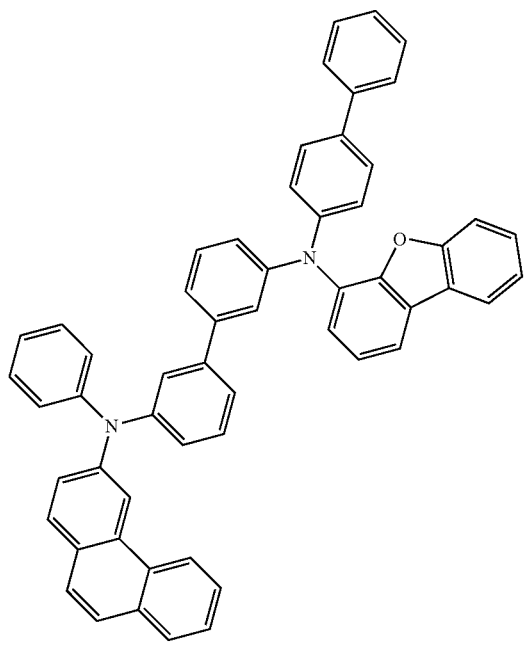 [SMILES: c1ccc(-c2ccc(N(c3cccc(-c4cccc(N(c5ccccc5)c5ccc6ccc7ccccc7c6c5)c4)c3)c3cccc4c3oc3ccccc34)cc2)cc1]
formula (182)
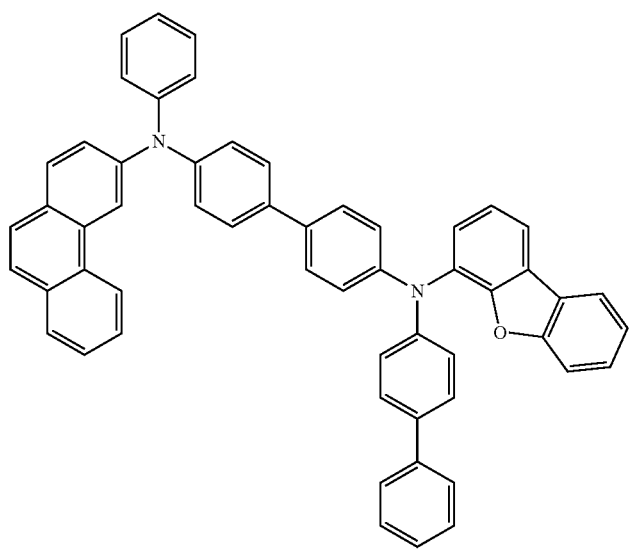 [SMILES: c1ccc(-c2ccc(N(c3ccc(-c4ccc(N(c5ccccc5)c5ccc6ccc7ccccc7c6c5)cc4)cc3)c3cccc4c3oc3ccccc34)cc2)cc1]
formula (183)
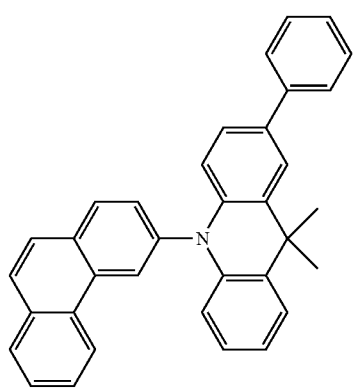 [SMILES: CC1(C)c2ccccc2N(c2ccc3ccc4ccccc4c3c2)c2ccc(-c3ccccc3)cc21]

formula (184)
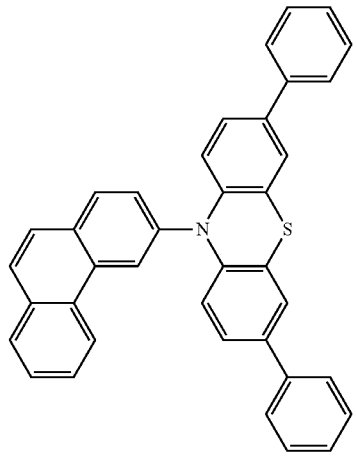 [SMILES: c1ccc(-c2ccc3c(c2)Sc2cc(-c4ccccc4)ccc2N3c2ccc3ccc4ccccc4c3c2)cc1]
formula (185)
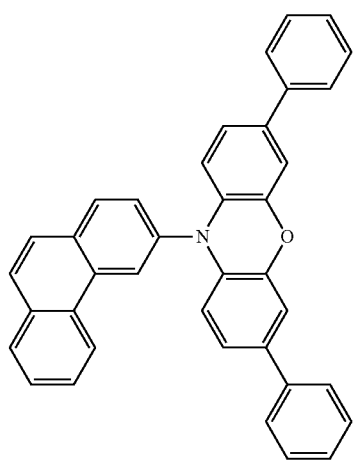 [SMILES: c1ccc(-c2ccc3c(c2)Oc2cc(-c4ccccc4)ccc2N3c2ccc3ccc4ccccc4c3c2)cc1]
formula (186)
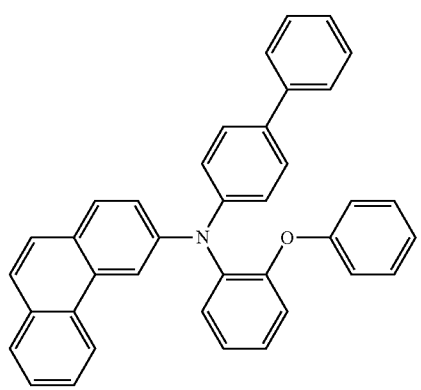 [SMILES: c1ccc(Oc2ccccc2N(c2ccc(-c3ccccc3)cc2)c2ccc3ccc4ccccc4c3c2)cc1]

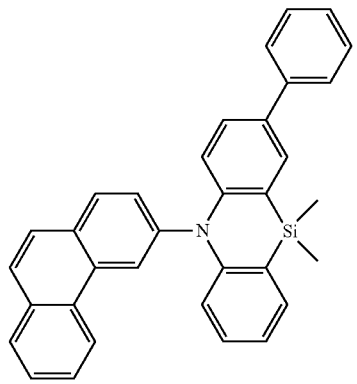 [SMILES: C[Si]1(C)c2ccccc2N(c2ccc3ccc4ccccc4c3c2)c2ccc(-c3ccccc3)cc21]
formula (187)
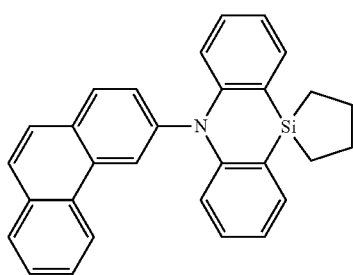 [SMILES: c1ccc2c(c1)N(c1ccc3ccc4ccccc4c3c1)c1ccccc1[Si]21CCCC1]
formula (188)
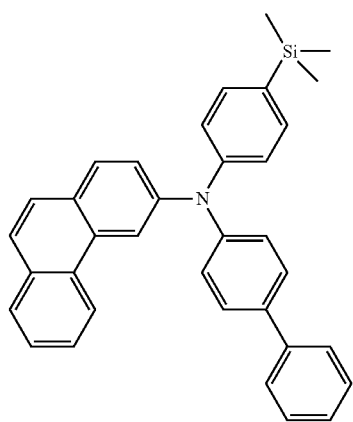 [SMILES: C[Si](C)(C)c1ccc(N(c2ccc(-c3ccccc3)cc2)c2ccc3ccc4ccccc4c3c2)cc1]
formula (189)
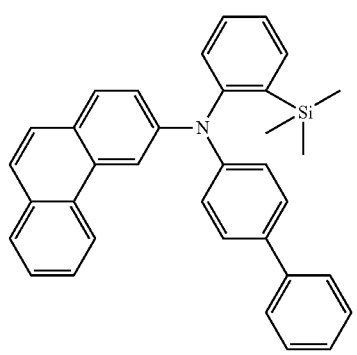 [SMILES: C[Si](C)(C)c1ccccc1N(c1ccc(-c2ccccc2)cc1)c1ccc2ccc3ccccc3c2c1]
formula (190)

-continued
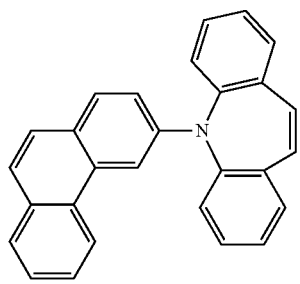 [SMILES: C1=Cc2ccccc2N(c2ccc3ccc4ccccc4c3c2)c2ccccc21]
formula (191)
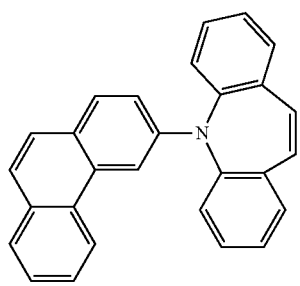 [SMILES: C1=Cc2ccccc2N(c2ccc3ccc4ccccc4c3c2)c2ccccc21]
formula (192)
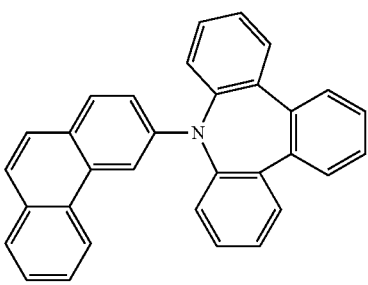 [SMILES: c1ccc2c(c1)-c1ccccc1N(c1ccc3ccc4ccccc4c3c1)c1ccccc1-2]
formula (193)
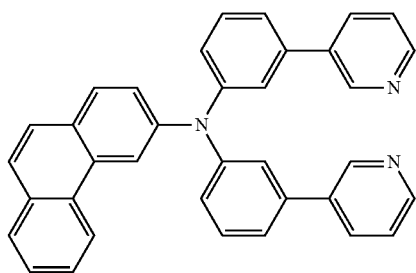 [SMILES: c1cncc(-c2cccc(N(c3cccc(-c4cccnc4)c3)c3ccc4ccc5ccccc5c4c3)c2)c1]
formula (194)
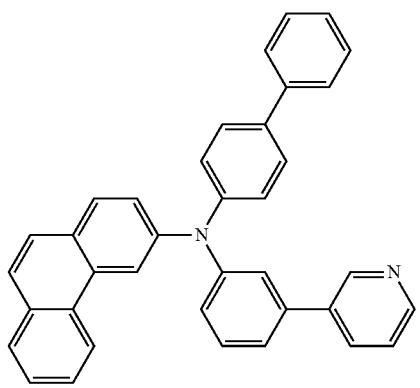 [SMILES: c1ccc(-c2ccc(N(c3cccc(-c4cccnc4)c3)c3ccc4ccc5ccccc5c4c3)cc2)cc1]
formula (195)

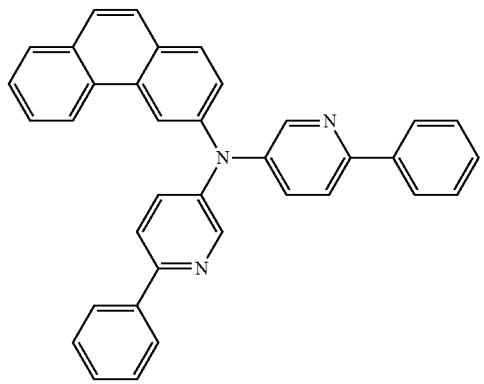 [SMILES: c1ccc(-c2ccc(N(c3ccc(-c4ccccc4)nc3)c3ccc4ccc5ccccc5c4c3)cn2)cc1]
formula (196)
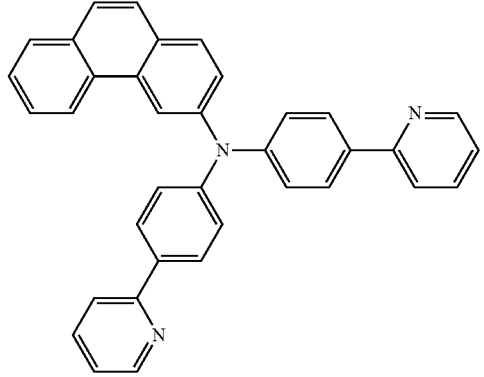 [SMILES: c1ccc(-c2ccc(N(c3ccc(-c4ccccn4)cc3)c3ccc4ccc5ccccc5c4c3)cc2)nc1]
formula (197)
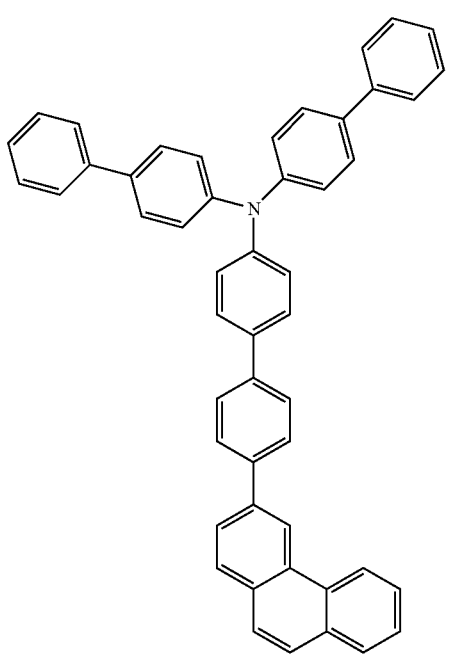 [SMILES: c1ccc(-c2ccc(N(c3ccc(-c4ccccc4)cc3)c3ccc(-c4ccc(-c5ccc6ccc7ccccc7c6c5)cc4)cc3)cc2)cc1]
formula (198)

formula (199)
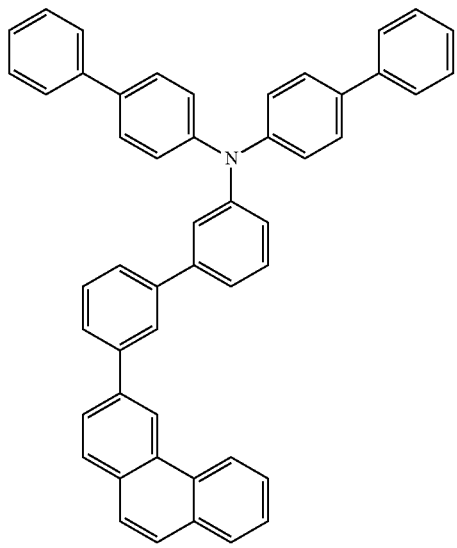 [SMILES: c1ccc(-c2ccc(N(c3ccc(-c4ccccc4)cc3)c3cccc(-c4cccc(-c5ccc6ccc7ccccc7c6c5)c4)c3)cc2)cc1]
formula (200)
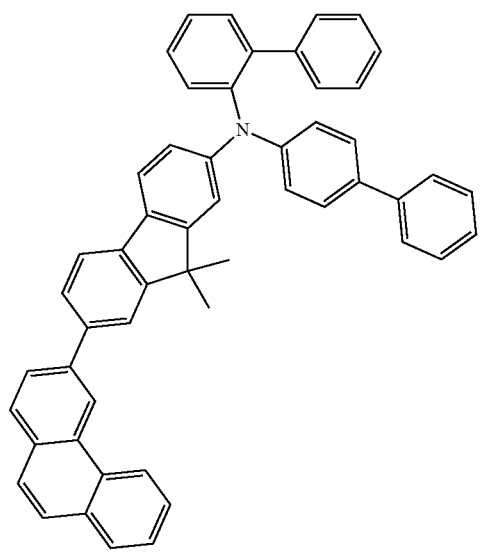 [SMILES: CC1(C)c2cc(-c3ccc4ccc5ccccc5c4c3)ccc2-c2ccc(N(c3ccc(-c4ccccc4)cc3)c3ccccc3-c3ccccc3)cc21]
formula (201)
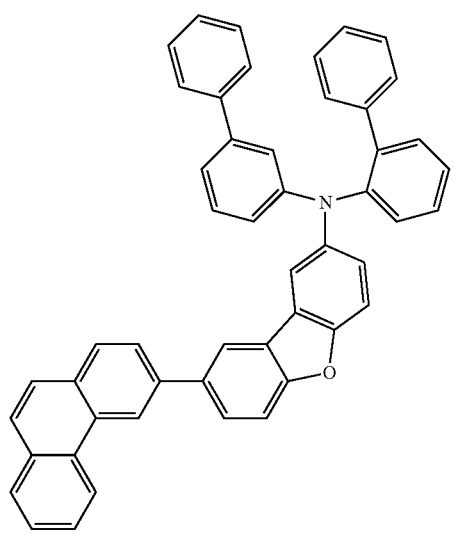 [SMILES: c1ccc(-c2cccc(N(c3ccc4oc5ccc(-c6ccc7ccc8ccccc8c7c6)cc5c4c3)c3ccccc3-c3ccccc3)c2)cc1]

formula (202)
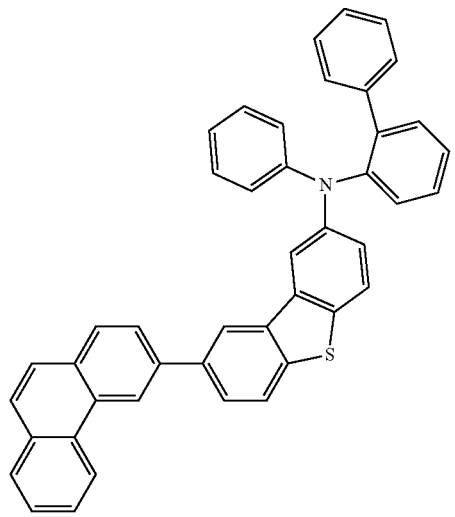 [SMILES: c1ccc(-c2ccccc2N(c2ccccc2)c2ccc3sc4ccc(-c5ccc6ccc7ccccc7c6c5)cc4c3c2)cc1]
formula (203)
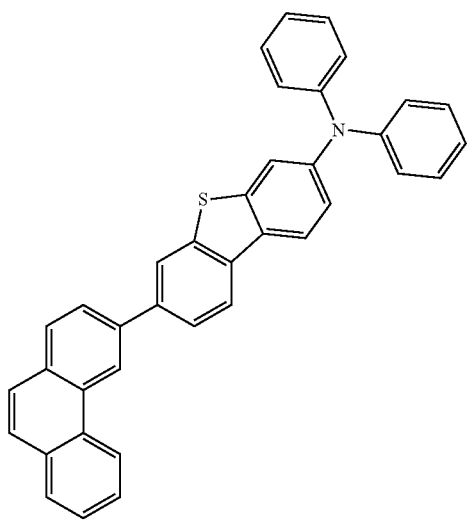 [SMILES: c1ccc(N(c2ccccc2)c2ccc3c(c2)sc2cc(-c4ccc5ccc6ccccc6c5c4)ccc23)cc1]
formula (204)
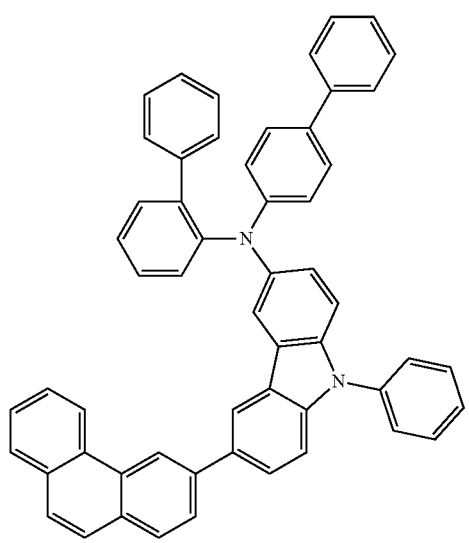 [SMILES: c1ccc(-c2ccc(N(c3ccc4c(c3)c3cc(-c5ccc6ccc7ccccc7c6c5)ccc3n4-c3ccccc3)c3ccccc3-c3ccccc3)cc2)cc1]

-continued
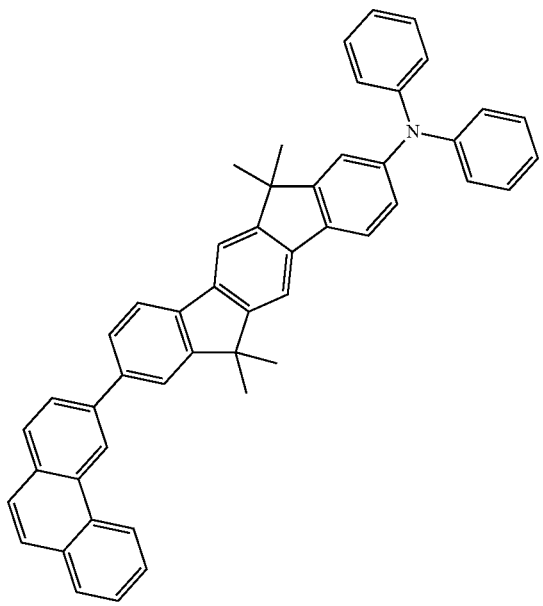 [SMILES: CC1(C)c2cc(-c3ccc4ccc5ccccc5c4c3)ccc2-c2cc3c(cc21)-c1ccc(N(c2ccccc2)c2ccccc2)cc1C3(C)C]
formula (205)
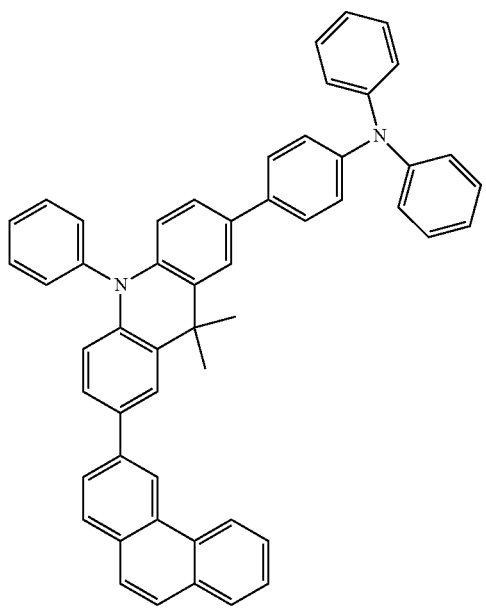 [SMILES: CC1(C)c2cc(-c3ccc(N(c4ccccc4)c4ccccc4)cc3)ccc2N(c2ccccc2)c2ccc(-c3ccc4ccc5ccccc5c4c3)cc21]
formula (206)

formula (207)
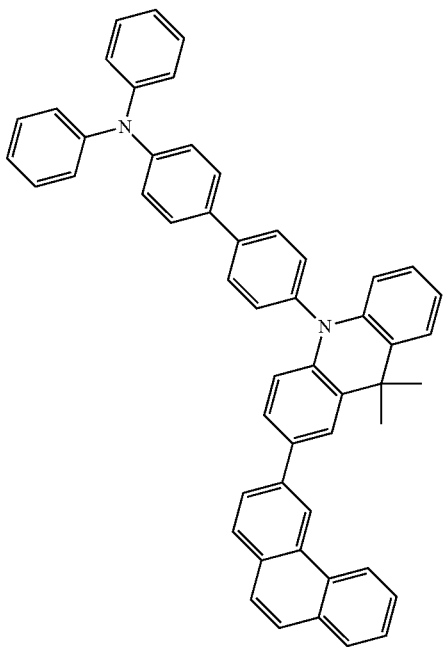 [SMILES: CC1(C)c2ccccc2N(c2ccc(-c3ccc(N(c4ccccc4)c4ccccc4)cc3)cc2)c2ccc(-c3ccc4ccc5ccccc5c4c3)cc21]
formula (208)
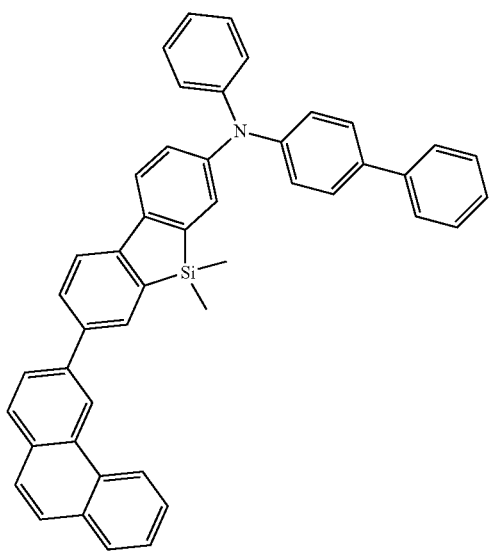 [SMILES: C[Si]1(C)c2cc(-c3ccc4ccc5ccccc5c4c3)ccc2-c2ccc(N(c3ccccc3)c3ccc(-c4ccccc4)cc3)cc21]

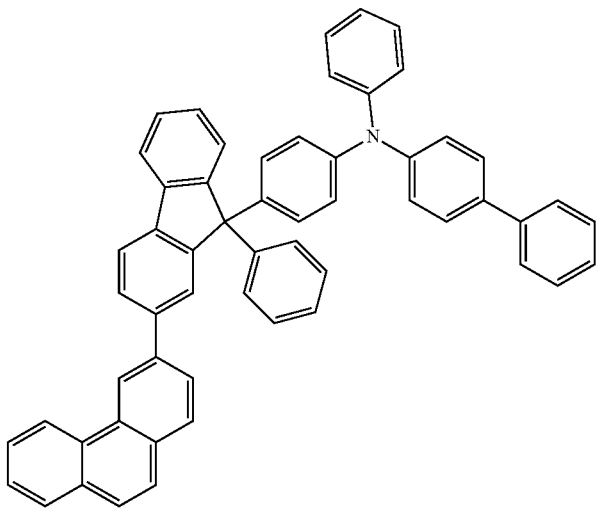 [SMILES: c1ccc(-c2ccc(N(c3ccccc3)c3ccc(C4(c5ccccc5)c5ccccc5-c5ccc(-c6ccc7ccc8ccccc8c7c6)cc54)cc3)cc2)cc1]
formula (209)
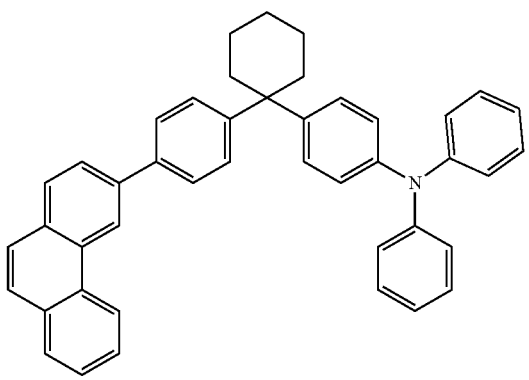 [SMILES: c1ccc(N(c2ccccc2)c2ccc(C3(c4ccc(-c5ccc6ccc7ccccc7c6c5)cc4)CCCCC3)cc2)cc1]
formula (210)
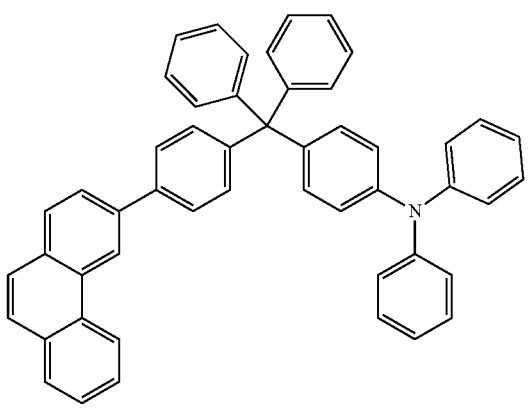 [SMILES: c1ccc(N(c2ccccc2)c2ccc(C(c3ccccc3)(c3ccccc3)c3ccc(-c4ccc5ccc6ccccc6c5c4)cc3)cc2)cc1]
formula (211)

formula (212)
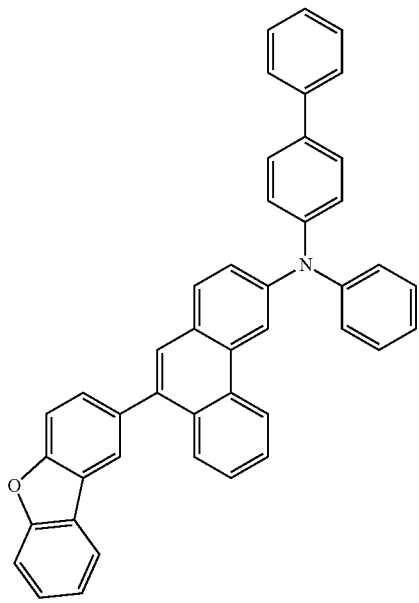 [SMILES: c1ccc(-c2ccc(N(c3ccccc3)c3ccc4cc(-c5ccc6oc7ccccc7c6c5)c5ccccc5c4c3)cc2)cc1]
formula (213)
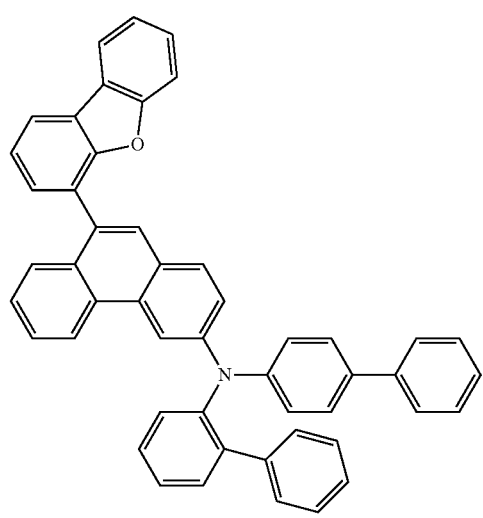 [SMILES: c1ccc(-c2ccc(N(c3ccc4cc(-c5cccc6c5oc5ccccc56)c5ccccc5c4c3)c3ccccc3-c3ccccc3)cc2)cc1]

formula (214)
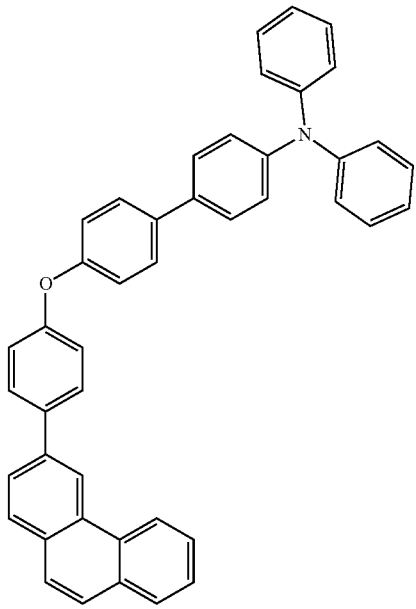 [SMILES: c1ccc(N(c2ccccc2)c2ccc(-c3ccc(Oc4ccc(-c5ccc6ccc7ccccc7c6c5)cc4)cc3)cc2)cc1]
formula (215)
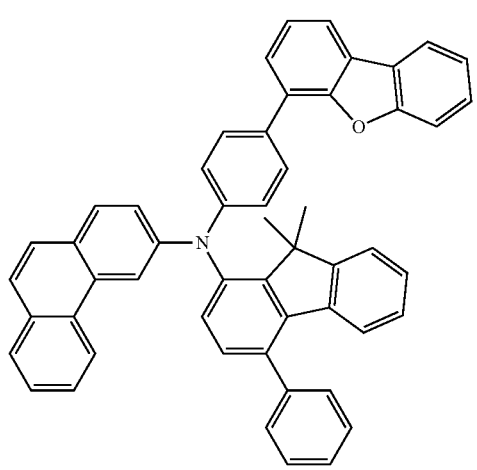 [SMILES: CC1(C)c2ccccc2-c2c(-c3ccccc3)ccc(N(c3ccc(-c4cccc5c4oc4ccccc45)cc3)c3ccc4ccc5ccccc5c4c3)c21]
formula (216)
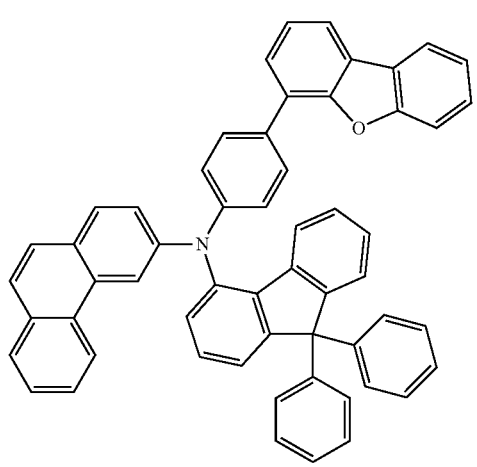 [SMILES: c1ccc(C2(c3ccccc3)c3ccccc3-c3c(N(c4ccc(-c5cccc6c5oc5ccccc56)cc4)c4ccc5ccc6ccccc6c5c4)cccc32)cc1]

formula (217)
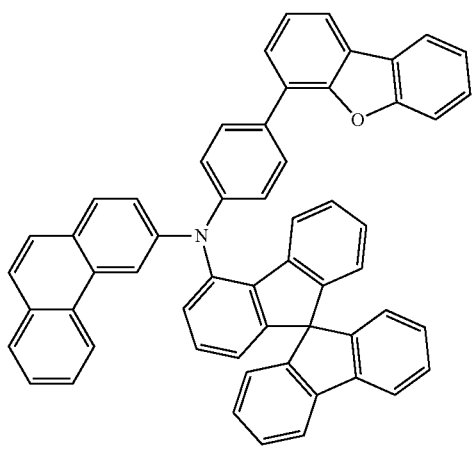 [SMILES: c1ccc2c(c1)-c1ccccc1C21c2ccccc2-c2c(N(c3ccc(-c4cccc5c4oc4ccccc45)cc3)c3ccc4ccc5ccccc5c4c3)cccc21]
formula (218)
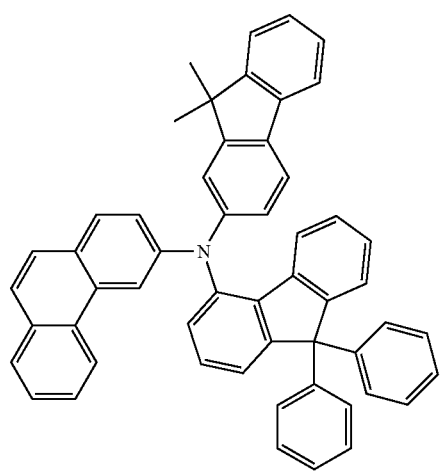 [SMILES: CC1(C)c2ccccc2-c2ccc(N(c3ccc4ccc5ccccc5c4c3)c3cccc4c3-c3ccccc3C4(c3ccccc3)c3ccccc3)cc21]
formula (219)
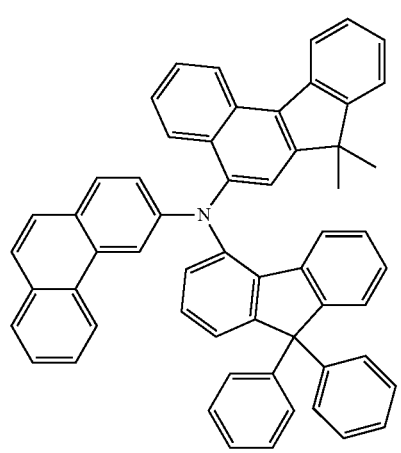 [SMILES: CC1(C)c2ccccc2-c2c1cc(N(c1ccc3ccc4ccccc4c3c1)c1cccc3c1-c1ccccc1C3(c1ccccc1)c1ccccc1)c1ccccc21]

formula (220)
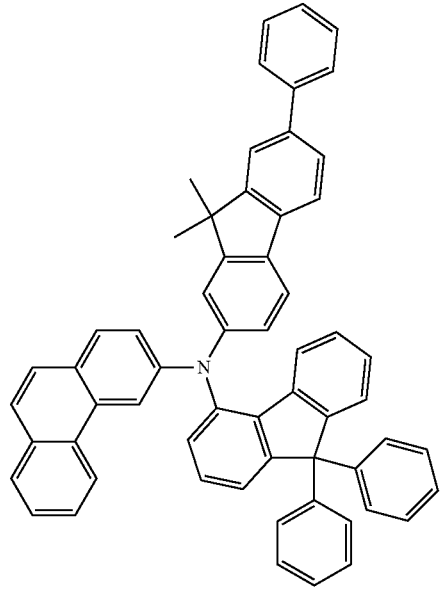 [SMILES: CC1(C)c2cc(-c3ccccc3)ccc2-c2ccc(N(c3ccc4ccc5ccccc5c4c3)c3cccc4c3-c3ccccc3C4(c3ccccc3)c3ccccc3)cc21]
formula (221)
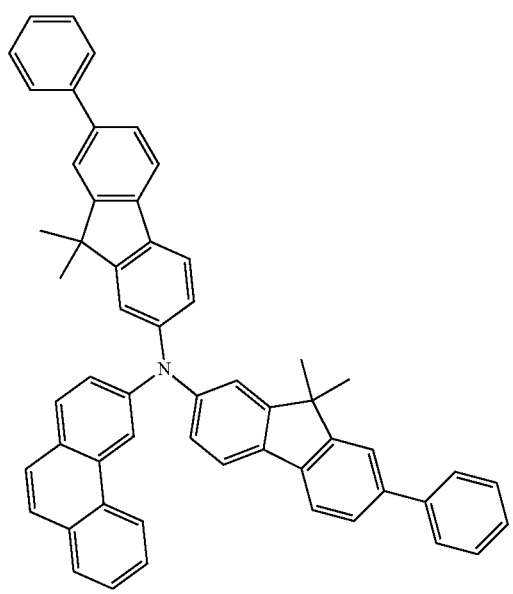 [SMILES: CC1(C)c2cc(-c3ccccc3)ccc2-c2ccc(N(c3ccc4c(c3)C(C)(C)c3cc(-c5ccccc5)ccc3-4)c3ccc4ccc5ccccc5c4c3)cc21]

formula (222)

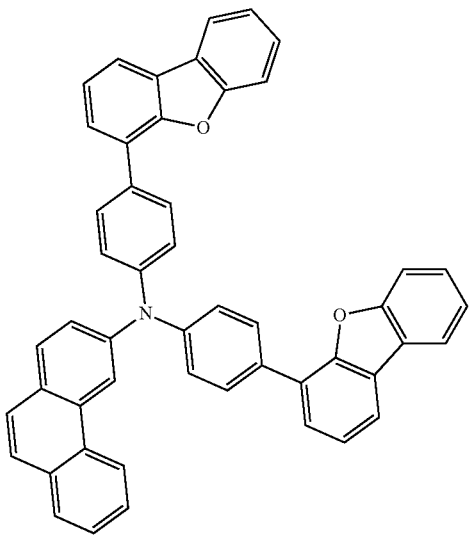 [SMILES: c1ccc2c(c1)ccc1ccc(N(c3ccc(-c4cccc5c4oc4ccccc45)cc3)c3ccc(-c4cccc5c4oc4ccccc45)cc3)cc12]

The compounds according to the invention can be synthesised by processes and reaction types known from the prior art, for example halogenation, Buchwald coupling and Suzuki coupling.

A preferred process for the preparation of the compounds according to the invention starts from the basic structures depicted as starting materials in Scheme 1. These are in some cases commercially available, in other cases they can be prepared in a few synthetic steps from simple, commercially available compounds.

Scheme 1 below shows a preferred synthetic route for the preparation of the compounds according to the invention. For the synthesis of the compounds according to the invention, on the phenanthrene compound A is reacted with an amine B of the formula $Ar^2$—NH—$Ar^1$ in a Buchwald coupling Scheme 1

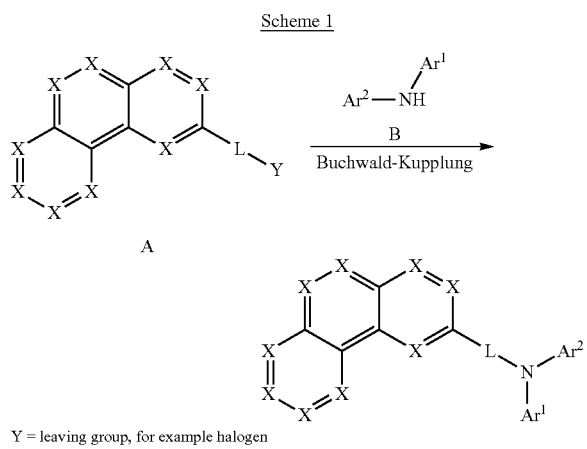

Y = leaving group, for example halogen

Another preferred synthetic route for the preparation of the compounds according to the invention is depicted in Scheme 2. The synthetic route comprises two coupling reactions: firstly, the the phenanthrene compound A is reacted with an amine C of the formula $Ar^2$—$NH_2$ in a first Buchwald coupling. Finally, a second Buchwald coupling is carried out with a compound D, for example with a bromoaryl compound.

Scheme 2

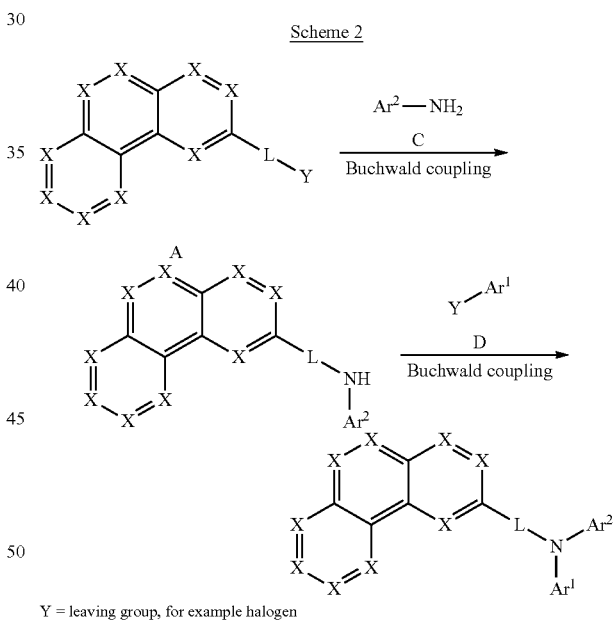

Y = leaving group, for example halogen

The coupling reactions here are preferably Buchwald couplings.

The synthesis of the starting compounds (A) presents the person skilled in the art with no difficulties. They can be prepared, for example, by conversion of acetyl compounds into amines and subsequent conversion into halides by means of the Sandmayer reaction. Examples in this respect are disclosed below.

The compounds according to the invention described above, in particular compounds which are substituted by reactive leaving groups, such as bromine, iodine, chlorine, boronic acid or boronic acid ester, can be used as monomers for the generation of corresponding oligomers, dendrimers or polymers. The oligomerisation or polymerisation here preferably takes place via the halogen functionality or the boronic acid functionality.

The present invention thus furthermore relates to a process for the preparation of compounds of the formula (1) which is characterised in that the process takes place either in accordance with Scheme 1 or in accordance with Scheme 2.

The compounds according to the invention described above, in particular compounds which are substituted by reactive leaving groups, such as bromine, iodine, chlorine, boronic acid or boronic acid ester, can be used as monomers for the generation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double bond or C—C or triple bond respectively, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (1), where the bond(s) to the polymer, oligomer or dendrimer may be localised at any desired positions in formula (1) which are substituted by $R^1$ or $R^2$. Depending on the linking of the compound of the formula (1), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or they may be linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or mini-emulsions. It may be preferred to use mixtures of two or more solvents for this purpose. Suitable and preferred solvents are, for example, toluene, phenoxytoluene, anisole, o-, m- or p-xylene, methyl benzoate, dimethylanisole, mesitylene, tetralin, veratrol, THF, methyl-THF, THP, chlorobenzene, dioxane or mixtures of these solvents.

The invention therefore furthermore relates to a formulation, in particular a solution, dispersion or mini-emulsion, comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention can be employed as compositions with other organically functional materials which are used in electronic devices. A multiplicity of possible organically functional materials (often also called organic semiconductors) are known to the person skilled in the art here. The present invention therefore also relates to a composition comprising one or more compound according to the invention and at least one further organically functional material selected from the group consisting of fluorescent emitters, phosphorescent emitters, host materials, matrix materials, electron-transport materials, electron-injection materials, hole-conductor materials, hole-injection materials, electron-blocking materials and hole-blocking materials.

The compounds according to the invention are suitable for use in electronic devices, in particular in organic electroluminescent devices (OLEDs). Depending on the substitution, the compounds are employed in various functions and layers.

The invention therefore furthermore relates to the use of the compounds of the formula (1) in electronic devices and to electronic devices themselves which comprise one or more compounds of the formula (1). The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention relates, as already stated above, to electronic devices comprising at least one compound of the formula (1). The electronic devices here are preferably selected from the devices mentioned above. Particular preference is given to organic electroluminescent devices (OLEDs) comprising anode, cathode and at least one emitting layer, characterised in that at least one organic layer, which can be an emitting layer, a hole-transport layer or another layer, comprises at least one compound of the formula (1).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Especial preference is given to three-layer systems, i.e. systems having three emitting layers, where the three layers exhibit blue, green and orange or red emission (for the basic structure see, for example, WO 2005/011013). The compounds according to the invention may be present in a hole-transport layer, an emitting layer and/or in another layer in such devices. It should be noted that, for the generation of white light, an emitter compound used individually which emits in a broad wavelength range may also be suitable instead of a plurality of emitter compounds emitting in colour.

It is preferred in accordance with the invention for the compound of the formula (1) to be employed in an electronic device comprising one or more phosphorescent dopants. The compound here can be used in various layers, preferably in a hole-transport layer, a hole-injection layer or in an emitting layer. However, the compound of the formula (1) can also be employed in accordance with the invention in an electronic device comprising one or more fluorescent dopants.

If the compound of the formula (1) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (1) then additionally comprises one or more p-dopants. The p-dopants employed in accordance with the present invention are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

In a further preferred embodiment of the invention, the compound of the formula (1) is used as hole-transport material in combination with a hexaazatriphenylene derivative, as described in US 2007/0092755. The hexaazatriphenylene derivative here is particularly preferably employed in a separate layer.

Particularly preferred p-dopants are quinodimethane compounds, azaindenofluorenediones, azaphenalenes, azatriphenylenes, 12, metal halides, preferably transition-metal halides, metal oxides, preferably metal oxides containing at least one transition metal or a metal of the 3rd main group, and transition-metal complexes, preferably complexes of Cu, Co, Ni, Pd and Pt with ligands containing at least one oxygen atom as bonding site. Preference is furthermore given to transition-metal oxides as dopants, preferably oxides of rhenium, molybdenum and tungsten, particularly preferably $Re_2O_7$, $MoO_3$, $WO_3$ and $ReO_3$.

Preferred p-dopants are furthermore the following compounds:
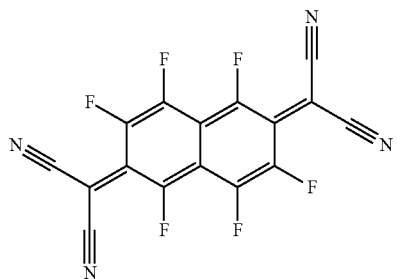
(D-1)
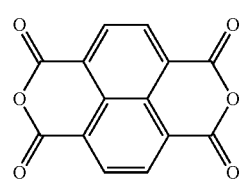
(D-2)
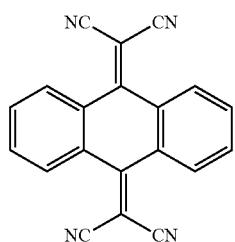
(D-3)
(D-4)
(D-5)
(D-6)
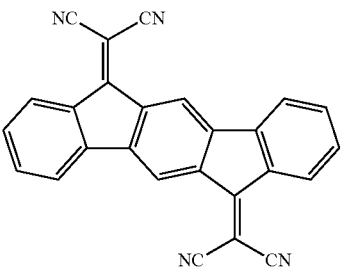
(D-7)
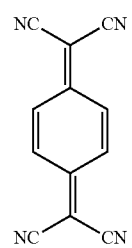
(D-8)
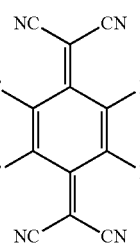
(D-9)
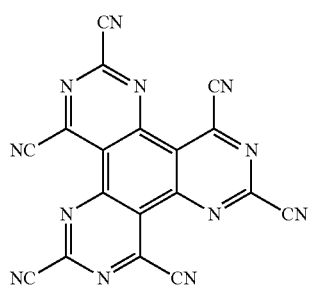
(D-10)
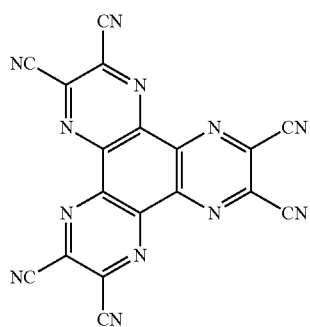
(D-11)

-continued (D-12)

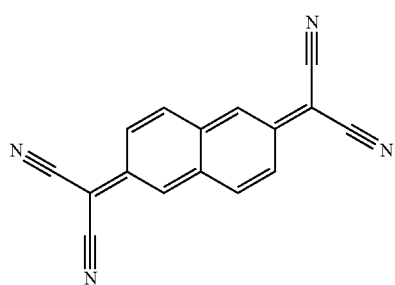

The p-dopant in hole-transport layer is preferably present in a concentration of 0.1 to 20% by vol, very preferably 0.5 to 12% by vol, particularly preferably 1 to 8% by vol and very particularly preferably 2 to 6% by vol.

The hole-transport layer preferably has a thickness of 5 to 50 nm, particularly preferably 10 to 40 nm.

The term phosphorescent dopants typically encompasses compounds in which the light emission takes place through a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of the emitters described above are revealed by the applications WO 00/70655, WO 01/41512, WO 02/02714, WO 02/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable. The person skilled in the art will also be able, without inventive step, to employ further phosphorescent complexes in combination with the compounds of the formula (1) in organic electroluminescent devices.

Explicit examples of suitable phosphorescent emitter compounds are furthermore revealed by the following table.

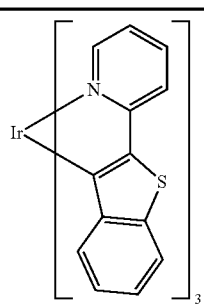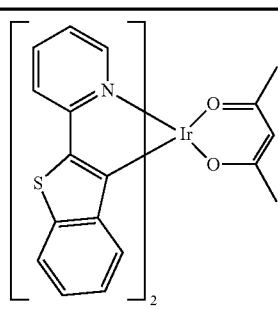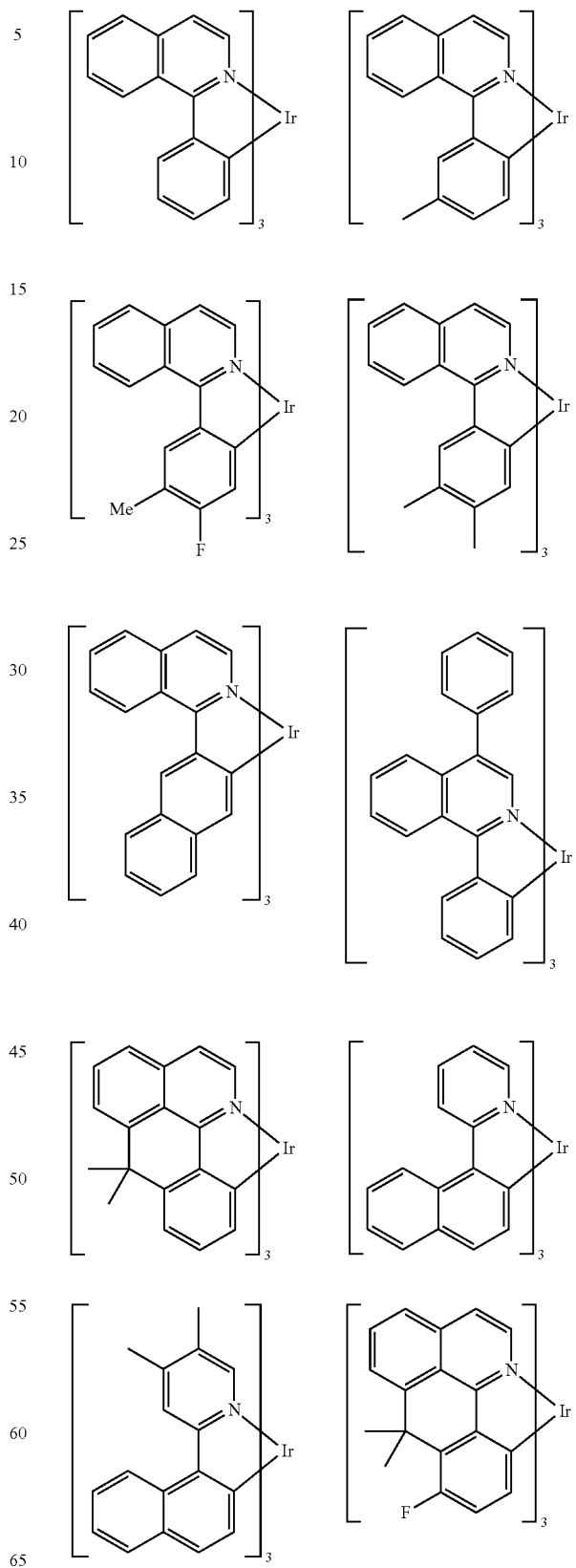

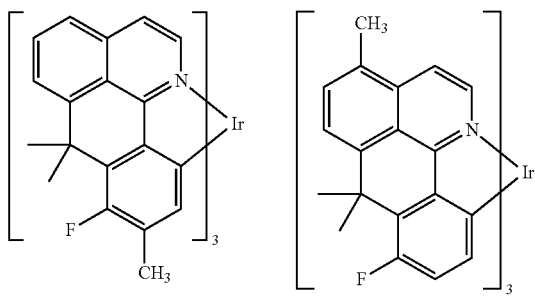
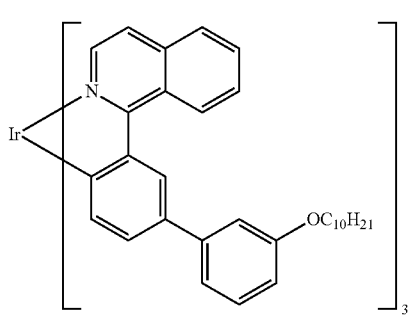
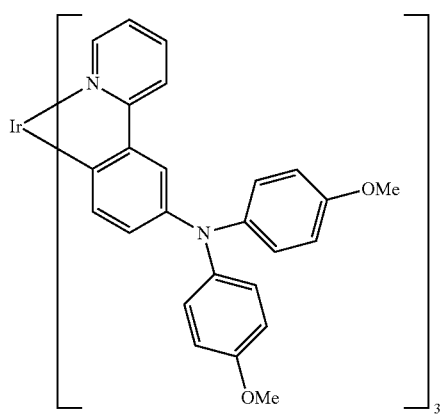
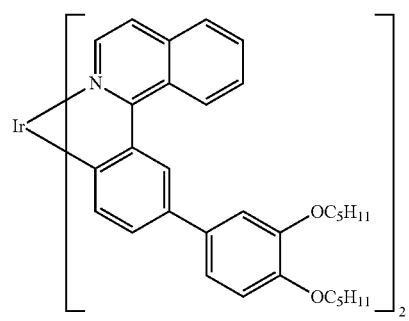
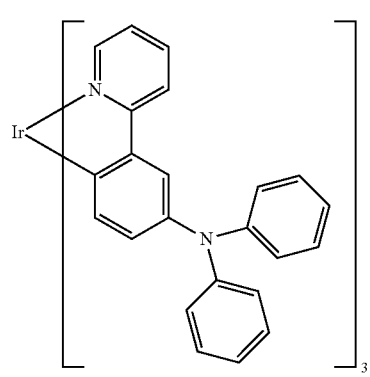
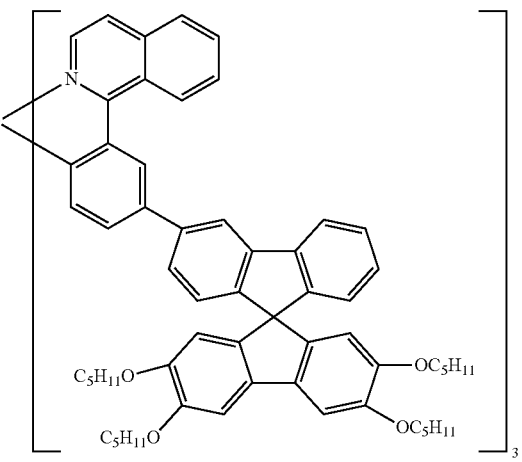
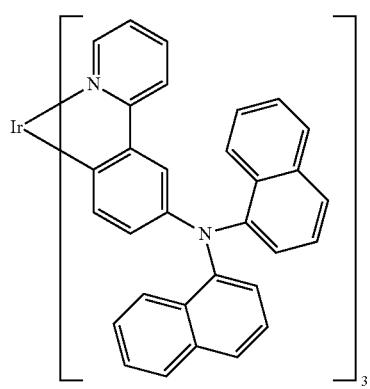
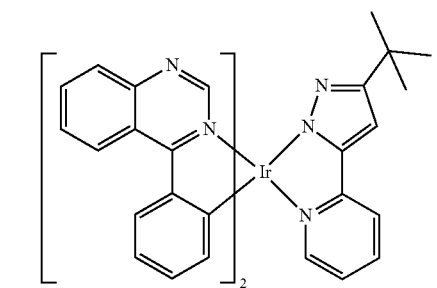

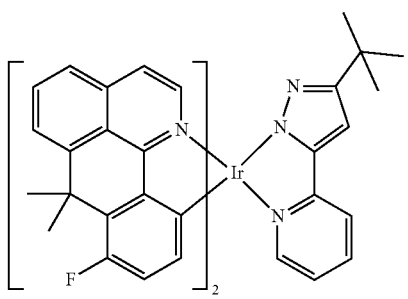
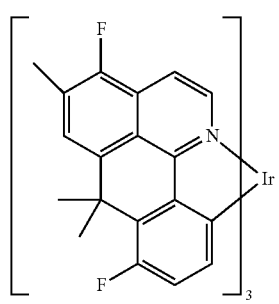
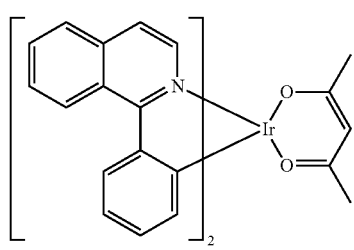
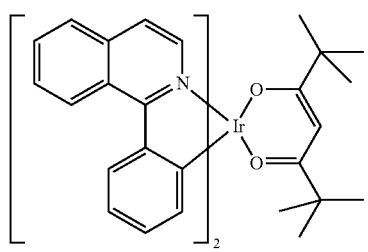
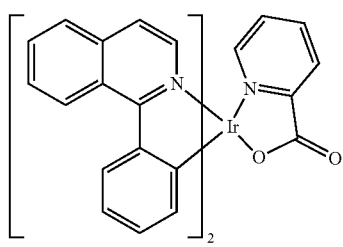
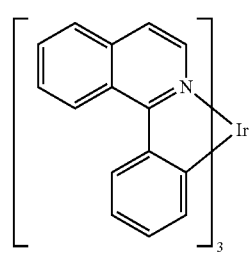
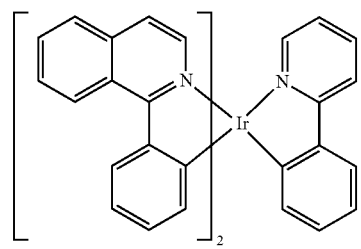
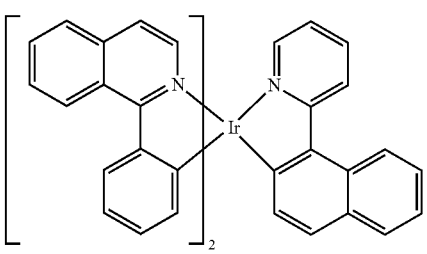
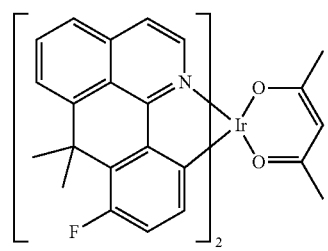
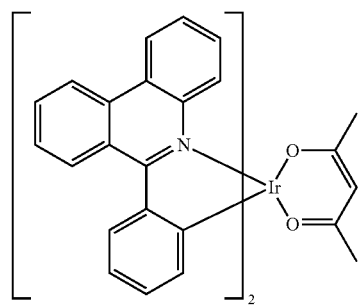
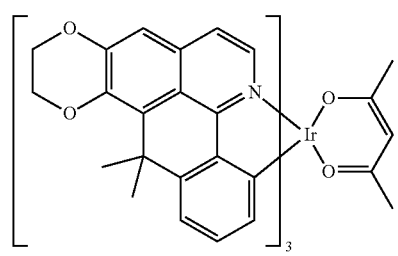
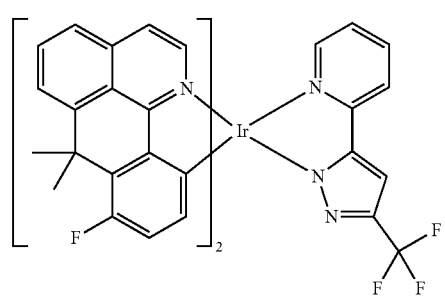

123
-continued
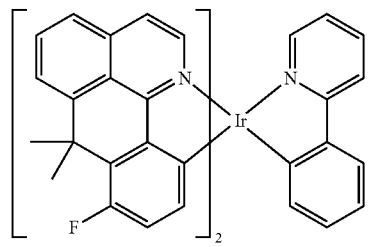
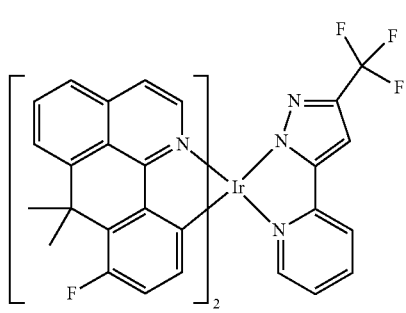
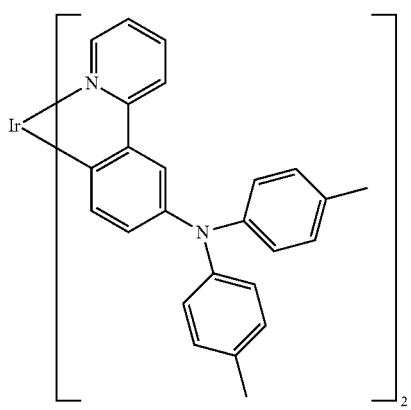
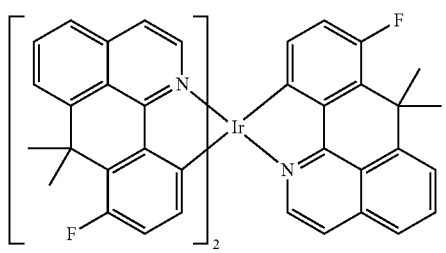
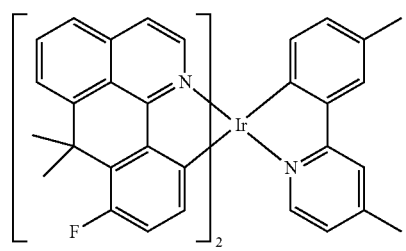
124
-continued
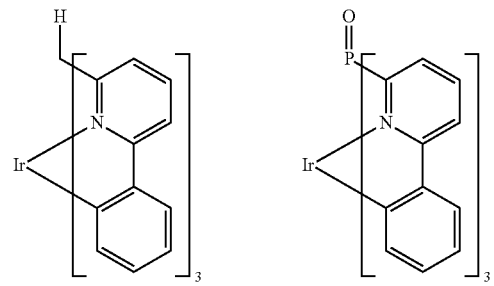
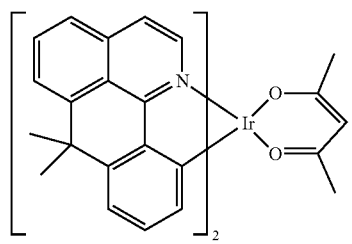
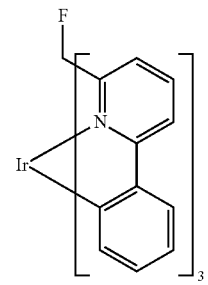
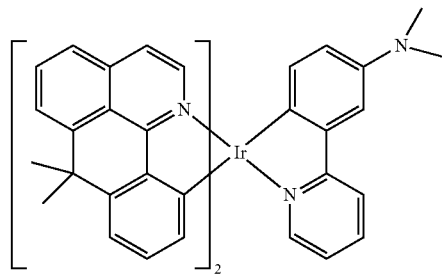
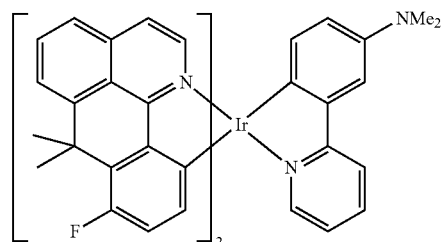
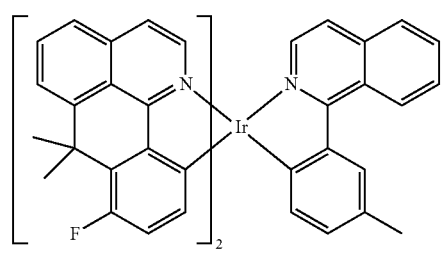

| 125 -continued | 126 -continued |
|---|---|
| 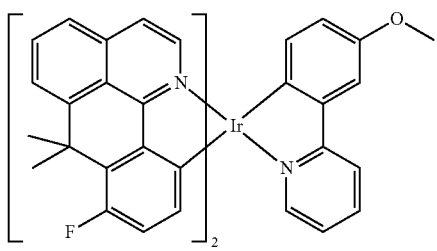 | 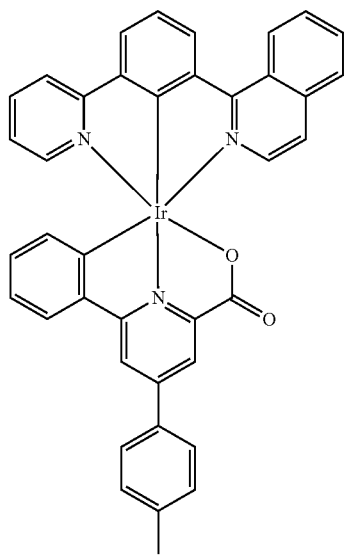 |
| 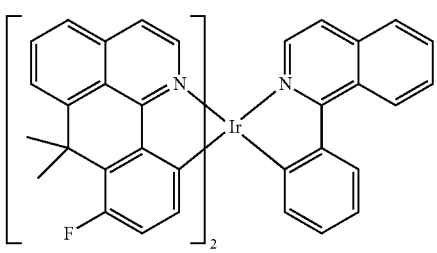 | |
| | 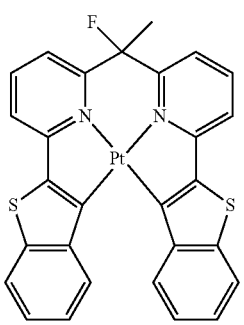 |
| 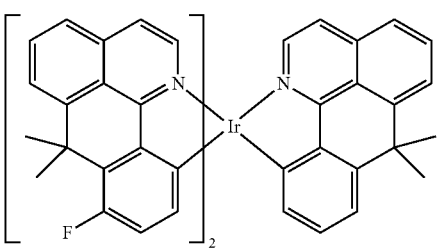 | |
| 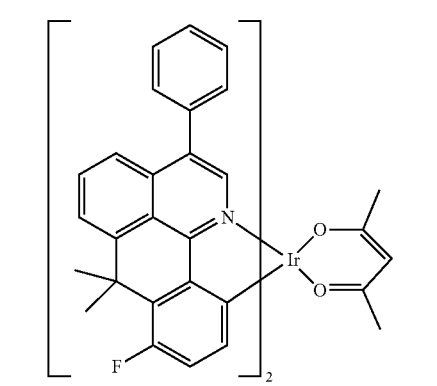 | 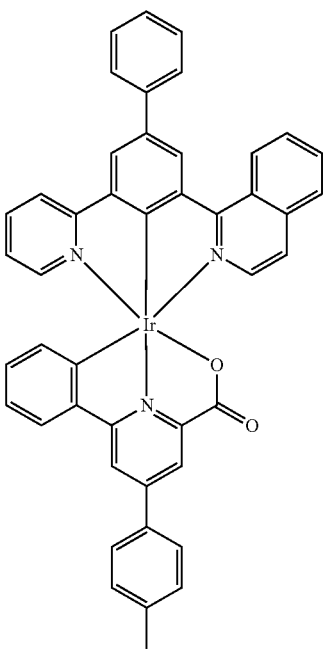 |

127
-continued
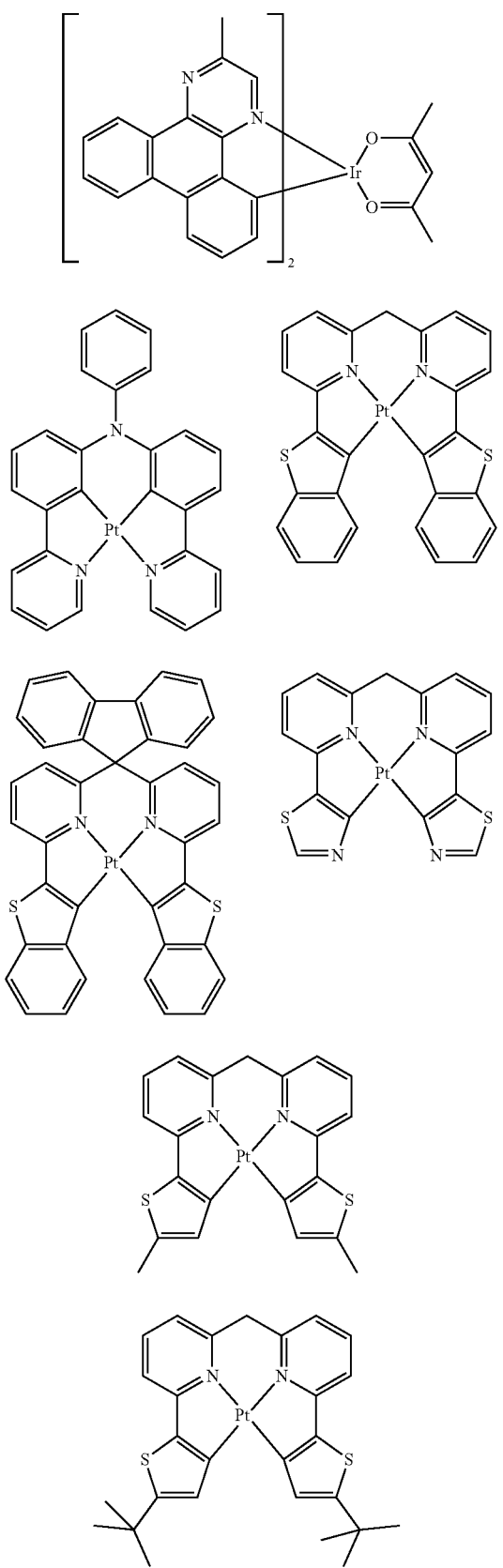
128
-continued
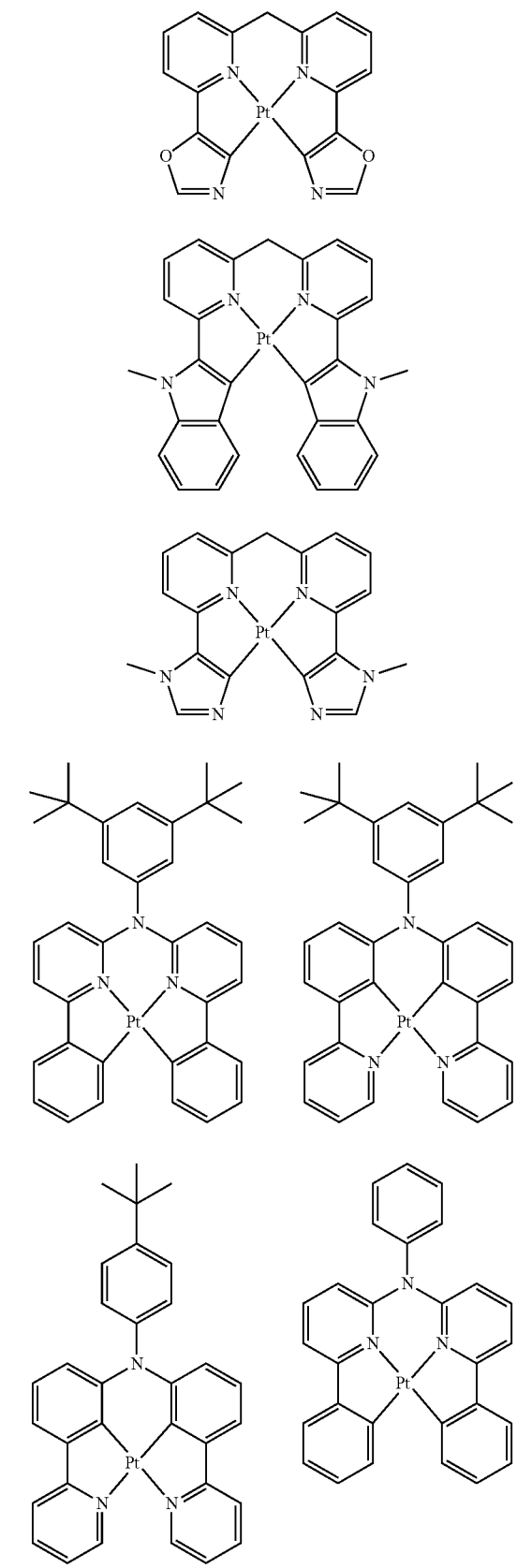

129
-continued
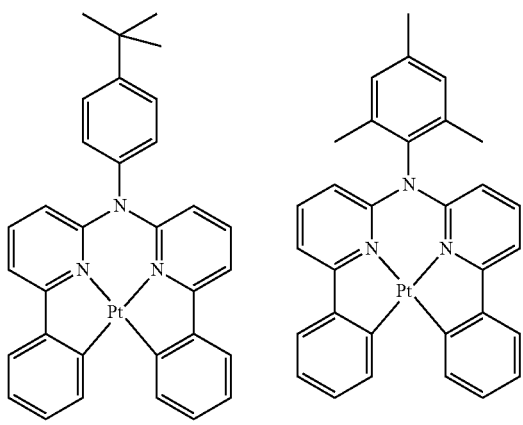
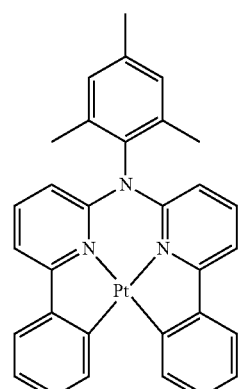
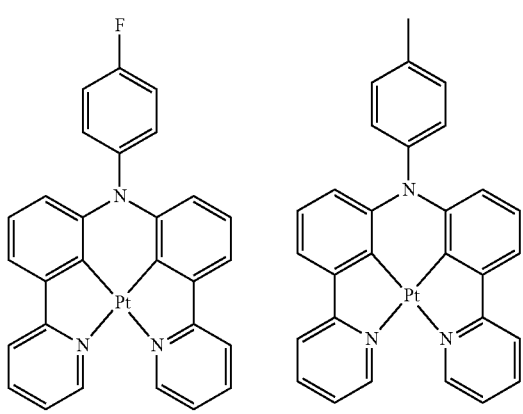
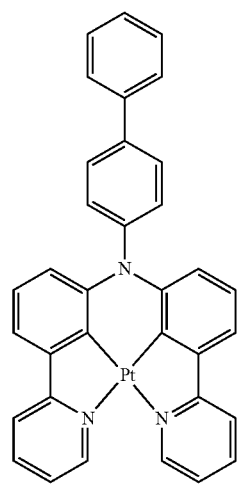
130
-continued
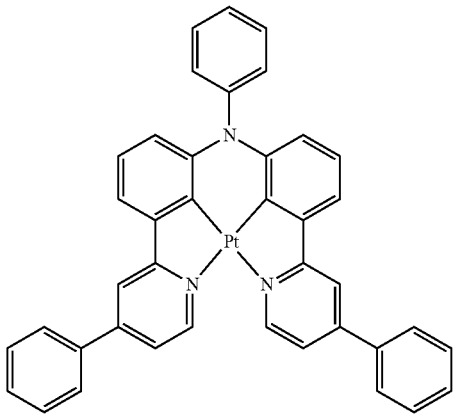
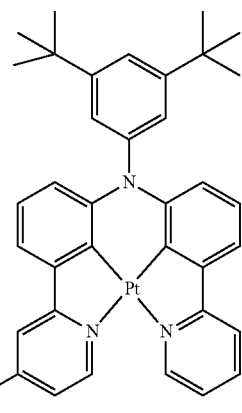
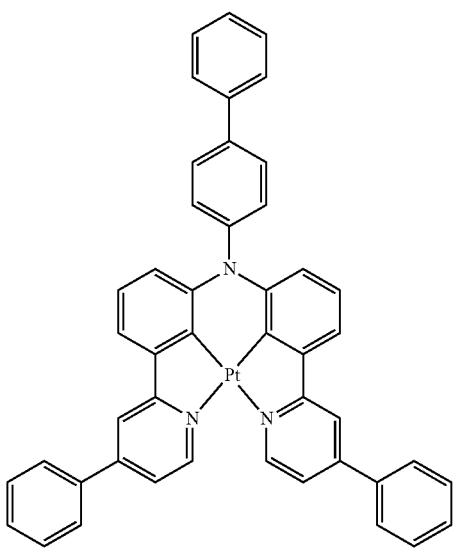

131
-continued
132
-continued
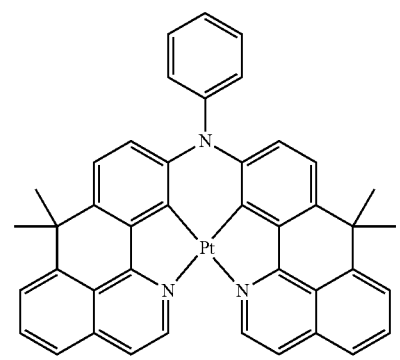
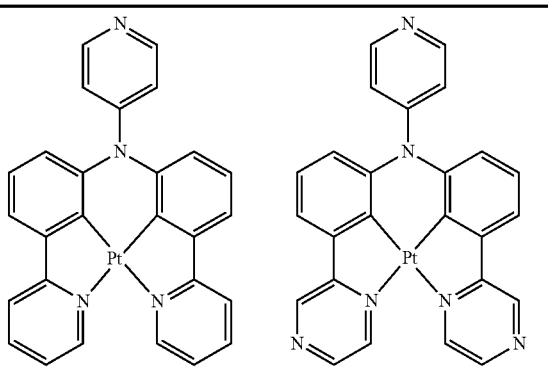
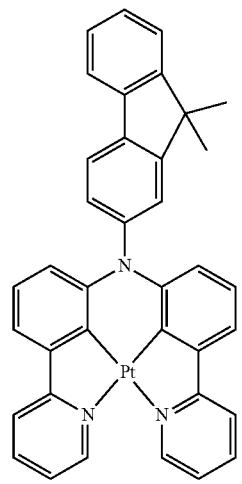
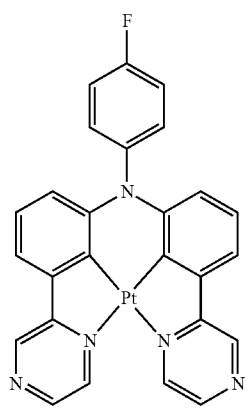
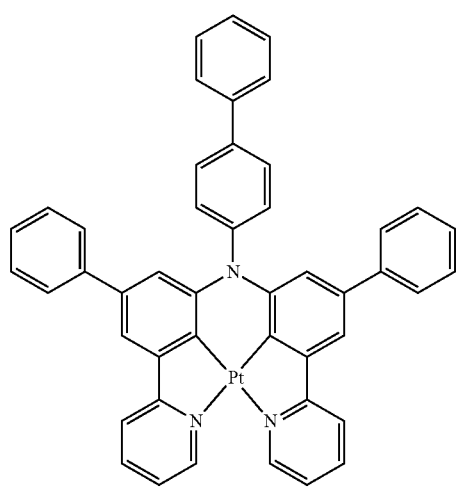
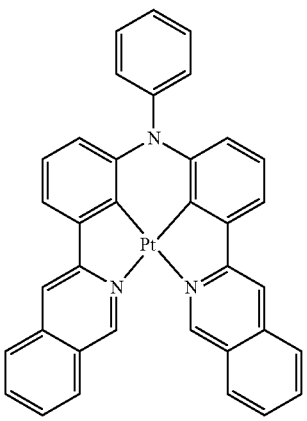
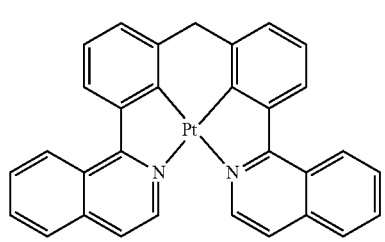

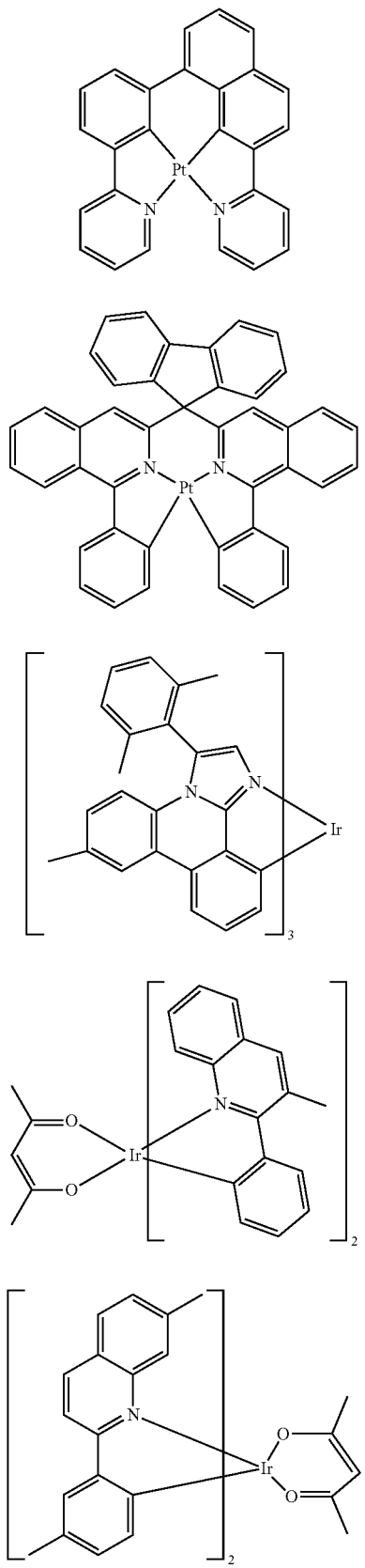
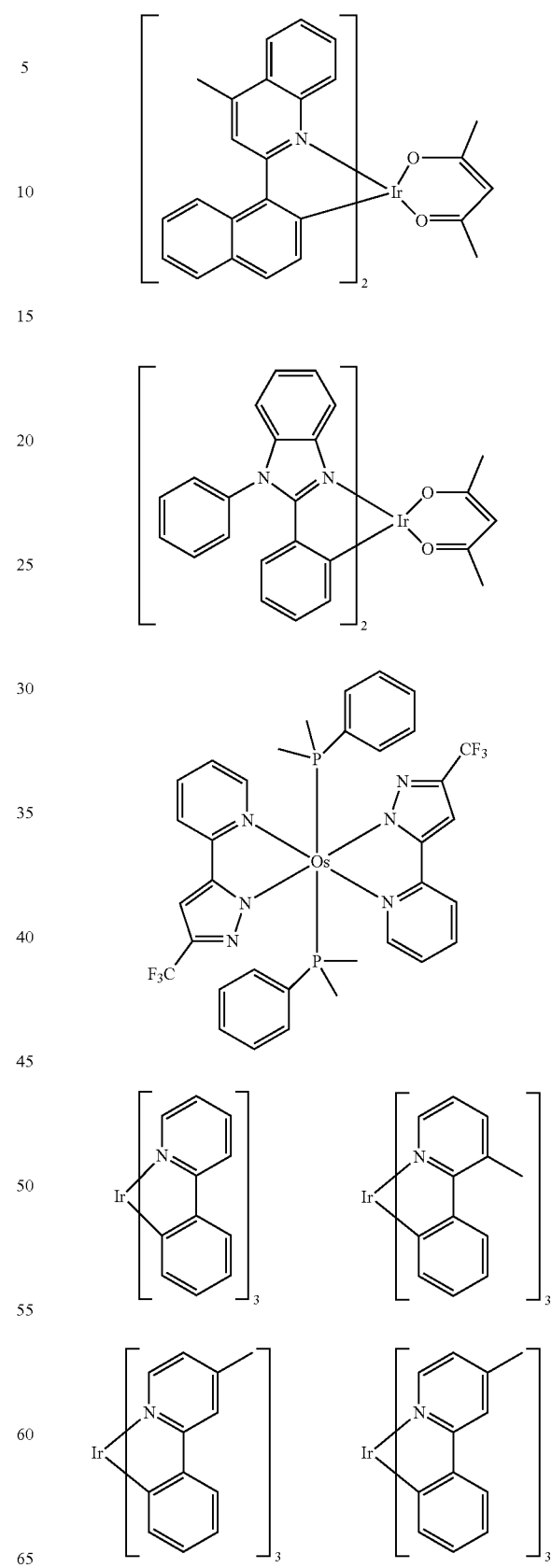

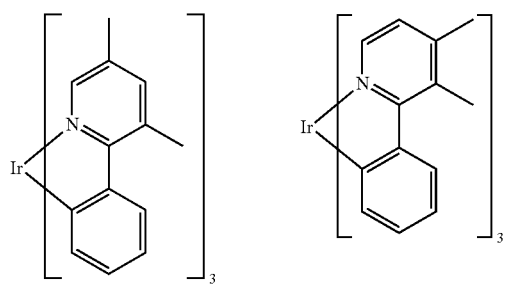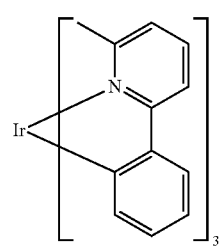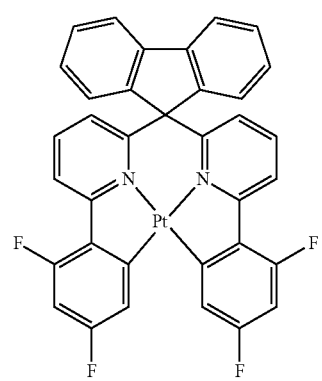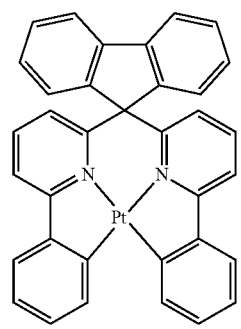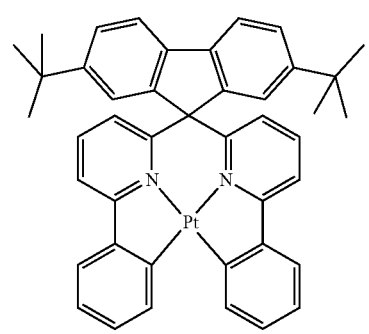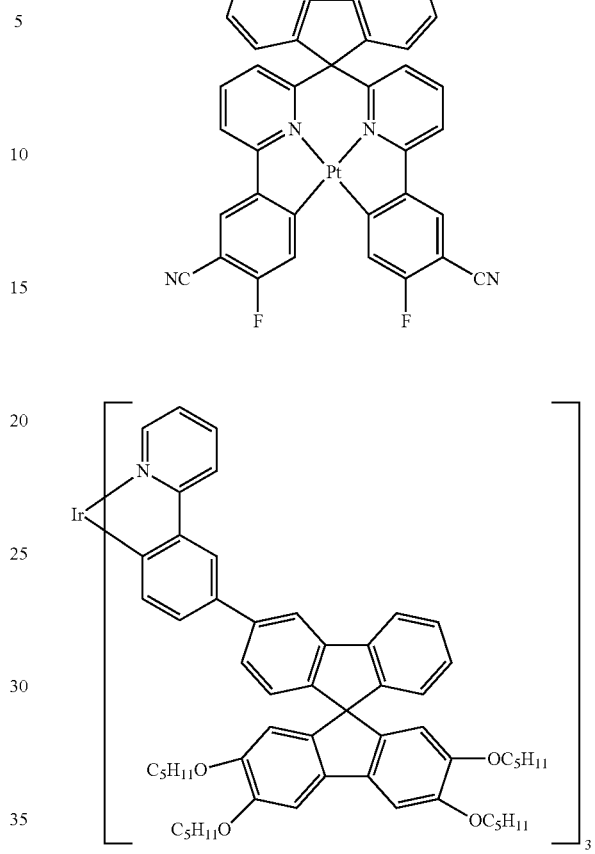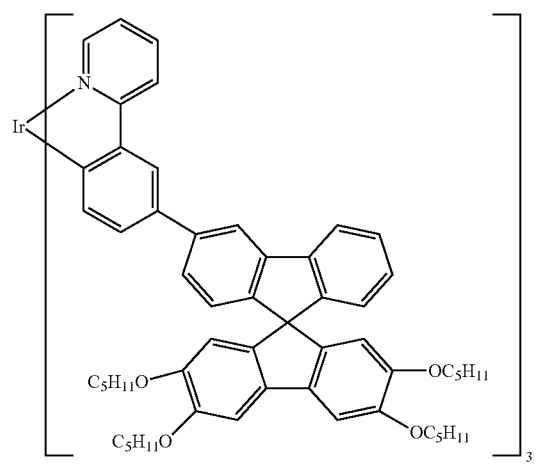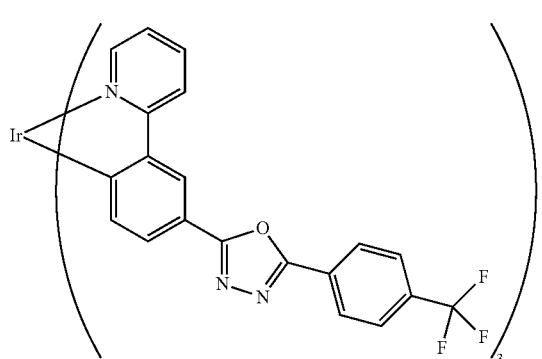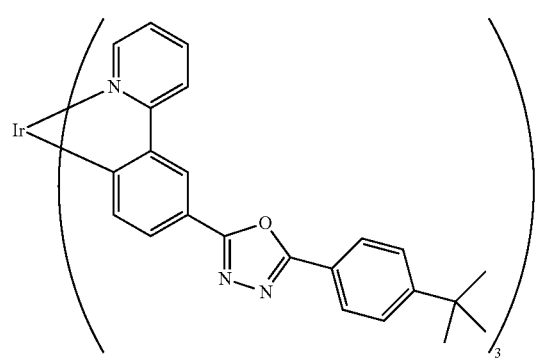

| 137 -continued | 138 -continued |
|---|---|
| 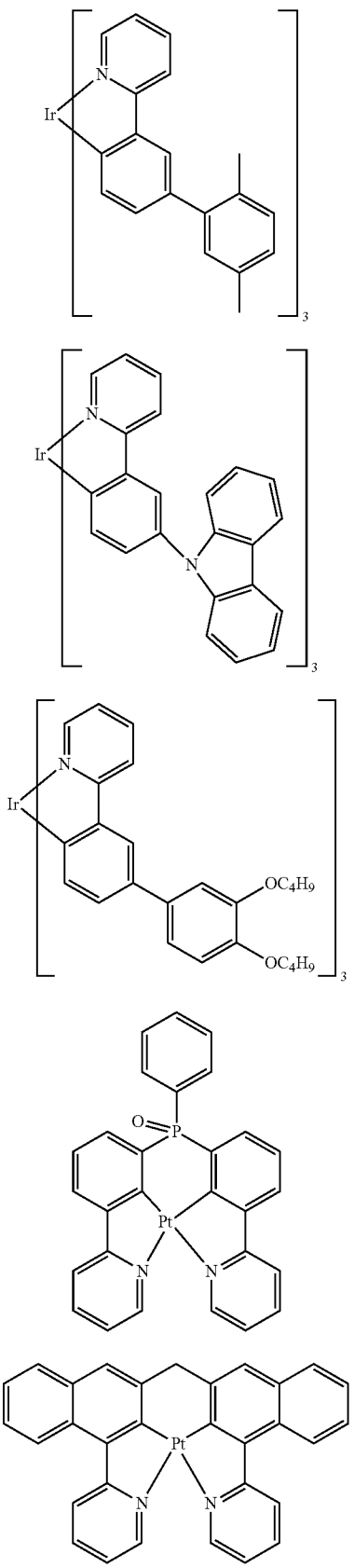 | 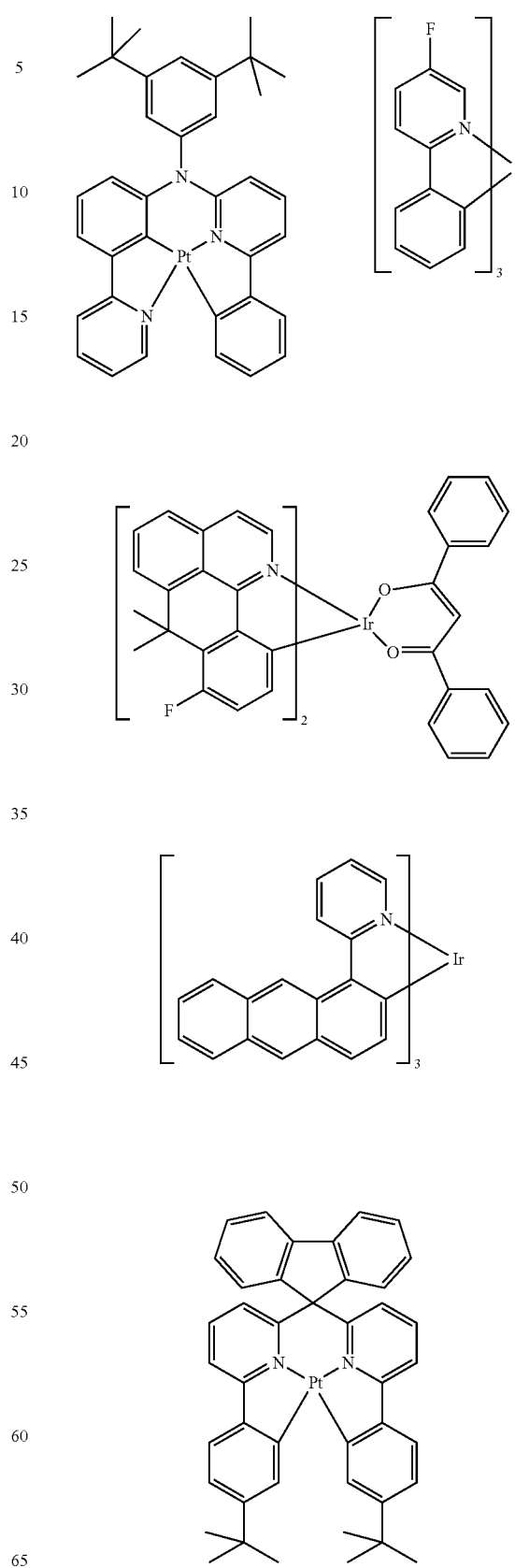 |

139
-continued
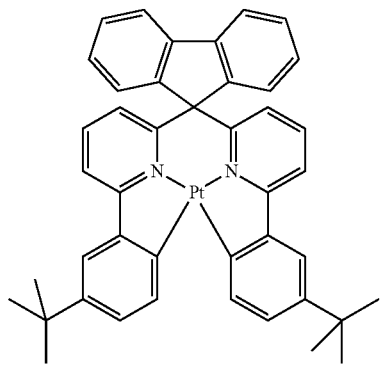
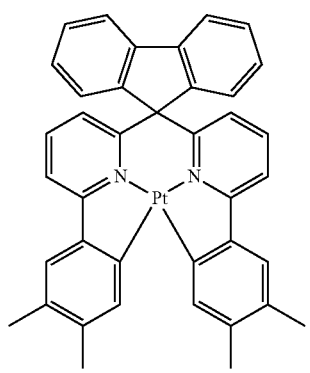
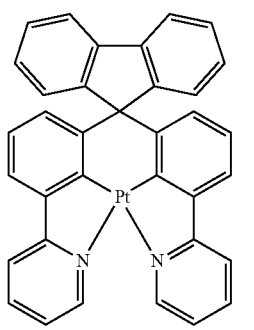 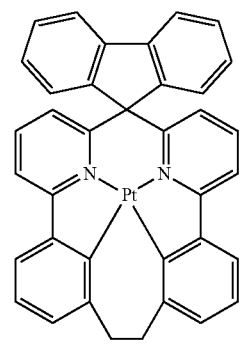
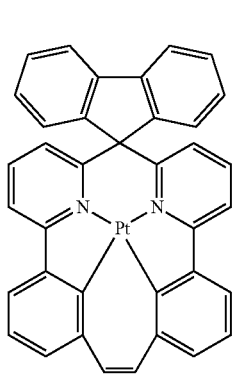 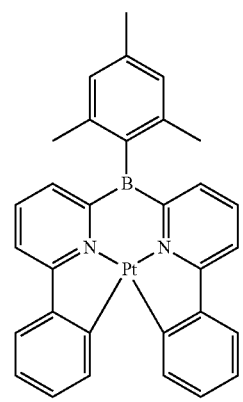
140
-continued
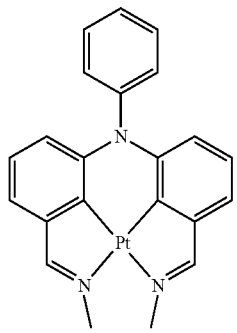
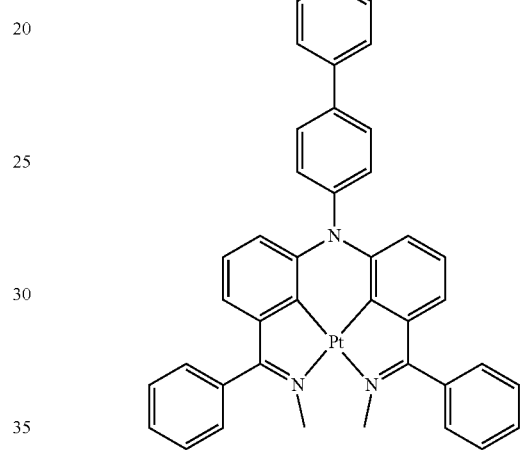
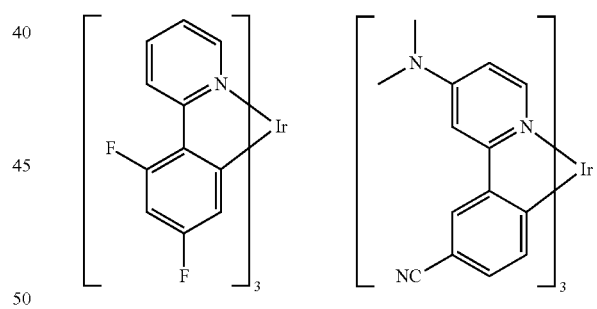
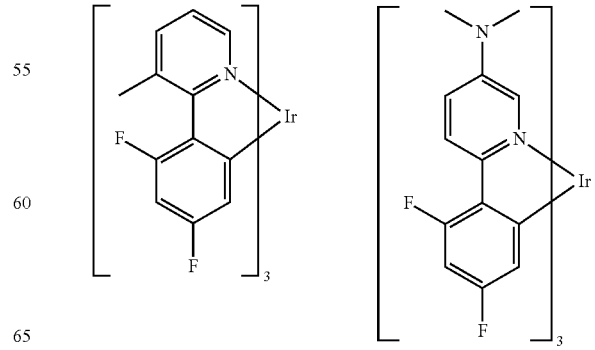

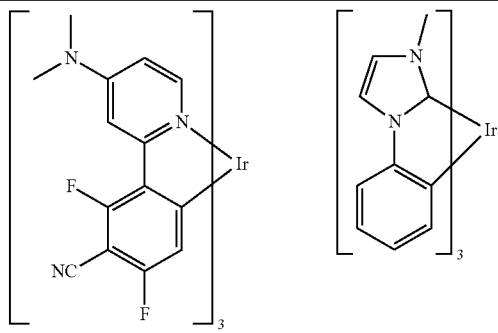
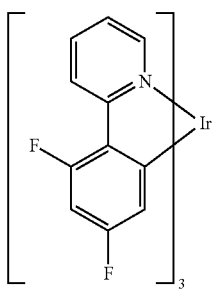
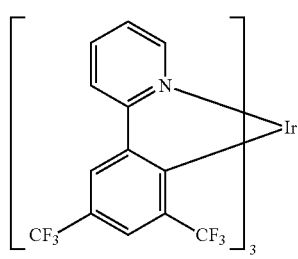
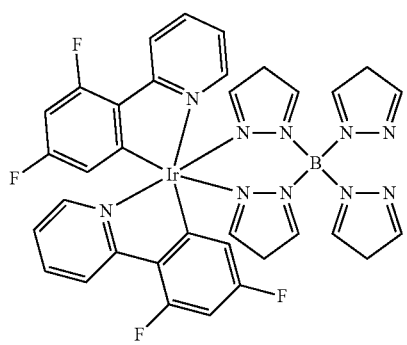
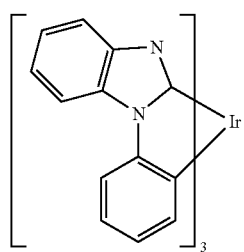
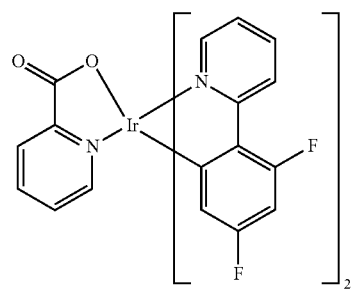
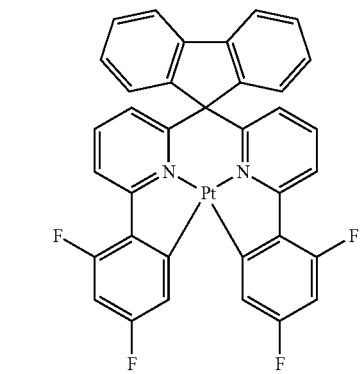
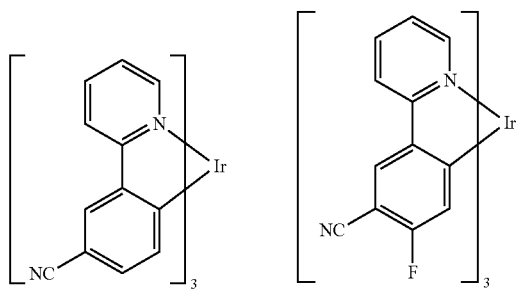
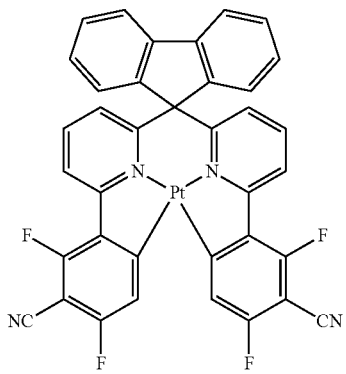

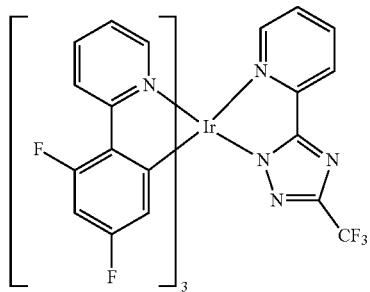
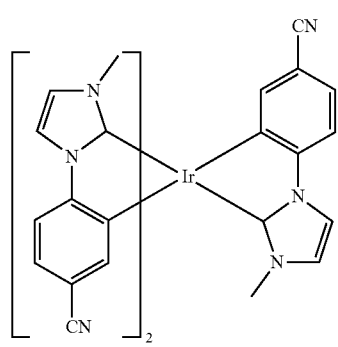
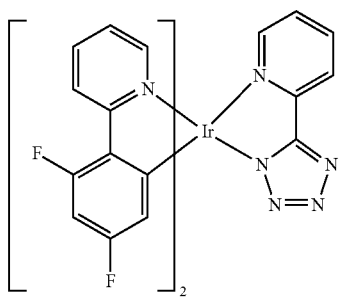
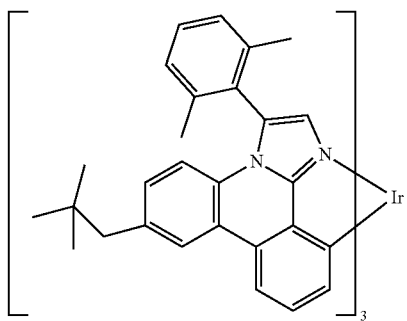
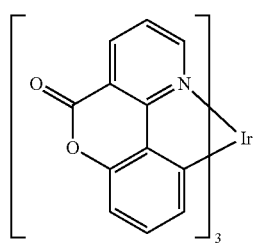
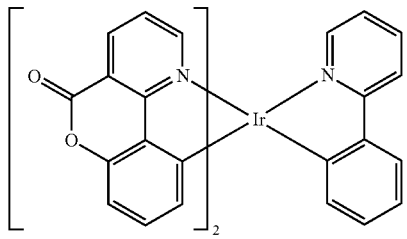
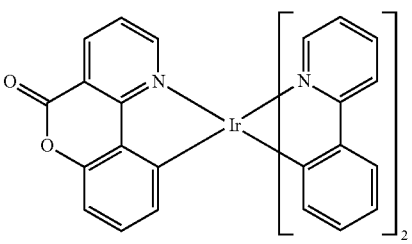
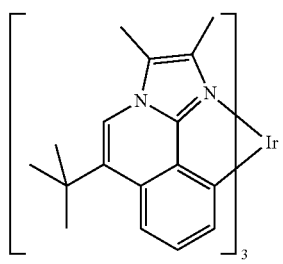
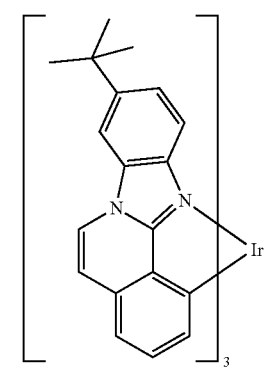
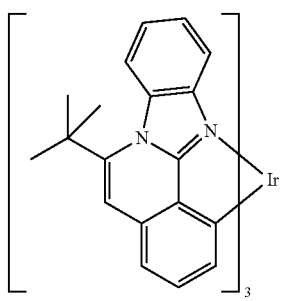

-continued

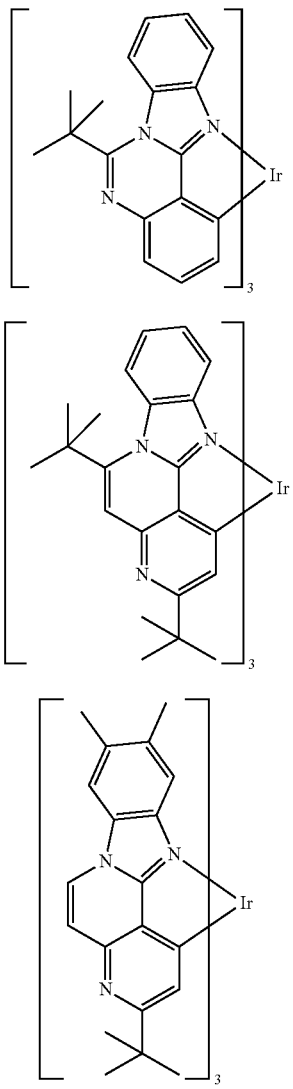

In a preferred embodiment of the invention, the compounds of the formula (1) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. If the compounds of the formula (1) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I) is used as hole-transport material in combination with a hexaazatriphenylene derivative, as described in US 2007/0092755. The hexaazatriphenylene derivative here is particularly preferably employed in a separate layer.

If the compound of the formula (1) is employed as hole-transport material in a hole-transport layer, the compound can be employed as pure material, i.e. in a proportion of 100%, in the hole-transport layer, or it can be employed in combination with one or more further compounds in the hole-transport layer.

In a further embodiment of the present invention, the compounds of the formula (1) are employed as emitting materials. To this end, the compounds are preferably employed in an emission layer. Besides at least one of the compounds of the formula (1), the emission layer furthermore comprises at least one host material. The person skilled in the art will be able to make a selection from the known host materials without difficulties and without being inventive.

In a further embodiment of the present invention, the compounds of the formula (1) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the greater.

The proportion of the matrix material in the emitting layer in this case is between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (1) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix component, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the phosphorescent dopants shown in the above table.

The materials preferably employed in the relevant functions in the devices according to the invention are indicated below.

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Suitable matrix materials, preferably for fluorescent dopants, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAIQ.

Suitable charge-transport materials, as can be used in the hole-injection or hole-transport layer or in the electron-transport layer of the organic electroluminescent device according to the invention, besides the compounds according to the invention, are, for example, the compounds disclosed in Y. Shirota et al., Chem. Rev. 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cell) or the coupling-out of light (OLED, O-LASER). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

Devices comprising the compounds of the formula (1) can be employed in a very versatile manner. Thus, for example, electroluminescent devices comprising one or more compounds of the formula (1) can be employed in displays for televisions, mobile telephones, computers and cameras. However, the devices can also be used in lighting applications. Furthermore, electroluminescent devices, for example in OLEDs or OLECs, comprising at least one of the compound of the formula (1) can be utilised for phototherapy in medicine or cosmetics. Thus, a large number of diseases (psoriasis, atopic dermatitis, inflammation, acne, skin cancer, etc.) or the prevention or reduction of skin wrinkling, skin reddening and skin ageing can be treated. Furthermore, the light-emitting devices can be utilised in order to keep drinks, meals or foods fresh or in order to sterilise equipment (for example medical equipment).

The present invention therefore also relates to an electronic device, preferably an organic electroluminescent device, very preferably an OLED or OLEC, comprising at least one compound according to the invention for phototherapeutic use in medicine, preferably for use for the treatment of skin diseases, very preferably for use for the treatment of psoriasis, atopic dermatitis, neurodermatitis, skin cancer, inflammation of the skin, jaundice (icterus) and jaundice of the newborn.

The present invention furthermore relates to the use of an electronic device, preferably an organic electroluminescent device, very preferably an OLED or OLEC, comprising at least one compound according to the invention in cosmetics, preferably for the treatment of acne, skin reddening, for the treatment of skin ageing (anti-ageing), for the reduction of skin wrinkles and for the treatment of cellulite.

The compounds according to the invention and the organic electroluminescent devices according to the invention are distinguished by the following surprising advantages over the prior art:

1. The compounds according to the invention are very highly suitable for use in a hole-transport layer or a hole-injection layer in electronic devices, such as, for example, in organic electroluminescent devices, in particular owing to their high hole mobility.

2. The compounds according to the invention have a relatively low sublimation temperature, high temperature stability and high oxidation stability and a high glass-transition temperature, which is advantageous both for the processability, for example from solution or from the gas phase, and also for use in electronic devices.

3. The use of the compounds according to the invention in electronic devices, in particular employed as hole-transport or hole-injection material, but also as light-emitting material, result in high efficiencies, low operating voltages and in long lifetimes.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies in particular to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention currently claimed.

The teaching on technical action disclosed with the present invention can be abstracted and combined with other examples.

The invention is explained in greater detail by the following examples, without wishing to restrict it thereby.

EXAMPLES
Materials
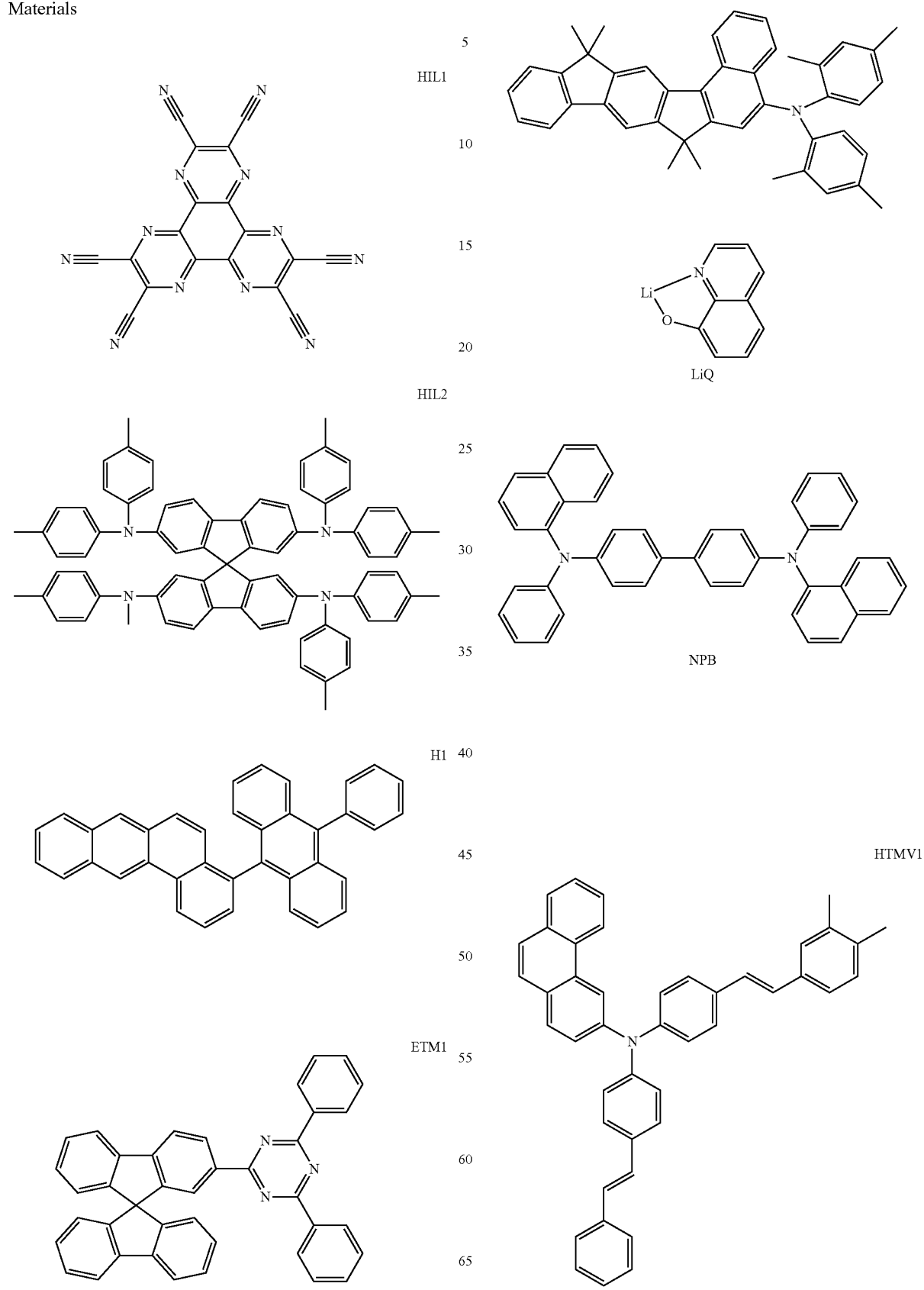

HTMV2
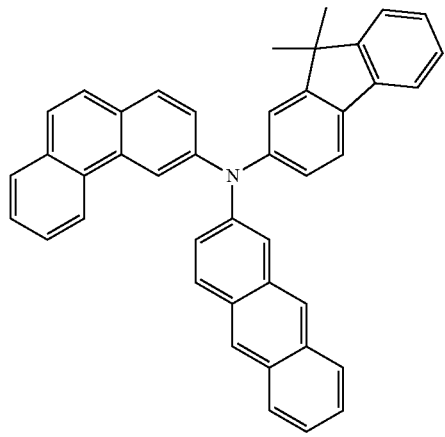
HTMV3
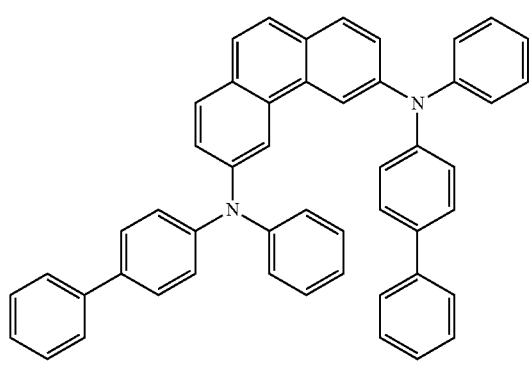
HTMV4
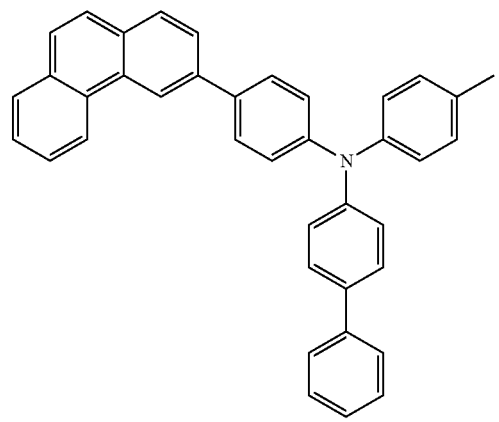
HTMV5
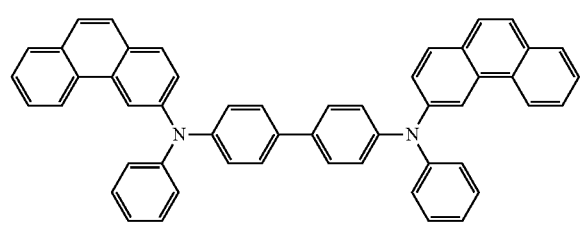
HTMV6
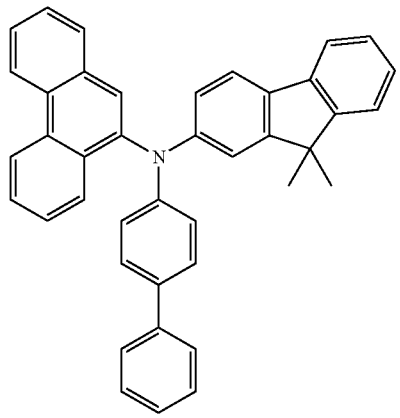
HTMV7
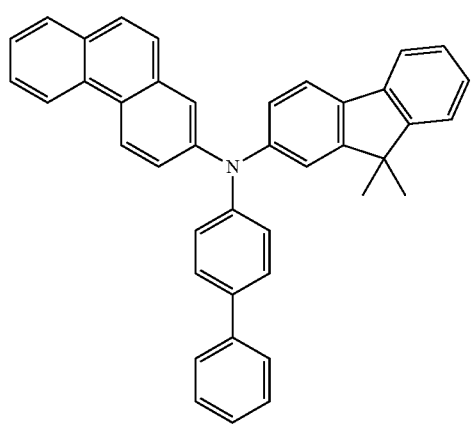
(1-9)
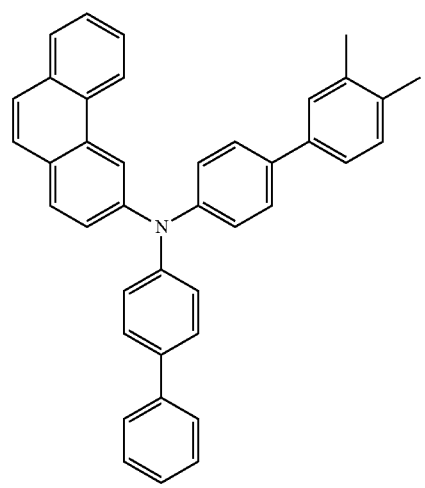

-continued
(1-1)
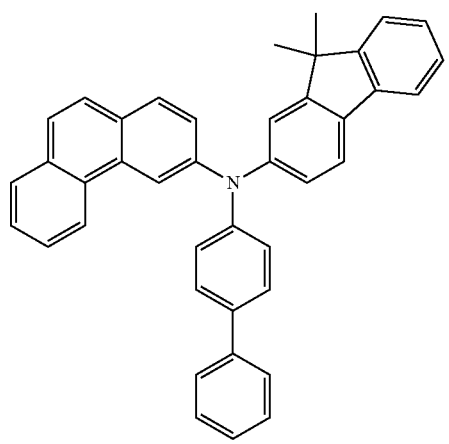
(1-11)
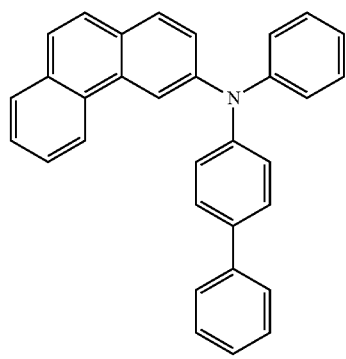
(1-12)
(2-6)
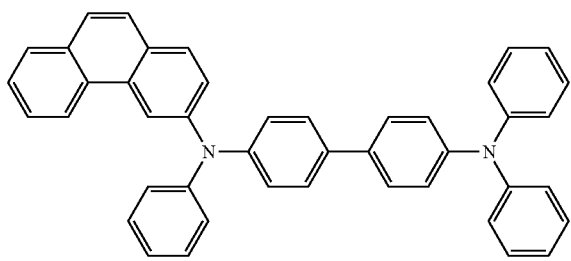
-continued
(1-2)
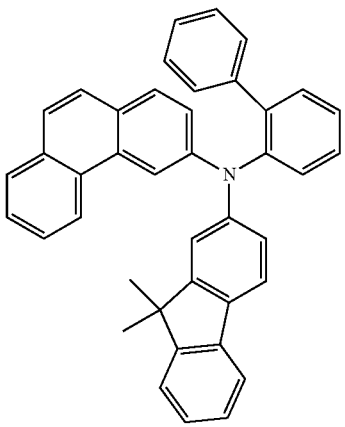
(4-1)
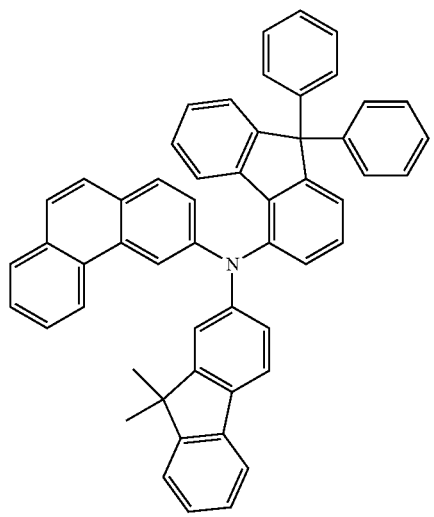
(4-4)
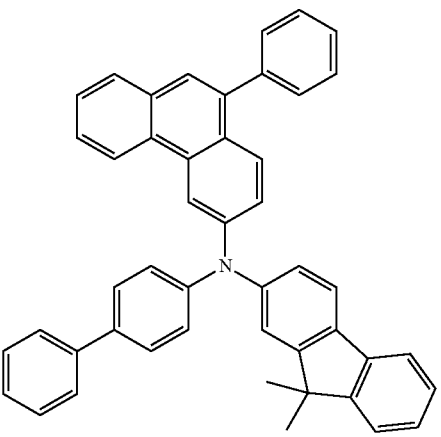
Materials HIL1, HIL2 (EP 0676461), H1 (WO 2008/145239), ETM1 (WO 2005/053055), SEB1 (WO 2008/006449), LiQ and NPB are well known to the person skilled in the art. Their properties and syntheses are known from the prior art. Compounds (1-9), (1-1), (1-11), (1-12), (2-6) (1-2) and (4-1) are according to the invention.

Example 1

Synthesis of biphenyl-4-yl-(9,9-dimethyl-9H-fluoren-2-yl)phenanthren-3-ylamine (1-1)

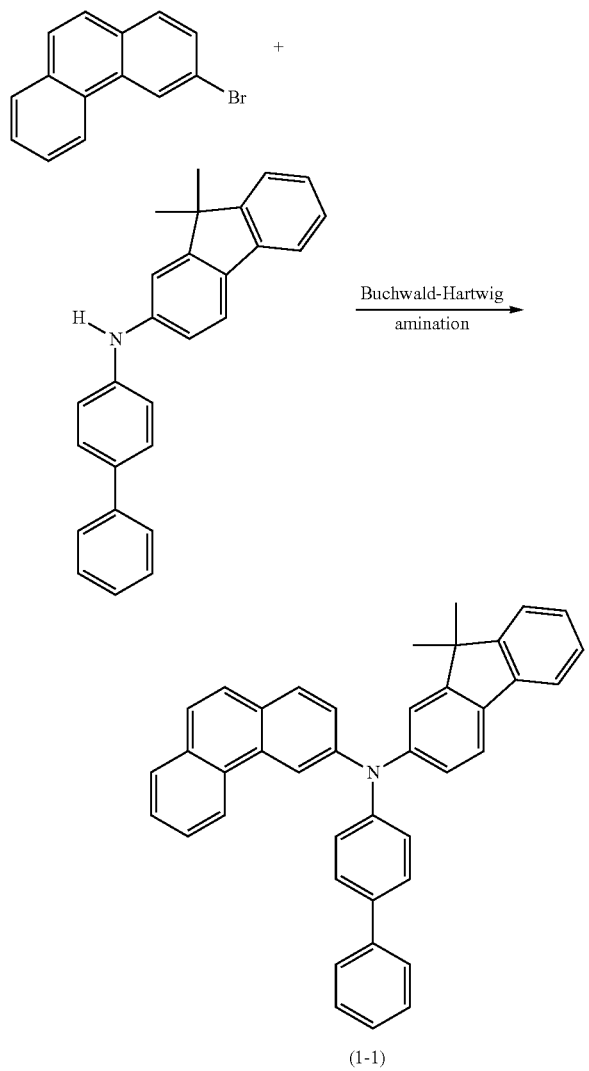

(1-1)

Synthesis of Starting Material 3-bromophenanthrene

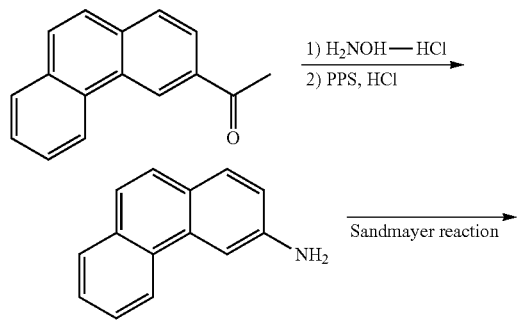

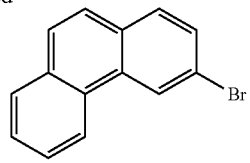

Synthesis of 3-aminophenanthrene 50 g (227 mmol) of 3-acetylphenenthrene and 63.8 ml of pyridine (790 mmol) and 42 g (592 mmol) of hydroxylammonium chloride are dissolved in 300 ml of EtOH. The batch is heated to 75° C. After reaction for 1 h, the batch is cooled. The mixture is subsequently partitioned between ethyl acetate and water, the organic phase is washed three times with water and dried over $Na_2SO_4$ and concentrated in a rotary evaporator. 300 ml of polyphosphoric acid are carefully added to the concentrated solution, and the mixture is heated at 75° C. for 1 h. The batch is then cooled to room temperature, and carefully poured with ice-water (300 ml). The precipitated solid is filtered off with suction and rinsed with methanol. Finally, 800 ml of MeOH and 70 ml of conc. HCl are added to the solid. The reaction mixture is heated at the boil for 8 h. The mixture is subsequently neutralised using sodium hydroxide solutions, partitioned between etyl acetate and water, the organic phase is washed three times with water and dried over $Na_2SO_4$ and evaporated in a rotary evaporator. The residue was dried at 40° C. in vacuo. Yield 35.5 g (184 mmol) (81% of theory)

Synthesis of 3-bromophenanthrene 30 g (155 mmol) of 3-aminophenanthrene and 36.7 g of $CuBr_2$ (155 mmol) are dissolved in 300 ml of dried acetonitrile. 40.4 ml of tert-butyl nitrite (535 mmol) are added in portions at 0° C. The suspension is stirred for a further 1 h and then poured onto 400 ml of ice-water and stirred for about 20 min. The precipitated solid is filtered off with suction, dissolved in dichloromethane and washed a number of times with water. The organic phase is evaporated in a rotary evaporator and recrystallised from toluene/heptane. Yield: 21.9 g (85 mmol) (55% of theory)

Other halogenated phenanthrenes as starting compounds can be prepared analogously.

| Starting material 1 | Starting material 2 | Product | Yield |
|---|---|---|---|
| 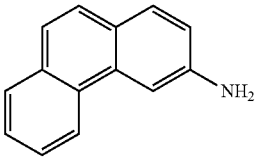 [SMILES: Nc1ccc2ccc3ccccc3c2c1] | CuI$_2$ | 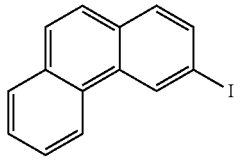 [SMILES: Ic1ccc2ccc3ccccc3c2c1] | 45% |
| 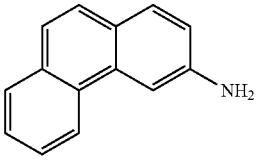 [SMILES: Nc1ccc2ccc3ccccc3c2c1] | CuCl$_2$ | 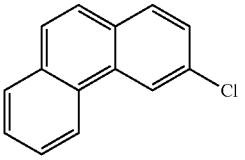 [SMILES: Clc1ccc2ccc3ccccc3c2c1] | 50% |

Synthesis of Compound (1-1)

28.1 g (78 mmol) of biphenyl-4-yl-(9,9-dimethyl-9H-fluoren-2-yl)amines, 20.0 g (78 mol) of 3-bromophenanthrenes are dissolved in 600 ml of toluene: The solution is degassed and saturated with N$_2$. 3.1 ml (3.11 mmol) of a tri-tert-butylphosphine solution and 0.35 g (1.56 mmol) of palladium(II) acetate are then added, and 11.6 g of sodium tert-butoxide (116.7 mmol) are subsequently added. The reaction mixture is heated at the boil under a protective atmosphere for 5 h. The mixture is subsequently partitioned between toluene and water, the organic phase is washed three times with water and dried over Na$_2$SO$_4$ and evaporated in a rotary evaporator. After filtration of the crude product through silica gel with toluene, the residue which remains is recrystallised from heptane/toluene and finally sublimed in a high vacuum, purity is 99.9% (HPLC). The yield of compound (1-1) is 29.6 g (71% of theory).

Examples 2-12

Synthesis of Compounds (1-2) to (1-12)

The following compounds (1-2) to (1-12) are also prepared analogously to the synthesis of compound (1-1) described in Example 1.

| | Starting material 1 | Starting material 2 | Product | Yield |
|---|---|---|---|---|
| 1-2 | 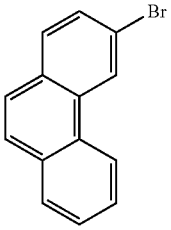 | 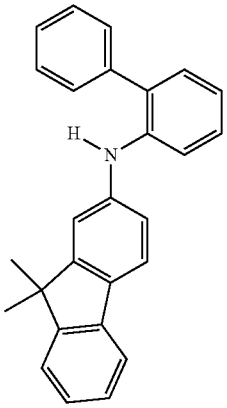 [SMILES: CC1(C)c2ccccc2-c2ccc(Nc3ccccc3-c3ccccc3)cc21] | 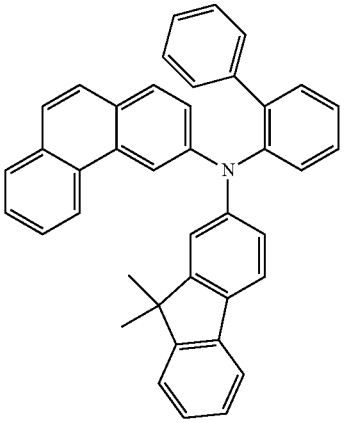 [SMILES: CC1(C)c2ccccc2-c2ccc(N(c3ccc4ccc5ccccc5c4c3)c3ccccc3-c3ccccc3)cc21] | 78% |

-continued
| Starting material 1 | Starting material 2 | Product | Yield |
|---|---|---|---|
| 1-3 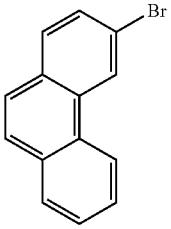 | 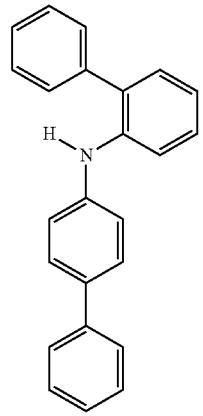 [SMILES: c1ccc(-c2ccc(Nc3ccccc3-c3ccccc3)cc2)cc1] | 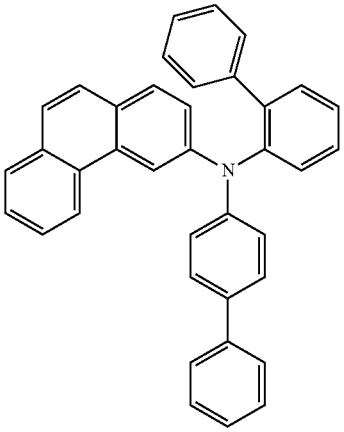 [SMILES: c1ccc(-c2ccc(N(c3ccc4ccc5ccccc5c4c3)c3ccccc3-c3ccccc3)cc2)cc1] | 82% |
| 1-4 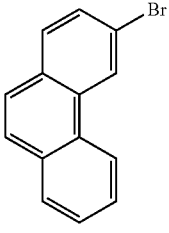 | 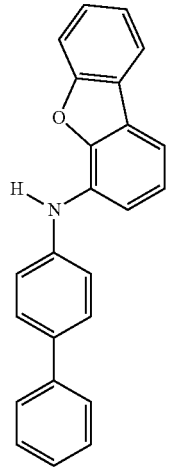 [SMILES: c1ccc(-c2ccc(Nc3cccc4c3oc3ccccc34)cc2)cc1] | 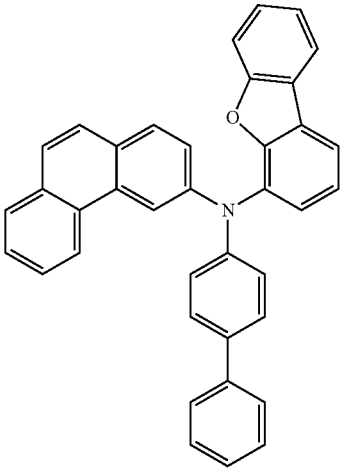 [SMILES: c1ccc(-c2ccc(N(c3ccc4ccc5ccccc5c4c3)c3cccc4c3oc3ccccc34)cc2)cc1] | 88% |
| 1-5 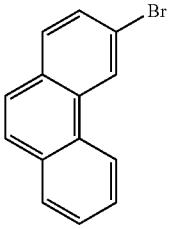 [SMILES: Brc1ccc2ccc3ccccc3c2c1] | 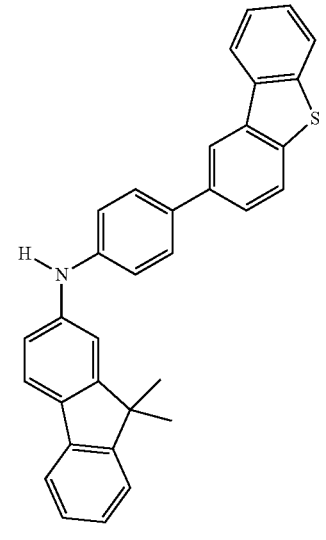 [SMILES: CC1(C)c2ccccc2-c2ccc(Nc3ccc(-c4ccc5sc6ccccc6c5c4)cc3)cc21] | 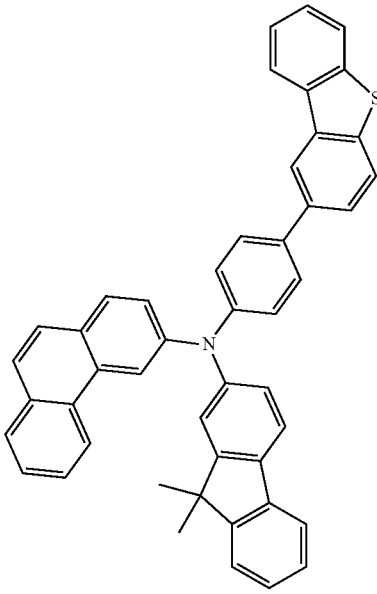 [SMILES: CC1(C)c2ccccc2-c2ccc(N(c3ccc(-c4ccc5sc6ccccc6c5c4)cc3)c3ccc4ccc5ccccc5c4c3)cc21] | 67% |

-continued
| Starting material 1 | Starting material 2 | Product | Yield |
|---|---|---|---|
| 1-6 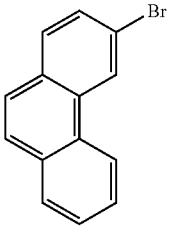 [SMILES: Brc1ccc2ccc3ccccc3c2c1] | 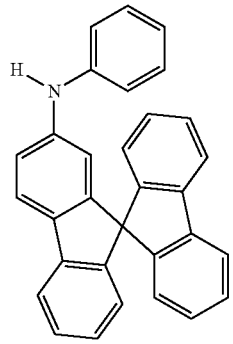 [SMILES: c1ccc(Nc2ccc3c(c2)C2(c4ccccc4-c4ccccc42)c2ccccc2-3)cc1] | 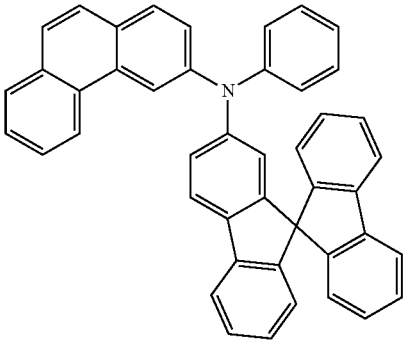 [SMILES: c1ccc(N(c2ccc3c(c2)C2(c4ccccc4-c4ccccc42)c2ccccc2-3)c2ccc3ccc4ccccc4c3c2)cc1] | 76% |
| 1-7 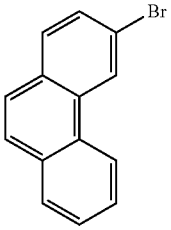 | 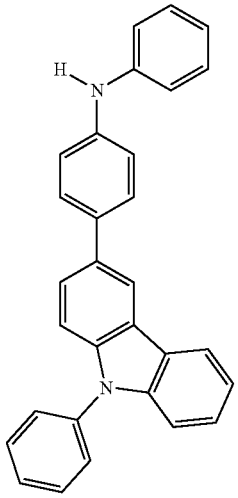 [SMILES: c1ccc(Nc2ccc(-c3ccc4c(c3)c3ccccc3n4-c3ccccc3)cc2)cc1] | 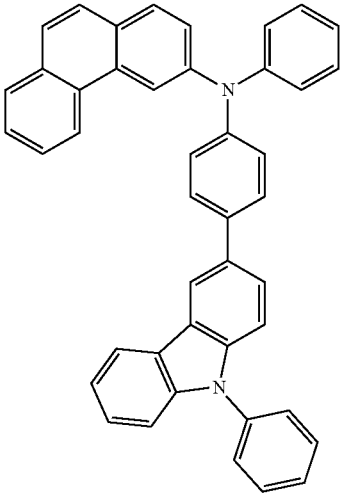 [SMILES: c1ccc(N(c2ccc(-c3ccc4c(c3)c3ccccc3n4-c3ccccc3)cc2)c2ccc3ccc4ccccc4c3c2)cc1] | 80% |
| 1-8 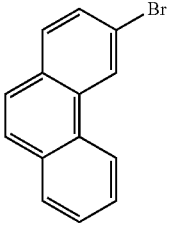 [SMILES: Brc1ccc2ccc3ccccc3c2c1] | 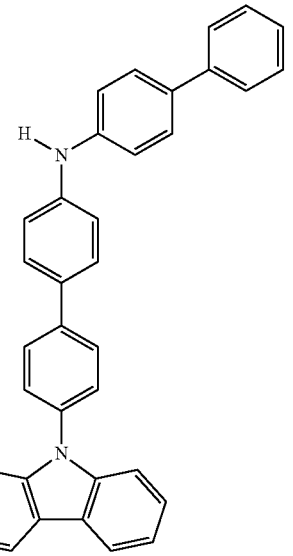 | 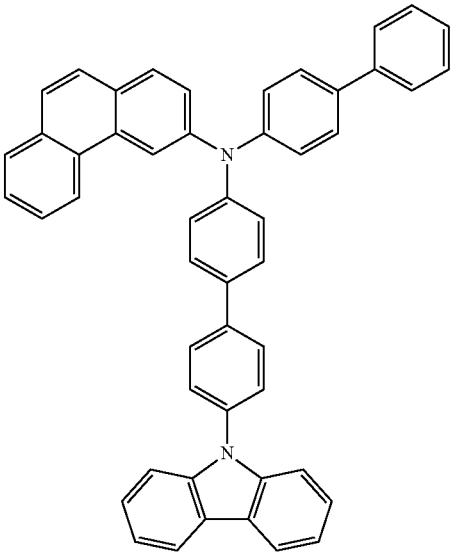 [SMILES: c1ccc(-c2ccc(N(c3ccc(-c4ccc(-n5c6ccccc6c6ccccc65)cc4)cc3)c3ccc4ccc5ccccc5c4c3)cc2)cc1] | 75% |

-continued

| | Starting material 1 | Starting material 2 | Product | Yield |
|---|---|---|---|---|
| 1-9 | | | | 70% |
| 1-10 | | | | 67% |
| 1-11 | | | | 72% |
| 1-12 | | | | 65% |

The following comparative compounds (HTMV1) to (HTMV3) and (HTMV6) to (HTMV7) are also prepared analogously to the synthesis of compound (1-1) described in Example 1.
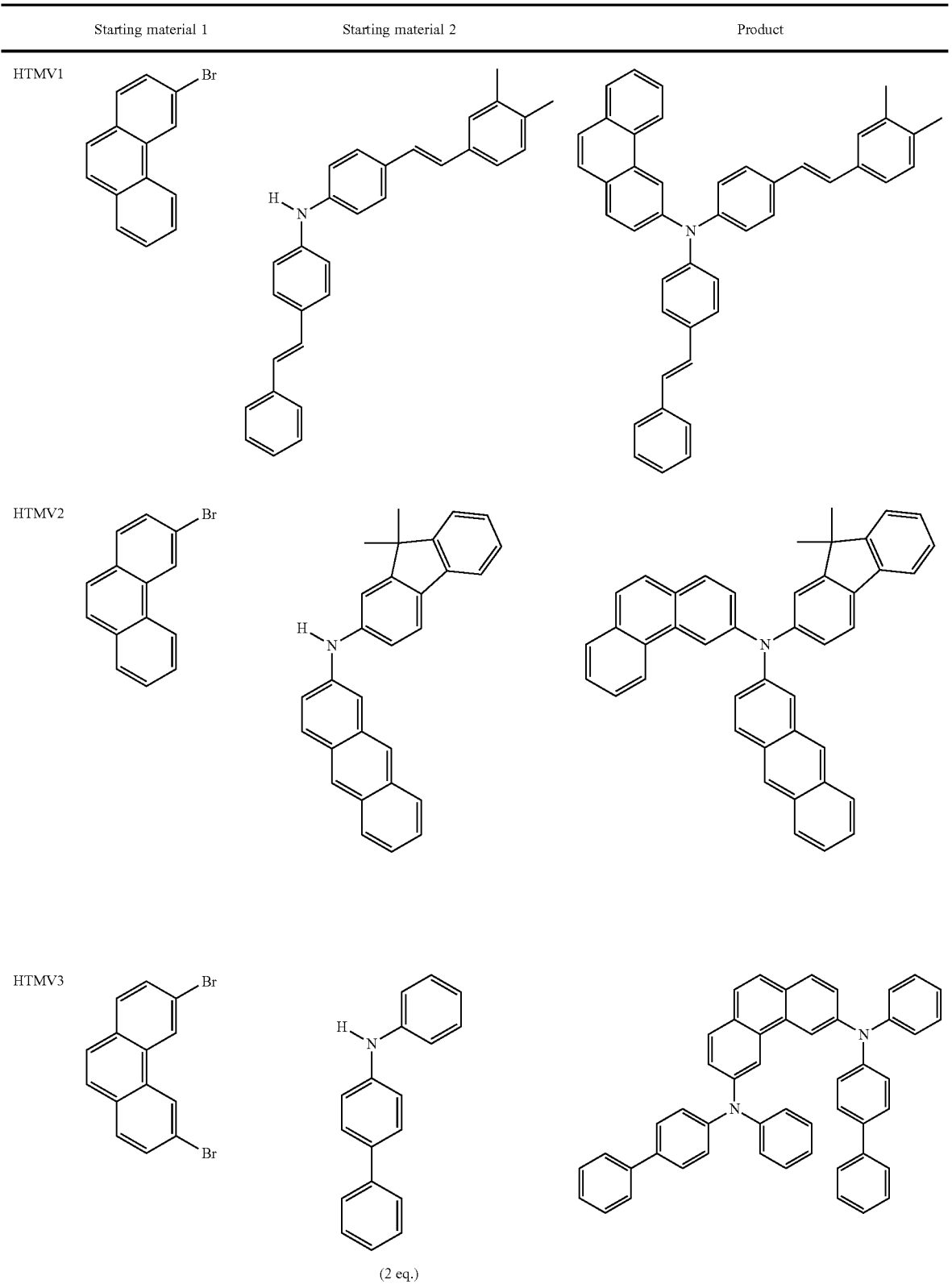

-continued
| Starting material 1 | Starting material 2 | Product |
|---|---|---|
| HTMV6 | | |
| HTMV7 | | |
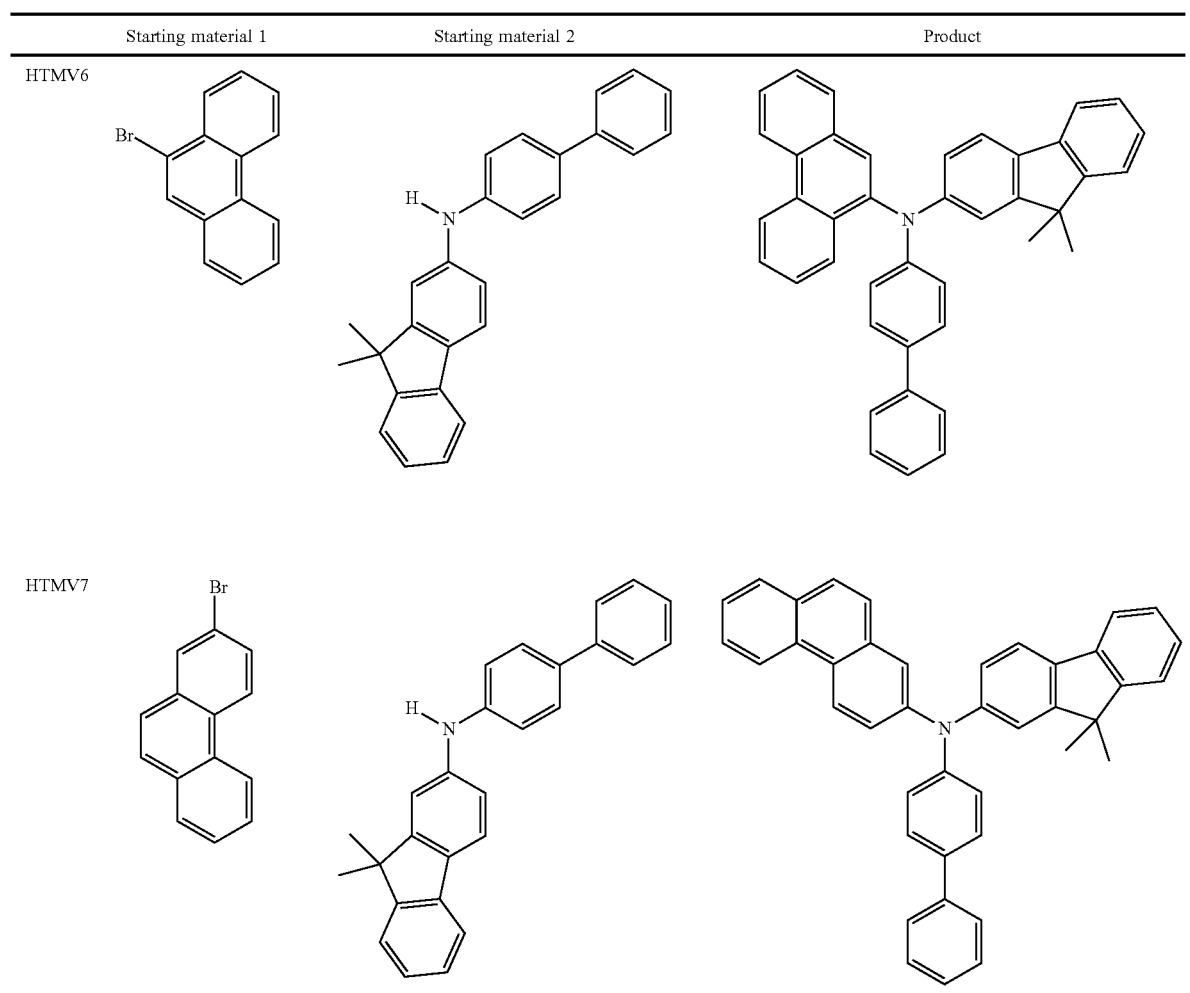
Examples 13
Synthesis of the Compound N*4'-biphenyl-4-yl-N*4'*-dibenzofuran-4-yl-N*4-phenanthren-3-yl-N*4*-phenylbiphenyl-4,4'-damine (2-1)
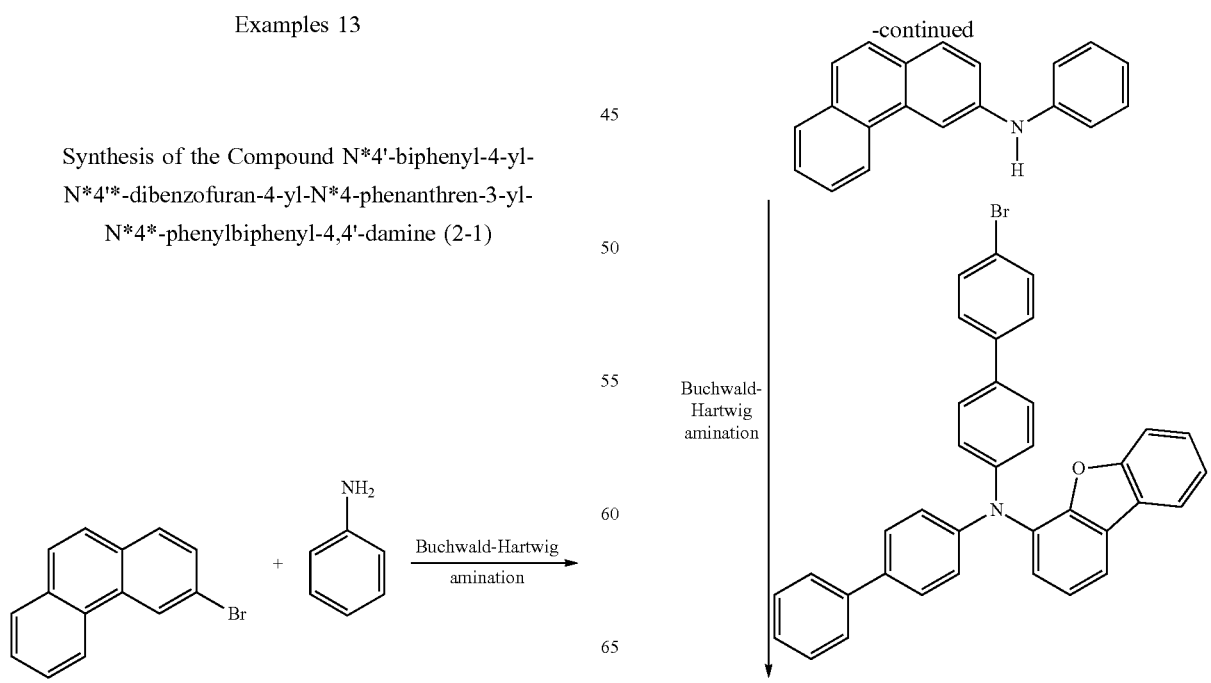

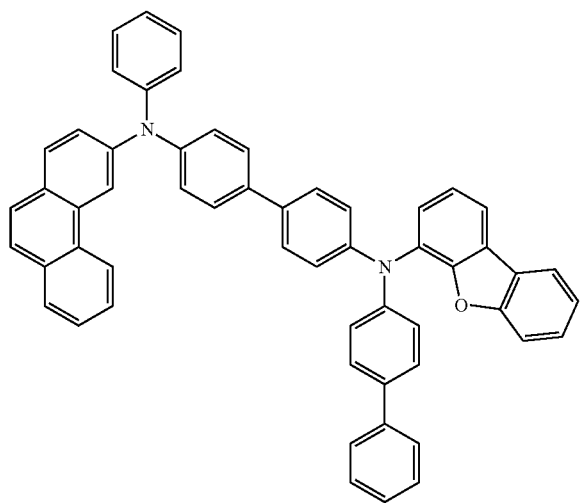

(2-1)

10 g of phenanthren-3-ylphenylamines (37 mmol), 21 g. of biphenyl-4-yl-(4'-bromobiphenyl-4-yl)dibenzofuran-4-ylamines (37 mol) are dissolved in 500 ml of toluene: The solution is degassed and saturated with $N_2$. 1.5 ml (1.5 mmol) of a tri-tert-butylphosphine solution and 0.17 g (0.74 mmol) of palladium(II) acetate are then added, and 5.6 g of sodium tert-butoxide (56 mmol) are subsequently added. The reaction mixture is heated at the boil under a protective atmosphere for 3 h. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene and finally sublimed in a high vacuum, purity is 99.9% (HPLC). The yield is 16.8 g (60% of theory).

Examples 14-18

Synthesis of Compounds (2-2) to (2-6)

The following compounds (2-2) to (2-6) are also prepared analogously to the synthesis of compound (2-1) described in Example 13.

| | Starting material 1 | Startinh material 2 |
|---|---|---|
| 2-2 | | |
| 2-3 | | |

-continued
2-4
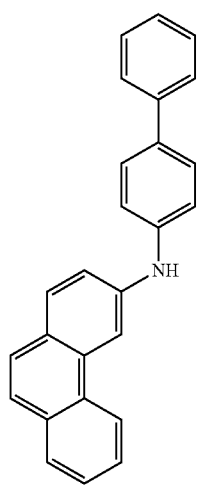 [SMILES: c1ccc(-c2ccc(Nc3ccc4ccc5ccccc5c4c3)cc2)cc1] 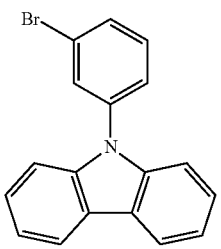 [SMILES: Brc1cccc(-n2c3ccccc3c3ccccc32)c1]
2-5
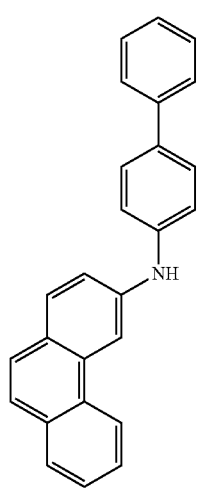 [SMILES: c1ccc(-c2ccc(Nc3ccc4ccc5ccccc5c4c3)cc2)cc1] 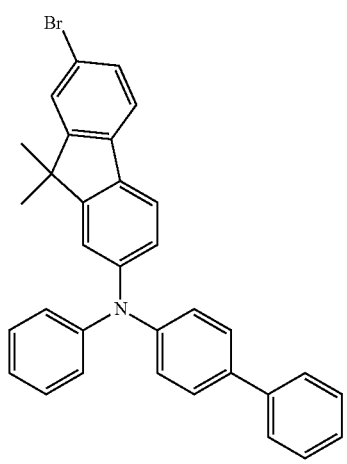 [SMILES: CC1(C)c2cc(Br)ccc2-c2ccc(N(c3ccccc3)c3ccc(-c4ccccc4)cc3)cc21]
2-6
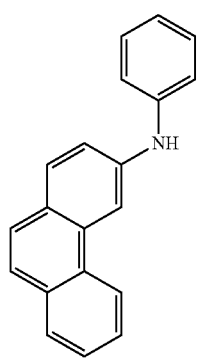 [SMILES: c1ccc(Nc2ccc3ccc4ccccc4c3c2)cc1] 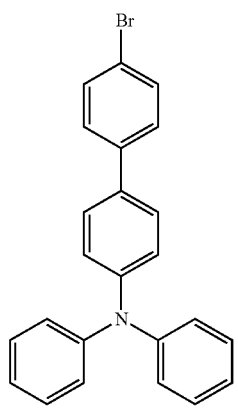 [SMILES: Brc1ccc(-c2ccc(N(c3ccccc3)c3ccccc3)cc2)cc1]

-continued
| | Product | Yield |
|---|---|---|
| 2-2 | 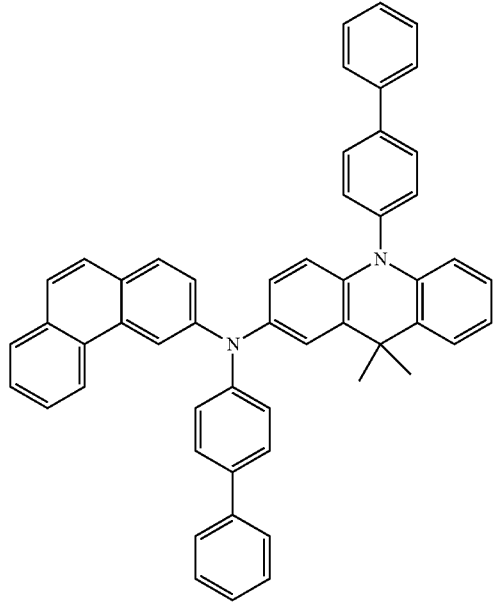 [SMILES: CC1(C)c2ccccc2N(c2ccc(-c3ccccc3)cc2)c2ccc(N(c3ccc(-c4ccccc4)cc3)c3ccc4ccc5ccccc5c4c3)cc21] | 55% |
| 2-3 | 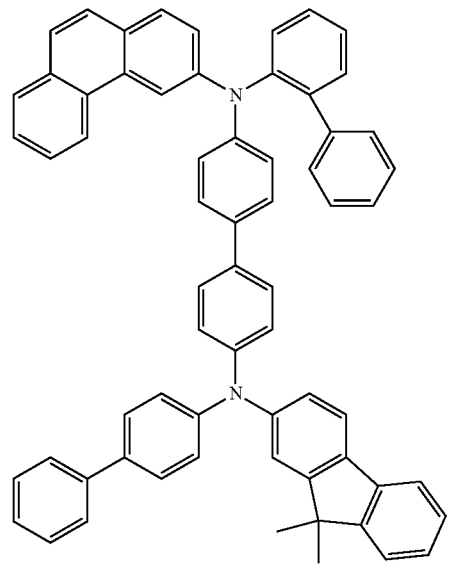 [SMILES: CC1(C)c2ccccc2-c2ccc(N(c3ccc(-c4ccccc4)cc3)c3ccc(-c4ccc(N(c5ccc6ccc7ccccc7c6c5)c5ccccc5-c5ccccc5)cc4)cc3)cc21] | 62% |

-continued
| | | |
|---|---|---|
| 2-4 | 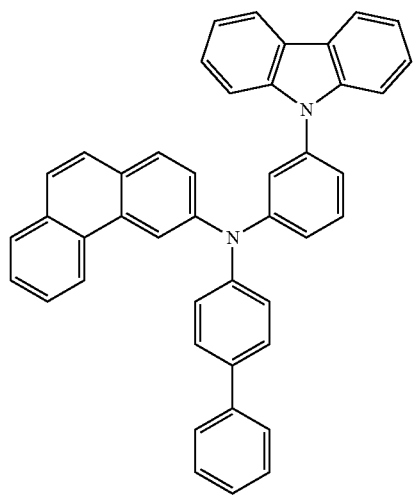 [SMILES: c1ccc(-c2ccc(N(c3cccc(-n4c5ccccc5c5ccccc54)c3)c3ccc4ccc5ccccc5c4c3)cc2)cc1] | 65% |
| 2-5 | 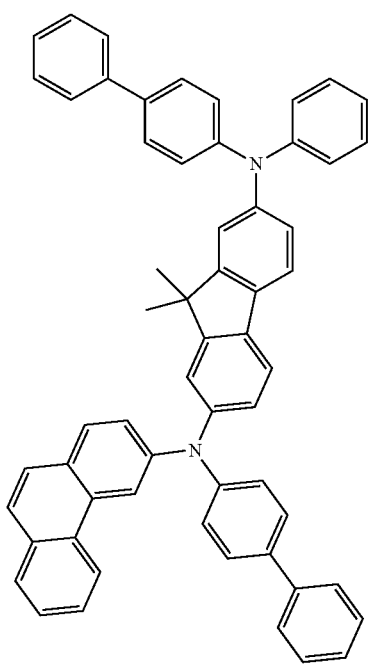 [SMILES: CC1(C)c2cc(N(c3ccccc3)c3ccc(-c4ccccc4)cc3)ccc2-c2ccc(N(c3ccc(-c4ccccc4)cc3)c3ccc4ccc5ccccc5c4c3)cc21] | 65% |
| 2-6 | 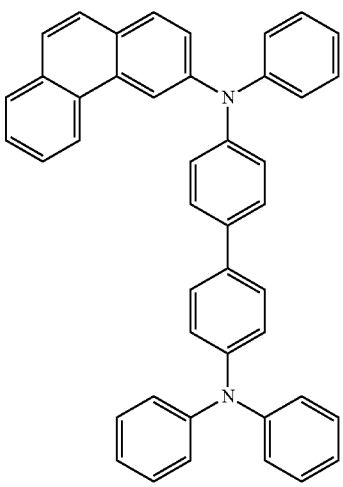 [SMILES: c1ccc(N(c2ccccc2)c2ccc(-c3ccc(N(c4ccccc4)c4ccc5ccc6ccccc6c5c4)cc3)cc2)cc1] | 60% |

The comparative compound (HTMV5) is also prepared analogously to the synthesis of compound (2-1) described in Example 13.
| Starting material 1 | Starting material 2 | Product |
|---|---|---|
| HTMV5 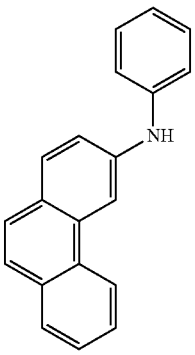 (2 eq) | 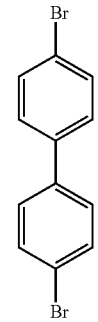 | 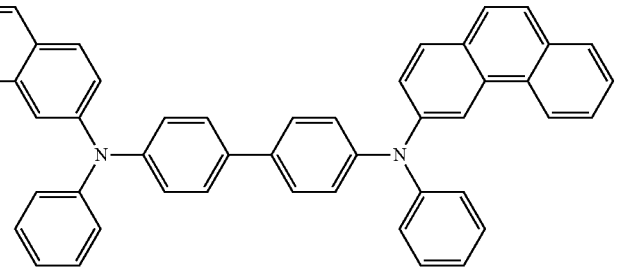 |
Examples 19
Synthesis of the Compound biphenyl-4-ylbiphenyl-2-yl-(9,9-dimethyl-7-phenanthren-3-yl-9H-fluoren-2-yl)amine (3-1)
-continued
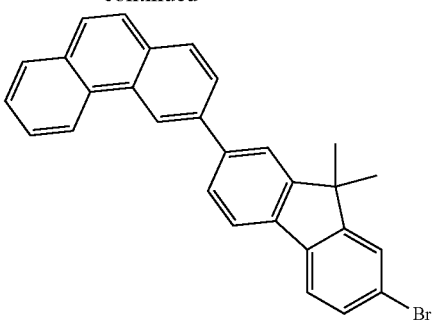
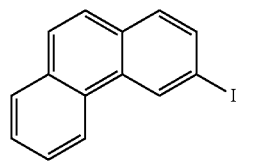 +
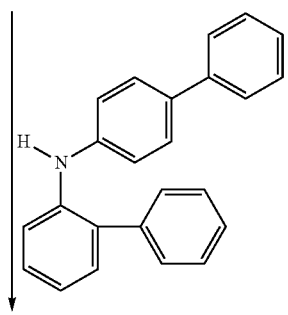
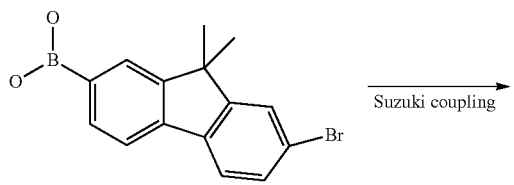 Suzuki coupling →
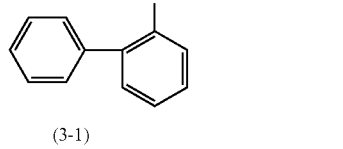
(3-1)

3-(7-Bromo-9,9-dimethyl-9H-fluoren-2-yl)phenanthrene 52 g (164 mmol) of 7-bromo(9,9-dimethylfluoren-2-yl)boronic acid (CAS No.: 1213768-48-9), 50 g (164 mmol) of 3-iodophenanthrene and 205 ml of a 2 M NaHCO$_3$ aqueous solution (327 mmol) are suspended in 800 ml of dimethoxyethane. 3.8 g (3.3 mmol) of tetrakis(triphenyl)phosphinepalladium(0) are added to this suspension, and the reaction mixture is heated under reflux for 16 h. After cooling, the organic phase is separated off, filtered through silica gel, washed three times with 300 ml of water and subsequently evaporated to dryness. Filtration of the crude product through silica gel with heptane/ethyl acetate (20:1) gave 55 g (75%) of 3-(7-bromo-9,9-dimethyl-9H-fluoren-2-yl)phenanthrenes.

Biphenyl-4-ylbiphenyl-2-yl-(9,9-dimethyl-7-phenanthren-3-yl-9H-fluoren-2-yl)amines 19.2 g of biphenyl-4-biphenyl-2-ylamine (60 mmol), 26.9 g of 3-(7-bromo-9,9-dimethyl-9H-fluoren-2-yl)phenanthrenes (60 mol) are dissolved in 500 ml of toluene: The solution is degassed and saturated with N$_2$. 3.2 g (3.9 mmol) of a tri-tert-butylphosphine solution and 0.27 g (1.2 mmol) of palladium(II) acetate are then added, and 8.9 g of sodium tert-butoxide (90 mmol) are subsequently added. The reaction mixture is heated at the boil under a protective atmosphere for 4 h. The mixture is subsequently partitioned between toluene and water, the organic phase is washed three times with water and dried over Na$_2$SO$_4$ and evaporated in a rotary evaporator. After filtration of the crude product through silica gel with toluene, the residue which remains is recrystallised from heptane/toluene and finally sublimed in a high vacuum, purity is 99.9%. The yield is 28 g (68% of theory.

Examples 20-22

Synthesis of Compounds (3-2) to (3-4)

The starting compounds are prepared analogously to the synthesis described in Example 18.

| Starting material 1 | Starting material 2 | Product | Yield |
| --- | --- | --- | --- |

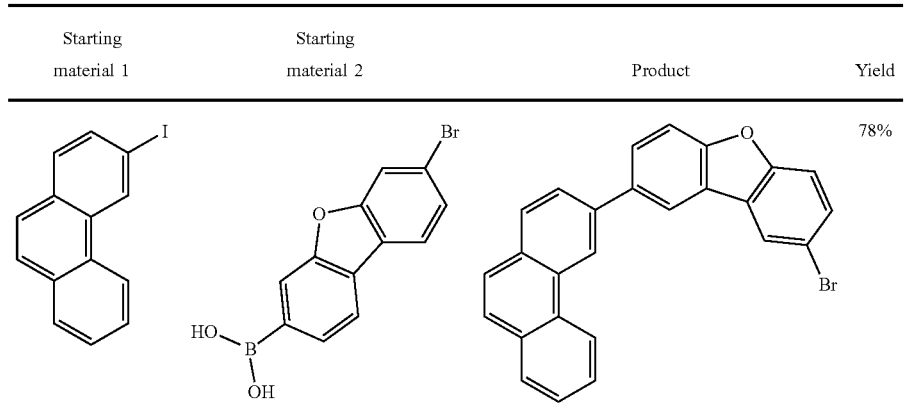

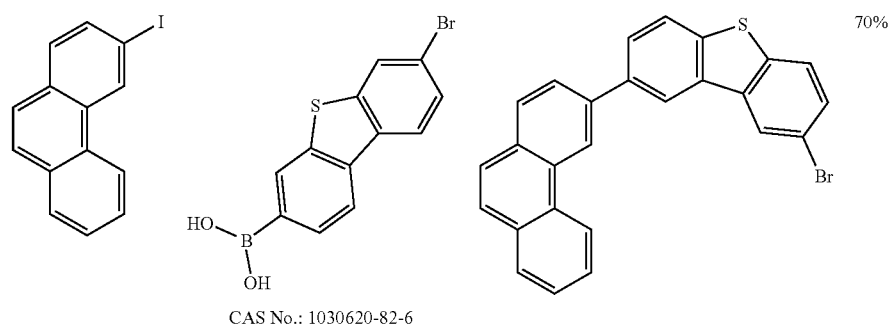

Compounds (3-2) to (3-4) are prepared analogously to the synthesis of compound (3-1) described in Example 19.
| | Starting material 1 | Starting material 2 | Product | Yield |
|---|---|---|---|---|
| 3-2 | 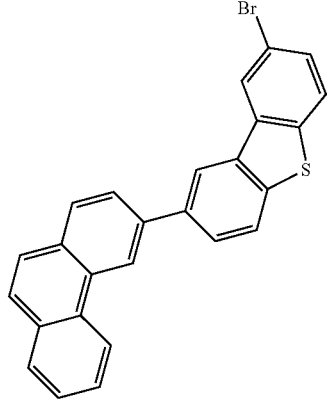 [SMILES: Brc1ccc2sc3ccc(-c4ccc5ccc6ccccc6c5c4)cc3c2c1] | 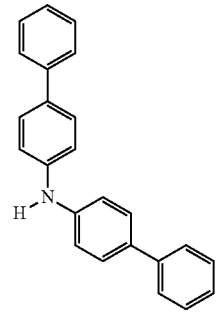 [SMILES: c1ccc(-c2ccc(Nc3ccc(-c4ccccc4)cc3)cc2)cc1] | 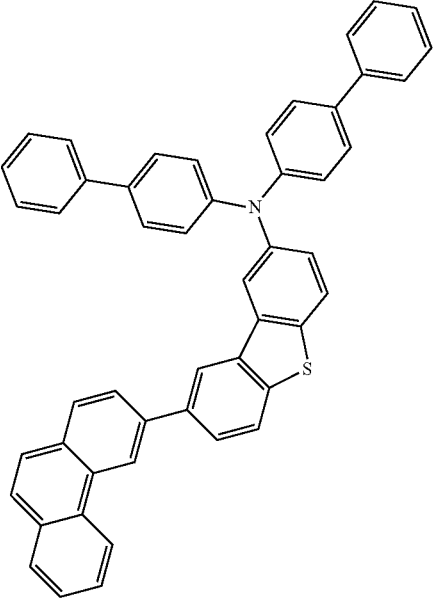 [SMILES: c1ccc(-c2ccc(N(c3ccc(-c4ccccc4)cc3)c3ccc4sc5ccc(-c6ccc7ccc8ccccc8c7c6)cc5c4c3)cc2)cc1] | 65% |
| 3-3 | 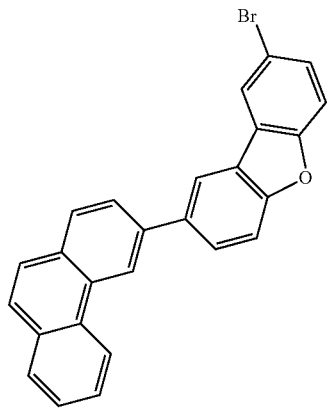 [SMILES: Brc1ccc2oc3ccc(-c4ccc5ccc6ccccc6c5c4)cc3c2c1] | 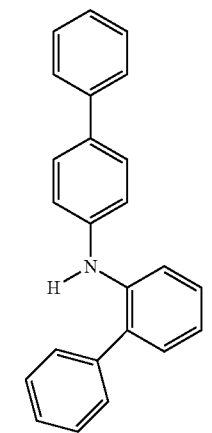 [SMILES: c1ccc(-c2ccc(Nc3ccccc3-c3ccccc3)cc2)cc1] | 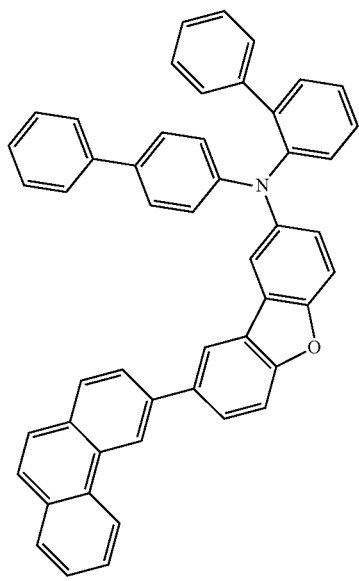 [SMILES: c1ccc(-c2ccc(N(c3ccc4oc5ccc(-c6ccc7ccc8ccccc8c7c6)cc5c4c3)c3ccccc3-c3ccccc3)cc2)cc1] | 75% |

-continued
| Starting material 1 | Starting material 2 | Product | Yield |
|---|---|---|---|
| 3-4 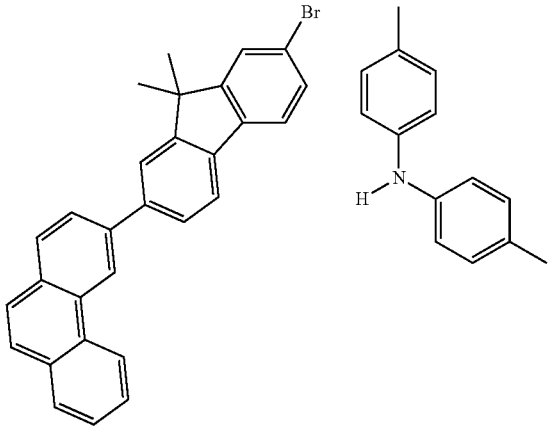 | 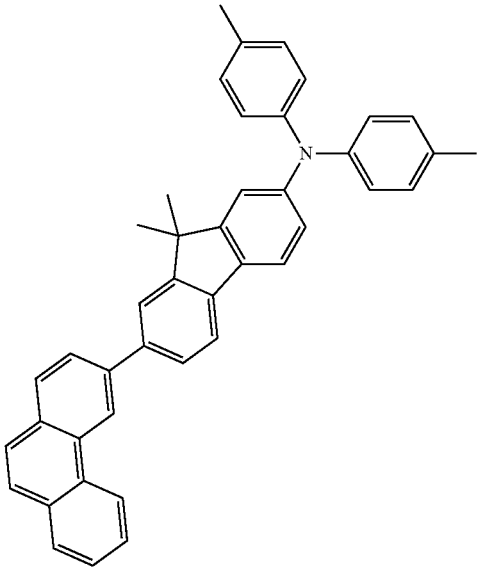 [SMILES: Cc1ccc(N(c2ccc(C)cc2)c2ccc3c(c2)C(C)(C)c2cc(-c4ccc5ccc6ccccc6c5c4)ccc2-3)cc1] | 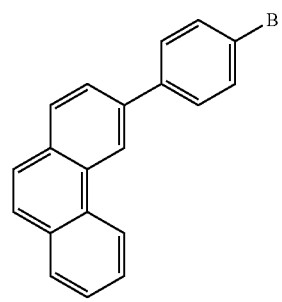 | 78% |
The comparative compound (V4) is also prepared analogously to the synthesis of compound (3-1) described in Example 19.
| Starting material 1 | Starting material 2 | Product |
|---|---|---|
| HTMV4 | | |
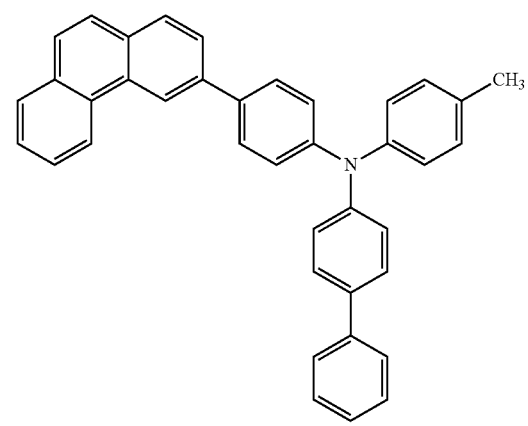 [SMILES: Cc1ccc(N(c2ccc(-c3ccccc3)cc2)c2ccc(-c3ccc4ccc5ccccc5c4c3)cc2)cc1]
Examples 23-25
Synthesis of the Compounds (9,9-dimethyl-9H-fluoren-2-yl)-(9,9-diphenyl-9H-fluoren-4-yl)phenanthren-3-ylamine (4-1), (4-2 and (4-3)
-continued
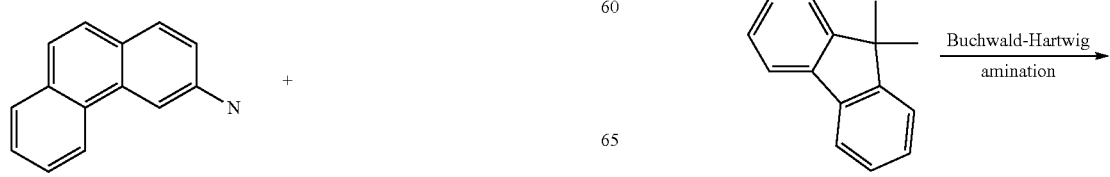

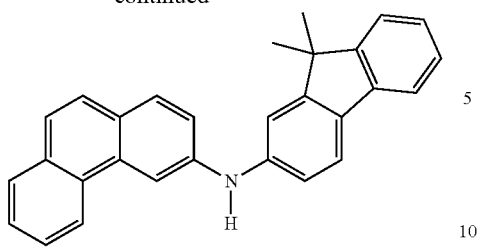

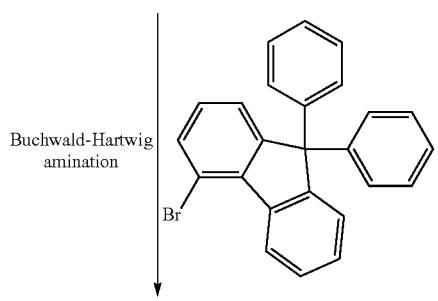

Buchwald-Hartwig amination

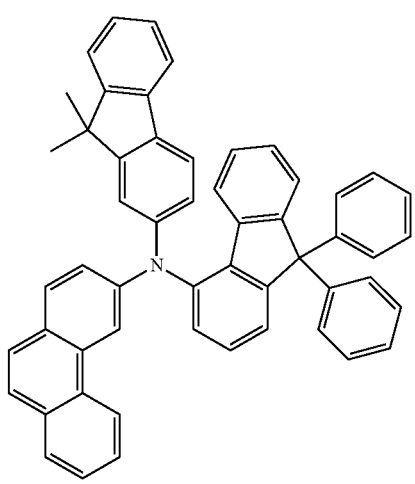

(4-1)

(9,9-Dimethyl-9H-fluoren-2-yl)phenanthren-3-ylamine 18.4 g (95.29 mmol) of 3-aminophenanthrene, 26 g (95.4 mmol) of 2-bromofluorene and 18.3 g (190 mmol) of sodium tert-butoxide are suspended in 350 ml of toluene. 1.07 g (4.76 mmol) of palladium acetate and 2.64 g of 1,1-bis(diphenylphosphino)ferrocene (4.76 mmol) are added to this suspension. The reaction mixture is heated under reflux for 16 h. After cooling, the organic phase is separated off washed three times with 200 ml of water and subsequently evaporated to dryness. The residue is recrystallised from toluene (31 g, 85% yield).

(9,9-Dimethyl-9H-fluoren-2-yl)-(9,9-diphenyl-9H-fluoren-4-yl)phenanthren-3-ylamine (4-1)

13.1 g of (9,9-dimethyl-9H-fluoren-2-yl)phenanthren-3-ylamine (34 mmol), 13.5 g of 4-bromo-9,9-diphenyl-9H-fluorene (34 mol) are dissolved in 300 ml of toluene: The solution is degassed and saturated with $N_2$. 1.4 ml (0.68 mmol) of a 1 M tri-tert-butylphosphine solution and 0.153 g (0.68 mmol) of palladium(II) acetate are then added, and 6.5 g of sodium tert-butoxide (68 mmol) are subsequently added. The reaction mixture is heated at the boil under a protective atmosphere for 4 h. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene and finally sublimed in a high vacuum, purity is 99.9%. The yield is 14.3 g (60% of theory).

The following compounds are prepared analogously:

| Starting material 1 | Starting material 2 | Product | Yield |
|---|---|---|---|
| 4-2 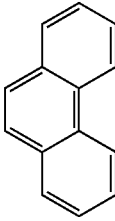 | 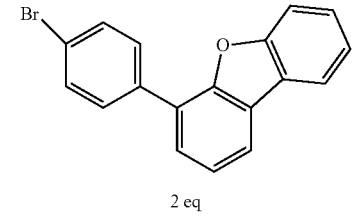 [SMILES: Brc1ccc(-c2cccc3c2oc2ccccc23)cc1] 2 eq | 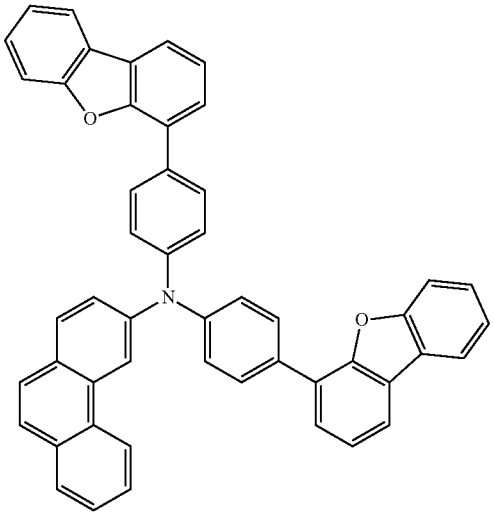 [SMILES: c1ccc2c(c1)ccc1ccc(N(c3ccc(-c4cccc5c4oc4ccccc45)cc3)c3ccc(-c4cccc5c4oc4ccccc45)cc3)cc12] | 65% |
| 4-3 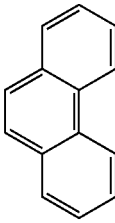 | 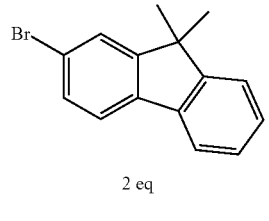 [SMILES: CC1(C)c2ccccc2-c2ccc(Br)cc21] 2 eq | 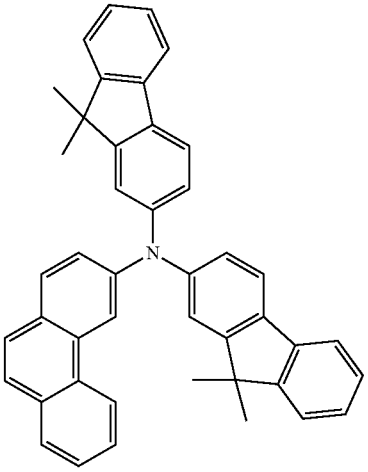 [SMILES: CC1(C)c2ccccc2-c2ccc(N(c3ccc4c(c3)C(C)(C)c3ccccc3-4)c3ccc4ccc5ccccc5c4c3)cc21] | 58% |

Example 26

Characterisation of the Compounds

OLEDs according to the invention and OLEDs in accordance with the prior art are produced by a general process in accordance with WO 2004/058911, which is adapted to the circumstances described here (layer-thickness variation, materials etc.).

The data of various OLEDs are shown in the following examples (see Tables 1 and 2). The substrates used are glass plates coated with structured ITO (indium tin oxide) in a thickness of 50 nm. The OLEDs have in principle the following layer structure: substrate/hole-injection layer (HIL1)/hole-transport layer (HIL2)/hole-injection layer (HIL3)/electron-blocking layer (EBL) I/emission layer (EML)/electron-transport layer (ETL)/electron-injection layer (EIL) and finally a cathode. The cathode is formed by an aluminium layer with a thickness of 100 nm. The precise structure of the OLEDs is revealed by Table 1. The materials required for the production of the OLEDs are shown above.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term EQE @ 1000 cd/m$^2$ denotes the external quantum efficiency at an operating luminous density of 1000 cd/m². LT80 @6000 cd/m2 is the lifetime by which the OLED has dropped from a luminance of 6000 cd/m² to 80% of the initial intensity, i.e. to 4800 cd/m². The data of the various OLEDs are summarised in Table 2.

Use of Compounds According to the Invention as Matrix Materials in Fluorescent OLEDs Compounds according to the invention are particularly suitable as HIL, HTL or EBL in OLEDs. They are suitable as a single layer, but also as mixed component as HIL, HTL, EBL or within the EML.

Compared with NPB reference components (V1), all samples comprising the compounds according to the invention exhibit both higher efficiencies and also significantly improved lifetimes in singlet blue.

Compared with the reference material HTMV1-HTMV5 (V2-V6), the compound (1-9), (1-1) and (1-11) according to the invention have better efficiencies and improved lifetimes. Compared with HTMV6 and HTMV7 (V7 and V8), the compound (1-1) according to the invention has a significantly improved lifetime.

TABLE 1

Structure of the OLEDs
IL (5 nm HIL1)/HTL (150 nm HIL2)/IL(5 nm HIL1)/EBL/EML/ETL

| Ex. | EBL Thickness/nm | EML Thickness/nm | ETL Thickness/nm |
|---|---|---|---|
| V1 | NPB 20 nm | H1(95%):SEB1(5%) 20 nm | ETM1(50%):LiQ(50%) 30 nm |
| V2 | HTMV1 20 nm | H1(95%):SEB1(5%) 20 nm | ETM1(50%):LiQ(50%) 30 nm |
| V3 | HTMV2 20 nm | H1(95%):SEB1(5%) 20 nm | ETM1(50%):LiQ(50%) 30 nm |
| V4 | HTMV3 20 nm | H1(95%):SEB1(5%) 20 nm | ETM1(50%):LiQ(50%) 30 nm |
| V5 | HTMV4 20 nm | H1(95%):SEB1(5%) 20 nm | ETM1(50%):LiQ(50%) 30 nm |
| V6 | HTMV5 20 nm | H1(95%):SEB1(5%) 20 nm | ETM1(50%):LiQ(50%) 30 nm |
| V7 | HTMV6 20 nm | H1(95%):SEB1(5%) 20 nm | ETM1(50%):LiQ(50%) 30 nm |
| V8 | HTMV7 20 nm | H1(95%):SEB1(5%) 20 nm | ETM1(50%):LiQ(50%) 30 nm |
| E0 | HTMV8 20 nm | H1(95%):SEB1(5%) 20 nm | ETM1(50%):LiQ(50%) 30 nm |
| E1 | (1-9) 20 nm | H1(95%):SEB1(5%) 20 nm | ETM1(50%):LiQ(50%) 30 nm |
| E2 | (1-1) 20 nm | H1(95%):SEB1(5%) 20 nm | ETM1(50%):LiQ(50%) 30 nm |
| E3 | (1-11) 20 nm | H1(95%):SEB1(5%) 20 nm | ETM1(50%):LiQ(50%) 30 nm |
| E4 | (1-12) 20 nm | H1(95%):SEB1(5%) 20 nm | ETM1(50%):LiQ(50%) 30 nm |
| E5 | (2-6) 20 nm | H1(95%):SEB1(5%) 20 nm | ETM1(50%):LiQ(50%) 30 nm |
| E6 | (1-2) 20 nm | H1(95%):SEB1(5%) 20 nm | ETM1(50%):LiQ(50%) 30 nm |
| E7 | (4-1) 20 nm | H1(95%):SEB1(5%) 20 nm | ETM1(50%):LiQ(50%) 30 nm |

TABLE 2

| | Data of the OLEDs | | | |
|---|---|---|---|---|
| | EQE @ 1000 cd/m2 | LT80 @ 6000 cd/m² | CIE | |
| Ex. | % | [h] | x | y |
| V1 | 4.8 | 70 | 0.14 | 0.17 |
| V2 | 6.4 | 20 | 0.13 | 0.16 |
| V3 | 5.4 | 25 | 0.13 | 0.15 |

TABLE 2-continued

| | Data of the OLEDs | | | |
|---|---|---|---|---|
| | EQE @ 1000 cd/m2 | LT80 @ 6000 cd/m² | CIE | |
| Ex. | % | [h] | x | y |
| V4 | 6.6 | 65 | 0.13 | 0.15 |
| V5 | 5.6 | 80 | 0.13 | 0.15 |
| V6 | 5.0 | 60 | 0.13 | 0.16 |
| V7 | 6.8 | 100 | 0.14 | 0.14 |
| V8 | 6.9 | 110 | 0.14 | 0.15 |
| E0 | 6.8 | 115 | 0.13 | 0.16 |
| E1 | 6.7 | 125 | 0.13 | 0.15 |
| E2 | 7.0 | 155 | 0.13 | 0.15 |
| E3 | 6.9 | 135 | 0.13 | 0.15 |
| E4 | 6.8 | 120 | 0.13 | 0.15 |
| E5 | 5.0 | 80 | 0.13 | 0.16 |
| E6 | 7.1 | 125 | 0.13 | 0.15 |
| E7 | 7.1 | 120 | 0.13 | 0.15 |

Example E0 exhibits a significantly improved LT50 value compared with Comparative Examples V1 to V8. Further, significant improvements compared both with the comparative examples and also compared with E0 can be achieved by the phenanthrene, apart from position 3, having no further aromatic and/or heteroaromatic substitution (E1 to E7). Compound (2-6) (E5) can be compared directly with NPB (V1). It can be seen that compound (2-6) results in devices having significantly improved EQE values and in particular in improved LT80 values.

The invention claimed is:

1. A compound of the formula (1)

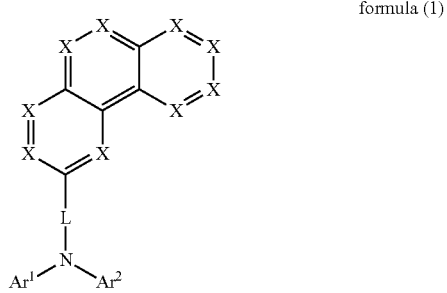

formula (1)

where the following applies to the symbols and indices occurring:
X is on each occurrence, identically or differently, N and CR¹ where a maximum of 2 of the X is optionally equal to N;
L is a single bond or a divalent aryl or heteroaryl group having 12 to 40 ring atoms, which is optionally substituted by one or more radicals R², where, if L is a single bond, the nitrogen is bonded directly to position 3 of the phenanthrene;
Ar¹ is selected from formulae (9)-(28), (20')-(20"), (29)-(36) (32')-(34') and (37)-(100):

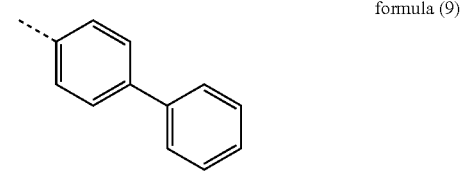

formula (9)

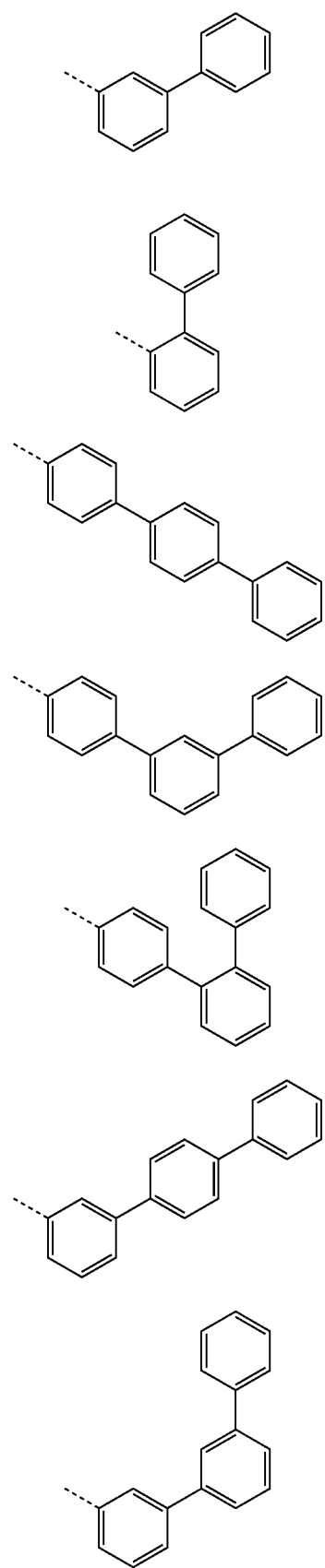
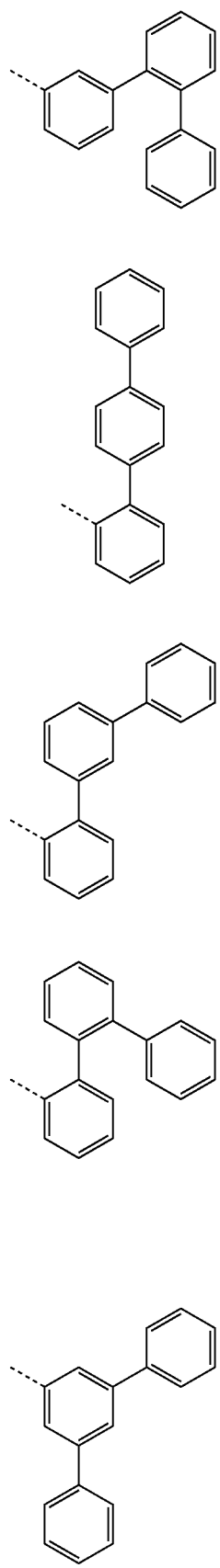
formula (10)
formula (11)
formula (12)
formula (13)
formula (14)
formula (15)
formula (16)
formula (17)
formula (18)
formula (19)
formula (20)
formula (21)

| formula (22) | 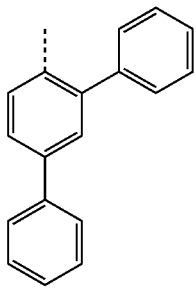 |
| formula (23) | 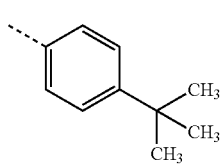 |
| formula (24) | 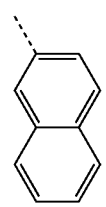 |
| formula (25) | 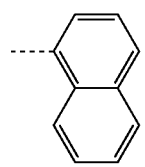 |
| formula (26) | 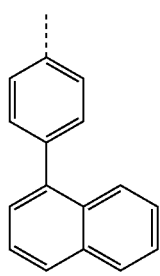 |
| formula (27) | 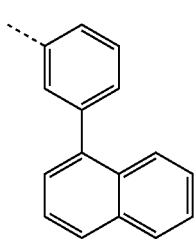 |
| formula (28) | 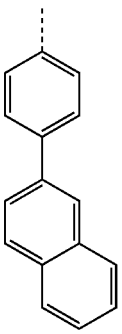 |
| formula (20') | 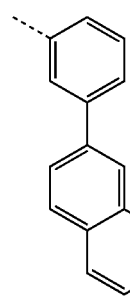 |
| formula (20") | 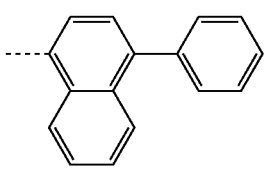 |
| formula (20''') | 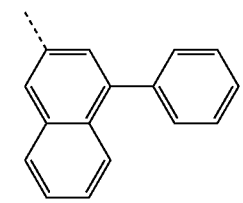 |
| formula (29) | 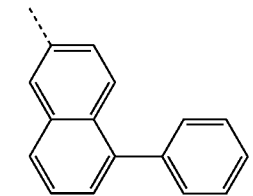 |
| formula (30) | 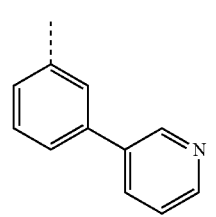 |
| formula (31) | |

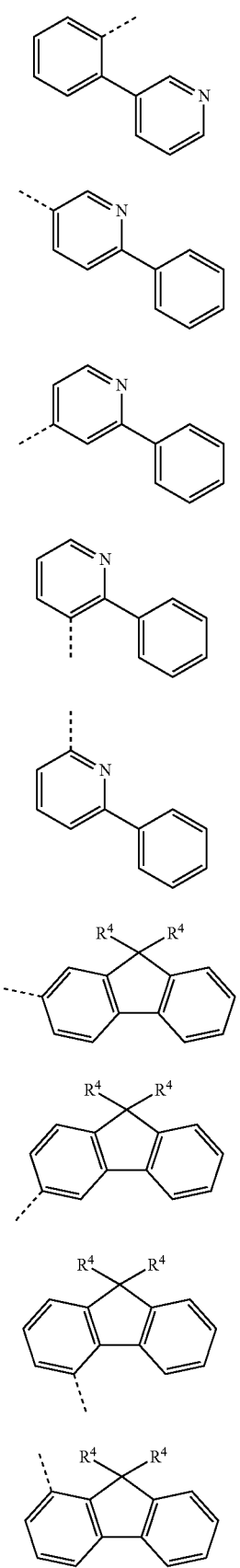
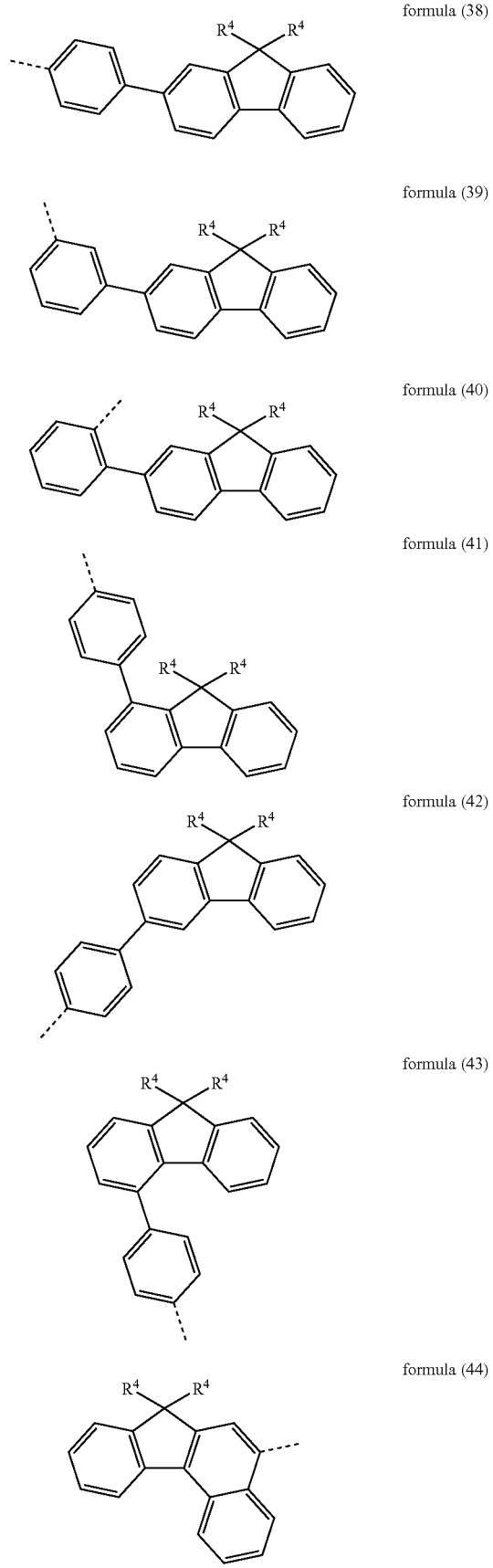

199
-continued
formula (45)
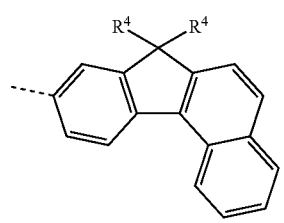
formula (46)
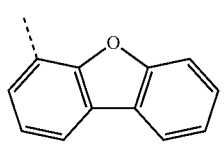
formula (47)
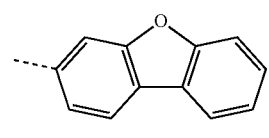
formula (48)
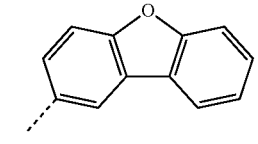
formula (49)
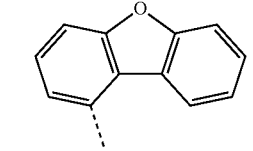
formula (50)
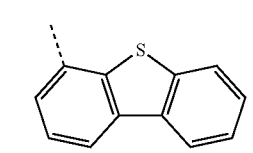
formula (51)
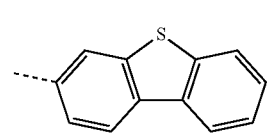
formula (52)
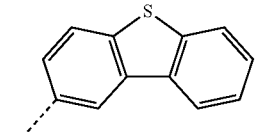
formula (53)
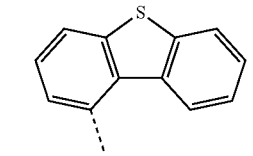
200
-continued
formula (54)
formula (55)
formula (56)
formula (57)
formula (58)
formula (59)
formula (60)

201
-continued
formula (61)
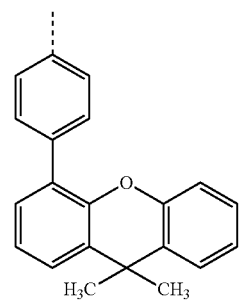
formula (62)
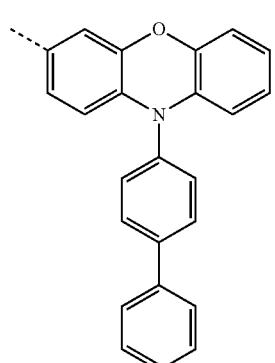
formula (63)
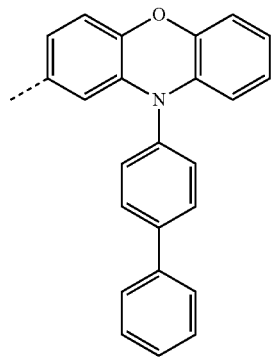
formula (64)
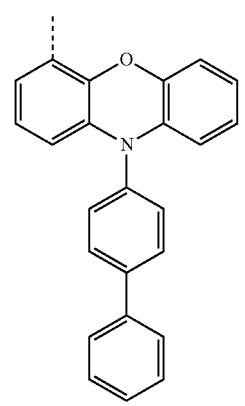
202
-continued
formula (65)
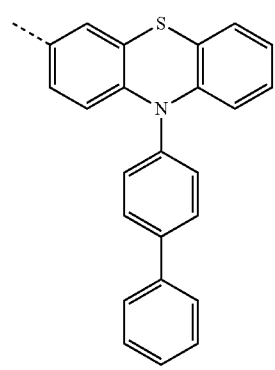
formula (66)
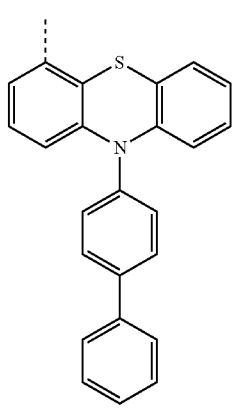
formula (67)
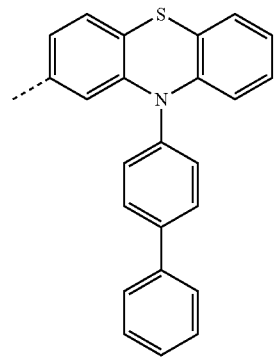
formula (68)
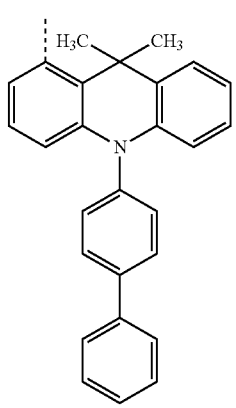

203
-continued
formula (69)
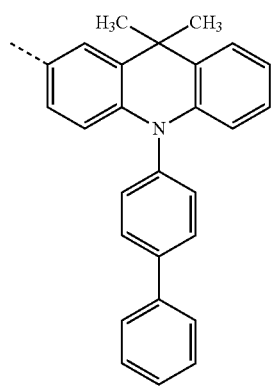
formula (70)
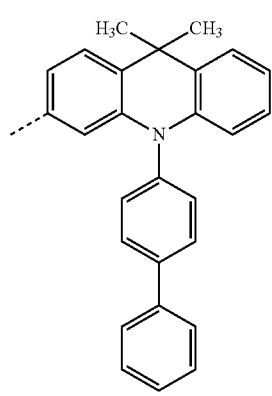
formula (71)
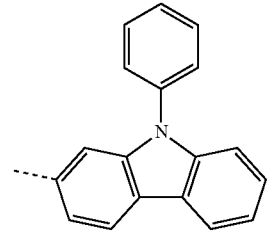
formula (72)
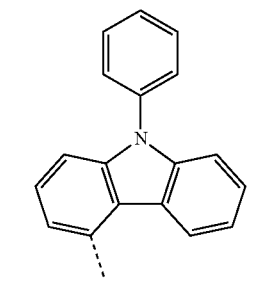
formula (73)
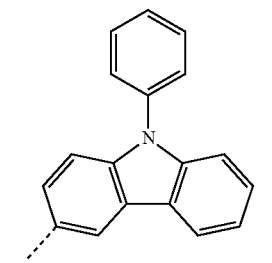
204
-continued
formula (74)
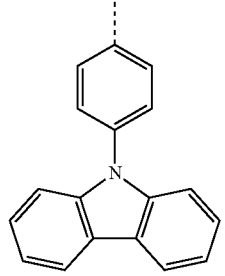
formula (75)
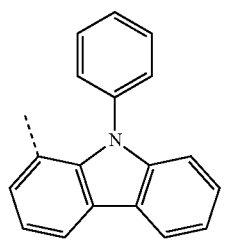
formula (76)
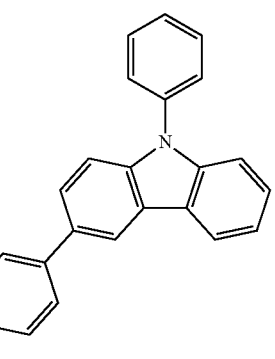
formula (77)
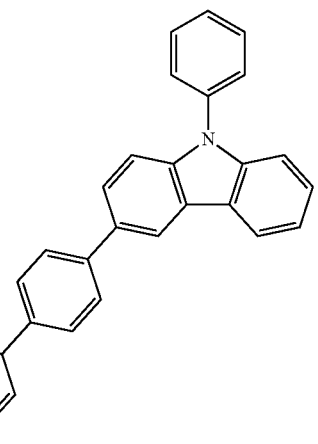

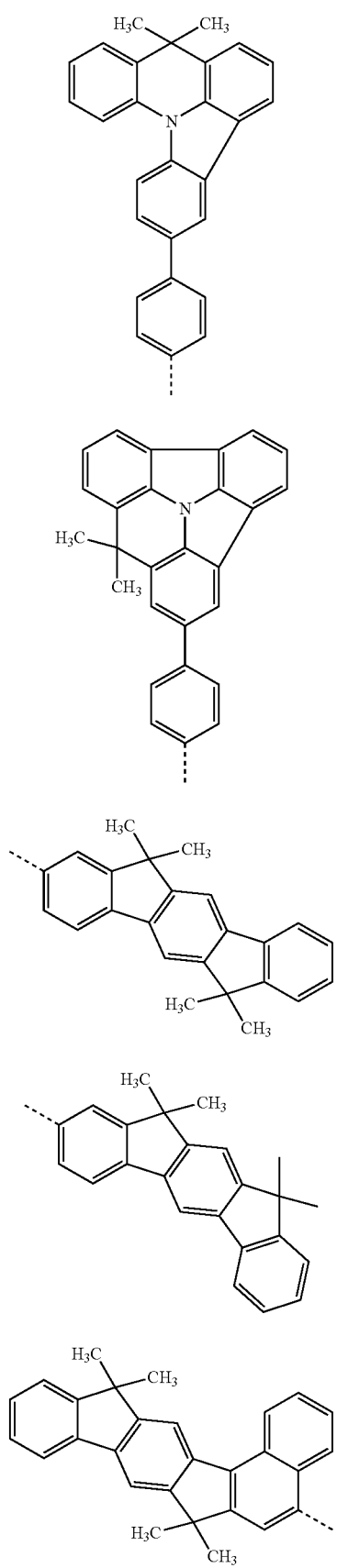
formula (78)
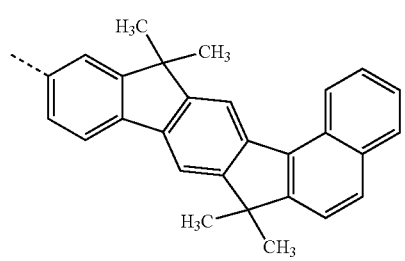
formula (83)
formula (79)
formula (84)
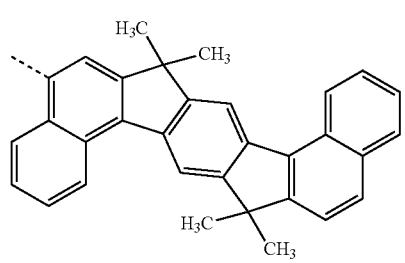
formula (80)
formula (85)
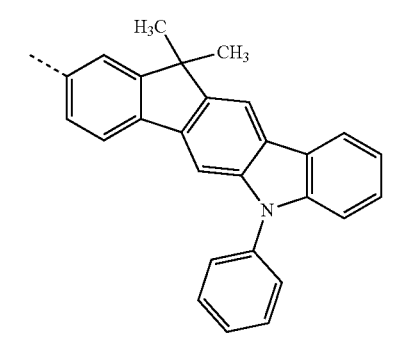
formula (81)
formula (86)
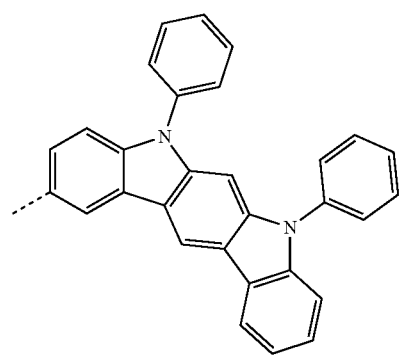
formula (82)
formula (87)
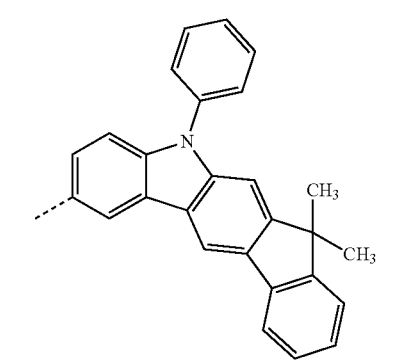

formula (88)
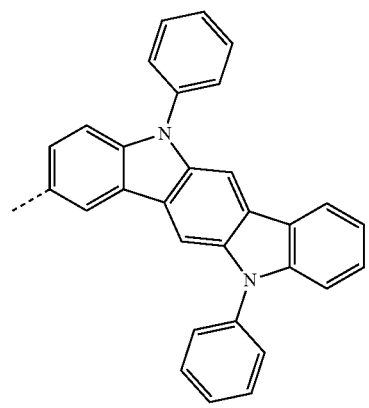
formula (89)
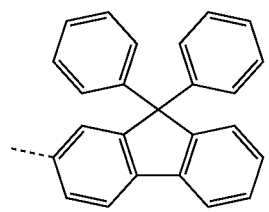
formula (90)
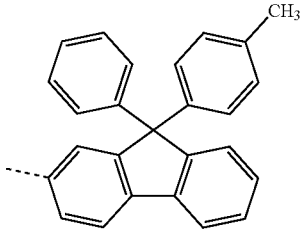
formula (91)
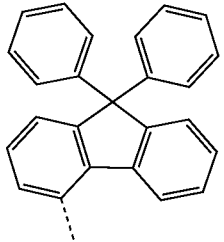
formula (92)
formula (93)
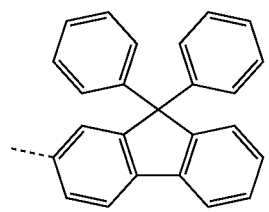
formula (94)
formula (95)
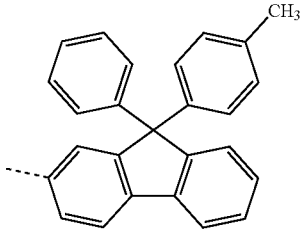
formula (96)
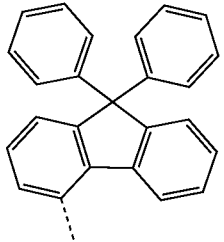
formula (97)
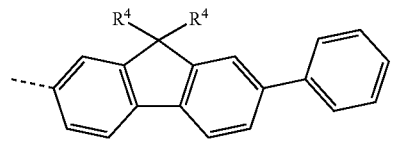
formula (98)
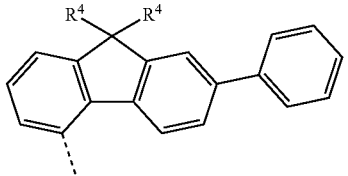
formula (99)
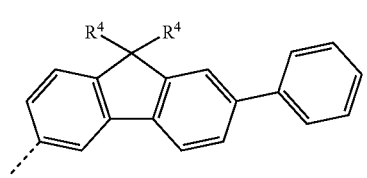

-continued formula (100)

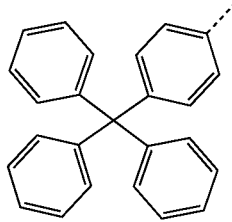

where the dashed line represents the bonding position and where the structures may be substituted by one or more radicals $R^{4'}$, and $R^{4'}$ is on each occurrence, identically or differently, D, F, Cl, Br, I, C(=O)R$^2$, CN, Si(R$^2$)$_3$, NR$^2$, NO$_2$, P(=O)(R$^2$)$_2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more CH$_2$ groups in the above-mentioned groups is optionally replaced by —R$^2$C=CR$^2$—, Si(R$^2$)$_2$, C=O, C=S, C=NR$^2$, —C(=O)O—, —C(=O)NR$^2$—, P(=O)(R$^2$), —O—, —S—, SO or SO$_2$ and where one or more H atoms in the above-mentioned groups is optionally replaced by D, F, Cl, Br, I, CN or NO$_2$, or an aromatic ring system having 6 to 30 aromatic ring atoms, which may in each case be substituted by one or more radicals $R^2$, where two or more radicals $R^{4'}$ is optionally linked to one another and may form a ring;

Ar$^2$ is on each occurrence, identically or differently, an aromatic or heteroaromatic ring or an aromatic or heteroaromatic ring system having 5 to 40 aromatic ring atoms, where the ring or ring system is optionally substituted by one or more radicals $R^4$, where, if both Ar$^1$ and also Ar$^2$ are phenyl radicals, at least one R$^4$ on the phenyl radicals is not equal to H and this at least one radical R$^4$ optionally contains one or more aromatic or heteroaromatic rings;

$R^1$ is on each occurrence, identically or differently, H, D, F, Cl, Br, I, C(=O)R$^2$, CN, Si(R$^2$)$_3$, NO$_2$, P(=O)(R$^2$)$_2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more CH$_2$ groups in the above-mentioned groups is optionally replaced by —R$^2$C=CR$^2$—, —C≡C—, Si(R$^2$)$_2$, C=O, C=S, C=NR$^2$, —C(=O)O—, —C(=O)NR$^2$—, P(=O)(R$^2$), —O—, —S—, SO or SO$_2$ and where one or more H atoms in the above-mentioned groups is optionally replaced by D, F, Cl, Br, I, CN or NO$_2$, or an aromatic ring system having 6 to 30 aromatic ring atoms, which may in each case be substituted by one or more radicals $R^2$, where two or more radicals R$^1$ is optionally linked to one another and may form a ring;

$R^4$ is on each occurrence, identically or differently, H, D, F, Cl, Br, I, C(=O)R$^2$, CN, Si(R$^2$), NR$^2$, NO$_2$, P(=O)(R$^2$)$_2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more CH$_2$ groups in the above-mentioned groups is optionally replaced by —R$^2$C=CR$^2$—, Si(R$^2$)$_2$, C=O, C=S, C=NR$^2$, —C(=O)O—, —C(=O)NR$^2$—, P(=O)(R$^2$), —O—, —S—, SO or SO$_2$ and where one or more H atoms in the above-mentioned groups is optionally replaced by D, F, Cl, Br, I, CN or NO$_2$, or an aromatic ring system having 6 to 30 aromatic ring atoms, which may in each case be substituted by one or more radicals $R^2$, where two or more radicals R$^4$ is optionally linked to one another and may form a ring;

$R^2$ is on each occurrence, identically or differently, H, D, F, Cl, Br, I, C(=O)R$^3$, CN, Si(R$^3$)$_3$, NO$_2$, P(=O)(R$^3$)$_2$, S(=O)R$^3$, S(=O)$_2$R$^3$, a straight-chain alkyl, alkoxy or thio-alkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups is optionally replaced by —R$^3$C=CR$^3$—, Si(R$^3$)$_2$, CO, =C=S, C=NR$^3$, —C(=O)O—, —C(=O)NR$^3$—, P(=O)(R$^3$), —O—, —S—, SO or SO$_2$ and where one or more H atoms in the above-mentioned groups is optionally replaced by D, F, Cl, Br, I, CN or NO$_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which is optionally substituted by one or more radicals $R^3$, where two or more radicals R$^2$ is optionally linked to one another and optionally form a ring;

$R^3$ is on each occurrence, identically or differently, H, D, F or an aliphatic, aromatic or heteroaromatic organic radical having 1 to 20 C atoms, in which, in addition, one or more H atoms is optionally replaced by D or F; two or more substituents R$^3$ here is optionally linked to one another and optionally form a ring;

where the compound of the formula (1), besides the phenanthrene, contains no further condensed aromatic or heteroaromatic ring having more than 10 ring atoms and where the radicals R$^1$ on the phenanthrene in formula (1) contain no further amine groups.

2. The compound according to claim 1, wherein the compound is of the formula (2):

formula (2)

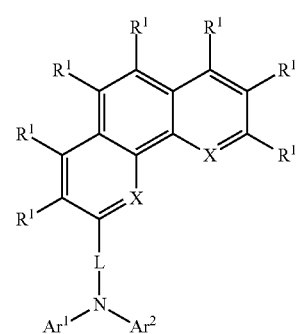

where the definitions from claim 1, apply to the symbols used.

3. The compound according to claim 1, wherein the compound is of the formula (5):

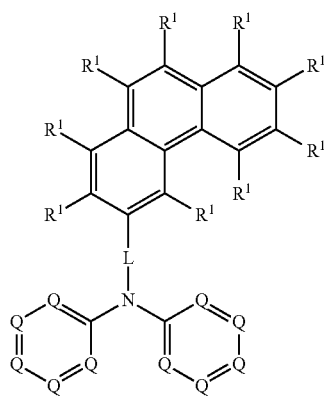

formula (5)

where Q is on each occurrence, identically or differently, $CR^4$ or N.

4. The compound according to claim 1, wherein the compound is of the formula (6):

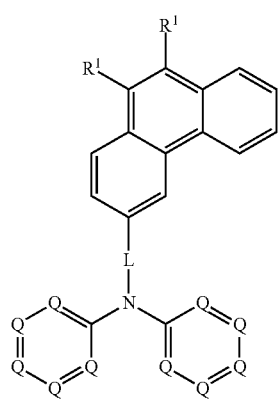

formula (6)

where Q is on each occurrence, identically or differently, $CR^4$ or N.

5. The compound according to claim 1, wherein the compound is of the (7):

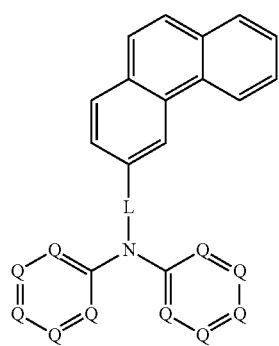

formula (7)

where Q is on each occurrence, identically or differently, $CR^4$ or N.

6. The compound according to claim 1, wherein L is an aromatic ring system selected from the group consisting of biphenylenes, terphenylenes and the compounds of the formula (101a) and (101b),

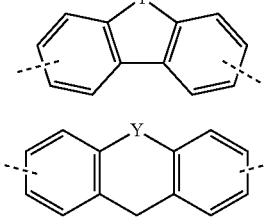

formula (101a)

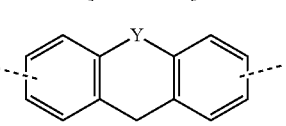

formula (101b)

where Y is equal to $C(R^2)_2$, $NR^2$, O, $Si(R^2)_2$ or S.

7. The compound according to claim 6, wherein Y is $C(R^2)_2$ or $NR^2$.

8. The compound according to claim 1, wherein L is a single bond, so that the amine group is bonded directly to the phenanthrene.

9. The compound according to claim 1, wherein the compound contains in total at least 26 ring atoms.

10. The compound according to claim 1, wherein the compound contains only one amine group.

11. A process for the preparation of the compound according to claim 1 which comprises a one-step Buchwald coupling by reaction of a phenanthrene derivative which contains a leaving group with $Ar^2$—NH—$Ar^1$.

12. A process for the preparation of the compound according to claim 1 which comprises a two-step Buchwald coupling by stepwise reaction of a phenanthrene derivative which contains a leaving group with (1) $Ar^2$—$NH_2$ and (2) $NH_2$—$Ar^1$.

13. An oligomer, polymer or dendrimer containing one or more compounds according to claim 1, where the bond(s) to the polymer, oligomer or dendrimer is optionally localized at any positions in formula (1) which are substituted by $R^1$, $R^4$ or $R^2$.

14. A composition comprising one or more compounds according to claim 1 and at least one further organically functional material selected from the group consisting of fluorescent emitters, phosphorescent emitters, host materials, matrix materials, electron-transport materials, electron-injection materials, hole-conductor materials, hole-injection materials, electron-blocking materials and hole-blocking materials.

15. A formulation comprising at least one compound according to claim 1 and at least one solvent.

16. An electronic device comprising at least one compound according claim 1.

17. The electronic device according to claim 16, wherein the device is selected from organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

18. An organic electroluminescent device which comprises the compound according to claim 1 employed in one or more of the following functions:

as hole-transport material in a hole-transport or hole-injection layer,
as matrix material in an emitting layer,
as electron-blocking material,
as exciton-blocking material.

* * * * *

UNITED STATES PATENT AND TRADEMARK OFFICE
CERTIFICATE OF CORRECTION

PATENT NO. : 11,424,411 B2
APPLICATION NO. : 16/561188
DATED : August 23, 2022
INVENTOR(S) : Mujica-Fernaud et al.

It is certified that error appears in the above-identified patent and that said Letters Patent is hereby corrected as shown below:

In the Claims

In Claim 1, Column 209, Line 17, in the definition of $R^{4'}$:
"F, Cl, Br, I, C(=O)$R^2$, CN, Si($R^2$)3, N$R^2$, $NO_2$, P(=O)"
Should read:
-- F, Cl, Br, I, C(=O)$R^2$, CN, Si($R^2$)$_3$, N($R^2$)$_2$, $NO_2$, P(=O) --

In Claim 1, Column 209, Line 64, in the definition of $R^4$:
"F, Cl, Br, I, C(=O)$R^2$, CN, Si($R^2$)3, N$R^2$, $NO_2$, P(=O)"
Should read:
-- F, Cl, Br, I, C(=O)$R^2$, CN, Si($R^2$)$_3$, N($R^2$)$_2$, $NO_2$, P(=O) --

Signed and Sealed this
Tenth Day of January, 2023

*Katherine Kelly Vidal*

Katherine Kelly Vidal
*Director of the United States Patent and Trademark Office*